United States Patent [19]

Trivette, Jr.

[11] 3,979,369

[45] Sept. 7, 1976

[54] METHOD FOR CROSS-LINKING RUBBER WITH POLYSULFIDES

[75] Inventor: Chester Draper Trivette, Jr., Akron, Ohio

[73] Assignee: Monsanto Company, St. Louis, Mo.

[22] Filed: Sept. 20, 1974

[21] Appl. No.: 507,763

Related U.S. Application Data

[62] Division of Ser. No. 200,595, Nov. 19, 1971, Pat. No. 3,869,435.

[52] U.S. Cl. .................. 260/79.5 C; 260/79.5 B; 260/247.1 R; 260/453 R; 260/784; 260/785; 526/20; 526/30; 526/335

[51] Int. Cl.² ................ C08C 11/60; C08C 11/54; C08C 11/66; C08D 9/00

[58] Field of Search ............... 260/79.5 AA, 79.5 B, 260/79.5 C, 608, 775, 783, 779, 784, 785, 787; 252/184

[56] References Cited

UNITED STATES PATENTS

| | | | |
|---|---|---|---|
| 3,647,885 | 3/1972 | Geering | 260/608 |
| 3,705,923 | 3/1975 | Sullivan | 260/608 |

*Primary Examiner*—Christopher A. Henderson, Jr.
*Attorney, Agent, or Firm*—Richard O. Zerbe

[57] ABSTRACT

Rubber is cross-linked by heating with compounds of the formula $(Acc-SS_x)_nR$ wherein Acc-S— is an accelerating moiety, R is an organic bridging group and n is two or more.

42 Claims, No Drawings

METHOD FOR CROSS-LINKING RUBBER WITH POLYSULFIDES

This application is a divisional application of application Ser. No. 200,595 filed Nov. 19, 1971 now U.S. Pat. No. 3,869,435 issued Mar. 4, 1975.

BACKGROUND OF THE INVENTION

Vulcanization of rubber normally gives sulfidic cross-links in allylic position with respect to a double bond in the vulcanizate coupled with some cyclization instead of cross-linking as well as other undesirable side reactions. When elemental sulfur is the vulcanizing agent the cross-links are mainly polysulfidic and it is now recognized that polysulfidic cross-links as compared to monosulfidic cross-links reduce thermal stability of the vulcanizate. There have been suggestions to modify the cross-linking reaction by reacting rubber with dithiols to introduce an organic bridging element into the cross-link. However, dithiols add across double bonds of adjacent rubber molecules reducing unsaturation by a cross-linking reaction different from the classical vulcanization reaction. J. LeBras, *Kautschuk U. Gummi*, V15, WT 407-WT 418 (1962), FIG. 14; G. E. Meyer et al., *Rubber World*, V136, 529 (1957); C. M. Hull, *Ind. J Eng. Chem.*, V40, 513 (1948). If a derivative of mercaptobenzothiazole is used as the accelerator in the classical vulcanization reaction with elemental sulfur it is known that mercaptobenzothiazole is generated in the process. Some theories devised to explain the mechanism of cross-linking rubber by the action of elemental sulfur and organic accelerator which is a mercaptan or derivative thereof assume that the accelerator reacts with sulfur to form polysulfide (herein meaning two or more sulfur atoms) and propose a cross-linking scheme involving free radical intermediates whereby a rubber polythiyl radical cross-link precursor forms which reacts preferentially with the polysulfide until all is combined with the rubber, then cross link formation begins. Coran, *Rubber Chem. Technol.* 37, 689 (1964). The theory is capable of explaining observed kinetics of vulcanization but it is difficult to write satisfactory steps for the actual cross-linking process itself. In vulcanization of diene rubber with tetramethylthiuram disulfide, evidence for formation of a rubber bound intermediate

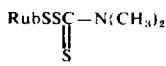

which is the precursor to sulfur cross-linking, has been reported. Porter, The Chemistry of Sulfides, Interscience Publishers, p. 165-183. The mechanism by which a rubber bound intermediate forms is unknown. However, it is generally accepted that the initial step in sulfur vulcanization is the reaction of sulfur with a species derived from the accelerator.

SUMMARY OF THE INVENTION

If it is postulated that cross-link formation results from direct reaction of accelerator polysulfide intermediates via a concerted mechanism and that there is ultimately formed from reaction of accelerator and sulfur a polysulfide, Acc-SS$_x$-S-Acc, the simplest cross-linking reaction is

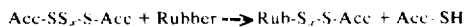

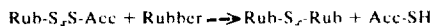

Consistent with the foregoing scheme it has now been found that a compound containing two Acc-SS$_x$— groups connected through an organic bridging group R is a primary vulcanizing agent, R of which becomes part of the cross-link and the sulfur in the cross-link is monosulfidic if $x$ is one. The cross-linking function with unsaturated rubber may be illustrated as follows:

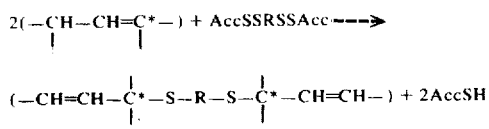

Experimental results are consistent with the foregoing scheme of vulcanization. Although the invention is not limited to any theory by which cross-links form there can now be no doubt that compounds of the aforesaid characteristics comprise a general class of primary cross-linking agents. The mechanisms and the nature of the cross-links are undoubtedly more complex than illustrated and the cross-link may, for example, involve multiples of (SRS).

Accordingly, the present invention provides a new cross-linking reaction wherein organic bridging groups are introduced into the cross-link in allylic position. The adjuvants for effecting said reaction which are for the most part new compounds, may be represented by the formula (Acc-SS$_x$)$_n$R-S$_x$-S-Acc wherein Acc-S— is the same or different accelerating moiety, $x$ is 1, 2, 3 or 4, $n$ is 1, 2 or 3 and R is an organic bridging group of valence $n$ +1. Accelerating moiety refers to a nucleus contained in compounds which accelerate the vulcanization of natural and synthetic diene rubbers. Organic mercaptans, disulfides and other mercaptan derivatives have been widely used to accelerate vulcanization or rubber. Well known mercaptans or mercaptan derived accelerators are represented by the formula Acc-S-M where M is typically hydrogen, metal or in the case of disulfides, is Acc-S— and Acc- is the residue of an accelerating mercaptan. The mercaptan and mercaptan derived accelerators may be conveniently represented as containing the moiety Acc-S— and it will be noted that at least two such moieties are present in the new cross-linking agents and are linked through at least one additional sulfur atom to an organic bridging radical. The accelerating moiety will usually be the same but may be different and sometimes different accelerating moieties are advantageous.

An exhaustive discussion of mercaptans and derivatives known for accelerating vulcanization of rubber is unnecessary for an understanding of the invention. The accelerating moiety may be the residue of any mercaptan which enhances the vulcanization rate of diene rubber with sulfur. Illustrative of well known classes of accelerators from which the accelerating moiety may be derived are 2-mercaptoazoles, dithiocarbamates, phosphorodithioates and xanthates. Others will be discussed hereinafter and all of them copiously illustrated although it will be appreciated that the accelerating moiety per se is in general well known.

The organic bridging group R is largely a matter of choice. Selection of particular R groups is unnecessary for effecting the cross-link reaction but the R group in the cross-linking agent will exert some influence on the efficiency of the cross-linking reaction and on scorch and cure rates. Of course, it might be possible to find functional bridging groups which would defeat the purpose of the invention but it is assumed that no one would desire to obtain a useless result and that no one will be misled by the permissible wide variation in R. This great variety of R groups found useful renders it impossible to define them in simple structural form and language to designate the genus is non-existent. For convenience, it will be understood that the term "organic bridging groups" as used herein means the organic radicals described herein for purposes of illustrating R. It is believed, however, that equivalents will be readily suggested therefrom. For example, no reason appears why R must be confined to any particular number of carbon atoms and R groups of fifty or more carbon atoms would still be expected to provide useful results.

Illustrative of azole radicals which are suitable for Acc in the above formula are oxazole, imidazole and thiazole represented by the formula

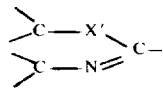

wherein the unsatisfied valences on the vicinal carbon atoms are attached to hydrogen, lower alkyl, benzyl, acetyl, carboalkoxy and phenyl or together with the carbon atoms forms an alicyclic ring or an ortho arylene ring, or two of the unsatisfied valences are joined to form a double bond. The ortho arylene ring may be substituted by lower alkyl, halo, nitro, hydroxy, carboalkoxy, acetyl, lower alkoxy and phenyl radicals, and X' is S, O or NH. Lower alkyl means radicals containing 1–5 carbon atoms.

Specific examples of azole radicals in the cross-linking agents are 2-thiazolyl, 2-thiazolinyl, 2-oxazolyl, 2-oxazolinyl, 2-imidazolyl, 2-imidazolinyl, 2-benzothiazolyl, 2-benzoxazolyl, 2-benzimidazolyl, 2-naphthathiazolyl, 2-dihydrobenzothiazolyl, 2-(4,5,6,7-tetrahydrobenzothiazolyl), 2-(4-methylthiazolyl), 2-(4-methyloxazolyl), 2-(4-methylimidazolyl), 2-(4-ethylthiazolyl), 2-(4-ethyloxazolyl), 2-(4-ethylimidazolyl), 2-(4-n-propyltiazolyl), 2-(4-n-propyloxazolyl), 2-(4-n-propylimidazolyl), 2-(4-n-butylthiazolyl), 2-(4-n-butyloxazolyl), 2-(4-n-propylimidazolyl), 2-(4,5-dimethylthiazolyl), 2,-(4,5-dimethyloxazolyl), 2-(4,5-dimethylimidazolyl), 2-(4,5-diethylthiazolyl), 2-(4,5-diethyloxazolyl), 2-(4,5-diethylimidazolyl), 2-(4,5-di-n-propylthiazolyl), 2-(4,5-di-n-propyloxazolyl), 2-(4,5-di-n-propylimidazolyl), 2-(4,5-di-n-butylthiazolyl), 2-(4,5-di-n-butyloxazolyl), 2-(4,5-di-n-butylimidazolyl), 2-(4,5-diphenylthiazolyl), 2-(4,5-diphenyloxazolyl), 2-(4-phenylimidazolyl), 2-(4-phenyl-5-methylthiazolyl), 2-(4-phenyl-5-methyloxazolyl), 2-(4-phenyl-5-methylimidazolyl), 2-(5-acetyl-4-methylthiazolyl), 2-(5-carbomethoxy-4-methylthiazolyl), 2-(5-carbethoxy-4-methylthiazolyl), 2-(5-carbethoxythiazolyl), 2-(5-carbamoyl-4-methylthiazolyl), 2-(5-carbanilino-4-methylthiazolyl), 2-(4-ethylbenzothiazolyl), 2-(4-ethylbenzoxazolyl), 2-(4-ethylbenzimidazolyl), 2-(5-chlorobenzothiazolyl), 2-(5-chlorobenzoxazolyl), 2-(5-chlorobenzimidazolyl), 2-(6-ethoxybenzothiazolyl), 2-(6-ethoxybenzoxazolyl), 2-(6-ethoxybenzimidazolyl), 2-(4-phenylbenzothiazolyl), 2-(4-phenylbenzoxazolyl), 2-(4-phenylbenzimidazolyl), 2-(5-carbethoxybenzothiazolyl), 2-(5-carbethoxybenzoxazolyl), 2-(5-carbethoxybenzimidazolyl), 2-(6-nitrobenzothiazolyl), 2-(6-nitrobenzoxazolyl), 2-(6-nitrobenzimidazolyl), 2-(4-methylbenzothiazolyl), 2-(4-methylbenzoxazolyl), 2-(4-methylbenzimidazolyl), 2-(5-ethylbenzothlazolyl), 2-(5-ethylbenzoxazolyl), 2-(5-ethylbenzimidazolyl), 2-(6-tert-butylbenzothiazolyl), 2-(6-tert-butylbenzoxazolyl), 2-(6-tert-butylbenzimidazolyl), 2-(4,6-dimethylbenzothiazolyl), 2-(4,6-dimethylbenzoxazolyl), 2-(4,6-dimethylbenzimidazolyl), 2-(5,6-diethylbenzothiazolyl), 2-(5,6-diethylbenzoxazolyl), 2-(5,6-diethylbenzimidazolyl), 2-(7-methylbenzothiazolyl), 2-(7-methylbenzoxazolyl), 2-(7-methylbenzimidazolyl), 2-(6-octylbenzothiazolyl), 2-(6-octylbenzoxazolyl), 2-(6-octylbenzimidazolyl), 2-(4-methylthiazolinyl), 2-(5-methylthiazolinyl), 2-(4,4-dimethylthiazolinyl), 2-(5,5-dimethylthiazolinyl), 2-(4-ethylthiazolinyl), 2-(4-butylthiazolinyl), 2-(4-methyl-5-butylthiazolinyl), 2-(4-phenylthiazolinyl), 2-(4-benzylthiazolinyl) 2-[4-(2-hydroxyethyl)-thiazolinyl], 2-(4-chloro-5-methylthiazolinyl), 2-(4-chloro-5-ethylthiazolinyl), 2-(4-hydroxythiazolinyl), 2-(4-methoxythiazolinyl), 2-(4-aminothiazolinyl), 2-(5-chlorothiazolinyl), 2-(5,5-dimethyloxazolinyl), 2-(4,5-dimethyloxazolinyl), 2-(4-ethyloxazolinyl), 2-(5-ethyloxazolinyl), 2-(4-methyloxazolinyl), 2-(4,4-dimethyloxazolinyl), 2-(4-phenyloxazolinyl), 2-(4-methoxyoxazolinyl), 2-(4-butyloxazolinyl) and 2-(5-amyloxazolinyl). Of the azole radicals, thiazolyl radicals and especially benzothiazolyl are preferred.

The characteristic moiety present in dithiocarbamates and structurally related accelerators suitable for Acc is represented by the formula

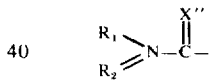

wherein $R_1$ and $R_2$ independently are hydrogen, alkyl, cycloalkyl, aralkyl, phenyl, substituted phenyl and $R_1$ and $R_2$ along with the nitrogen atom may form a heterocycle of 4–8 carbon atoms and X'' is S or O but S is much preferred and $R_1$ and $R_2$ of 1–20 carbon atoms are preferred within which group 4–20 carbon atoms are more preferred in order to minimize or eliminate surface bloom on the vulcanizate. Examples of $R_1$ and $R_2$ are methyl, ethyl, propyl, isopropyl, n-butyl, isobutyl, sec-butyl, tert-butyl, n-amyl, hexyl, octyl, decyl, dodecyl, eicosyl, cyclopentyl, cyclohexyl, cyclooctyl, phenyl, benzyl, phenethyl and tolyl.

Specific examples of thiocarbamoyl radicals of the preferred dithiocarbamates are N,N-(dimethyl)thiocarbamoyl, N,N-(diethyl)thiocarbamoyl, N,N-(di-n-propyl)thiocarbamoyl, N,N-(di-n-butyl)thiocarbamoyl, N,N-(di-hexyl)thiocarbamoyl, N,N-(di-octyl)thiocarbamoyl, N,N-(di-decyl)thiocarbamoyl, N,N-(di-dodecyl)thiocarbamoyl, N-octadecyl-N-isopropylthiocarbamoyl, N,N-(di-benzyl)thiocarbamoyl, N-ethyl-N-benzylthiocarbamoyl, N-hexyl-N-benzylthiocarbamoyl, N-methyl-N-cyclohexylthiocarbamoyl, N,N-(dicyclohexyl)thiocarbamoyl, N-methyl-N-phenylthiocarbamoyl, N-ethyl-N-phenylthiocarbamoyl, N-propyl-N-phenylthiocarbamoyl, N-benzyl-N-phenylthiocarbamoyl, N-hexyl-N-phenylthiocarbamoyl, N-methyl-N- tolylthiocarbamoyl, N-methyl-N-(2-norbornanyl)thiocarbamoyl, 1-(pyrrolidinyl)thiocarbonyl, 1-(2,5-dimethylpyrrolidinyl)thiocarbonyl, (piperidino)thiocarbonyl, 2-methylpiperidinothiocarbonyl, morpholinothiocarbonyl, 2,6-dimethylmorpholinothiocarbonyl, hexahydro-1H-azepine-1-yl thiocarbonyl, hexahydro-1-(2H)azocin-1-yl thiocarbonyl, octahydro-1H-azonin-1-ylthiocarbonyl and azabicyclo[3.2.2]non-3-ylthiocarbonyl.

Illustrative phosphorus radicals which are suitable for Acc are residues obtained from a phosphorodithioate accelerator which residues may be represented by the formula

wherein $R_3$ and $R_4$ independently are alkyl, cycloalkyl, aralkyl, phenyl and alkyl substituted phenyl. Examples of $R_3$ and $R_4$ are methyl, ethyl, propyl, isopropyl, n-butyl, isobutyl, sec-butyl, tert-butyl, n-amyl, hexyl, octyl, decyl, dodecyl, eicosyl, cyclopentyl, cyclohexyl, cyclooctyl, phenyl, benzyl, phenethyl and tolyl. Each of $R_3$ and $R_4$ will usually contain 1–20 carbon atoms and alkyl radicals of 1–6 carbon atoms comprise a preferred subgroup.

The characteristic moiety present in xanthate and structurally related accelerators suitable for Acc is represented by the formula

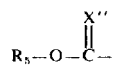

wherein $R_5$ preferably contains –20 carbon atoms and is alkyl, cycloalkyl, aralkyl, phenyl and alkyl substituted phenyl and X'' is S or O, preferably S. Examples of $R_5$ are methyl, ethyl, propyl, isopropyl, n-butyl, isobutyl, sec-butyl, tert-butyl, n-amyl, hexyl, octyl, decyl, dodecyl, eicosyl, cyclopentyl, cyclohexyl, cyclooctyl, phenyl, benzyl, phenethyl and tolyl.

There are of course other classes of thio accelerators well known to the art. Merely by way of illustration, other Acc radicals along with the sulfur atom to which they are attached which may be mentioned as suitable accelerator moieties in the new cross-linking agents are 2-pyrimidinylthio, 2-(4,6-dimethyl-pyrimidinylthio), 2-(4,4,6-trimethyl-dihydropyrimidinylthio), 2-tetrahydropyrimidinylthio, 4-benzopyrimidinylthio, 4-(2,6-dimethyl-pyrimidinylthio), 4-(6-methoxypyrimidinylthio), 4-(6-methyl-2-methylthiopyrimidinylthio), 4-(5-methoxy-pyrimidinylthio), 2-(4-methyl-6-phenyl-pyrimidinylthio), 2-(4-methyl-pyrimidinylthio), 2-(4-methylthio-pyrimidinylthio), 2-(5-nitro-pyrimidinylthio), 2-(4-methylaminopyrimidinylthio), 2-(6-methylamino-pyrimidinylthio), 2-(4-morpholino-pyrimidinylthio), 4-quinazolinylthio, dithiole-3-thione-5-ylthio, 2-[4,6-bis(ethylamino)]-s-triazinylthio, 2-[4,6-bis(isopropylamino)]-s-triazinylthio, 2-(4-ethylamino-6-diethylamino)-s-triazinylthio, 2-[4,6-bis(phenyl)]-s-triazinylthio, 2-(4-chloro-6-phenyl)-s-triazinylthio, 2,4-dinitrophenylthio, 2-nitrophenylthio, 2-chloro-4-nitrophenylthio, 2-(5-acetamido-1,3,4-thiadiazolylthio), 2-(4-phenyl-5-thioxo-1,3,4-thiadiazolylthio), 5-(3-bromo-1,2,4-thiadiazolylthio), 5-(3-chloro-1,2,4-thiadiazolylthio), 2-pyridinylthio, N-)dialkylamino)thiocarbamoylthio (derived from, e.g., 1,1-dimethyldithiocarbazinic acid) and 2-quinolinylthio.

Suitable accelerator moieties where Acc-S— is pyrimidinylthio will perhaps be better understood from the formulas

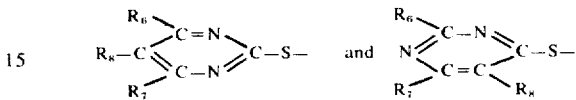

wherein $R_6$, $R_7$ and $R_8$ independently are hydrogen, lower alkyl, lower alkoxy, phenyl, nitro, chloro, lower alkylthio, lower alkylamino, lower dialkylamino, heterocyclic amino or $R_7$ and $R_8$ together with the adjacent carbon atoms to which they are attached form ortho arylene. The corresponding dihydro or tetrahydro pyrimidinylthio radicals may be used where desired.

Similarly, the s-triazinylthio radicals may be represented by the formula

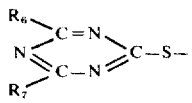

wherein $R_6$ and $R_7$ are independent and independently have the same meaning as before.

Formulas representative of thiadiazolylthio radicals in the cross-linking agents are

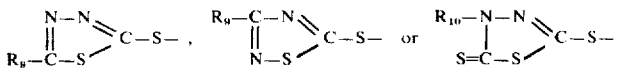

wherein $R_9$ is acetamido, lower alkyl, phenyl, chloro or bromo, and $R_{10}$ is lower alkyl or phenyl.

The dithiole-3-thione-5-ylthio radical refers to the formula

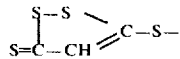

Typical aminodithiocarbamoyl radicals have the formula

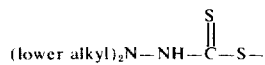

Representative pyridinylthio AccS radicals have the formula

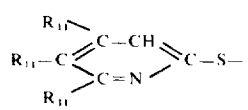

wherein each $R_{11}$ independently is hydrogen or lower alkyl. The 2-quinolinylthio radical has the formula

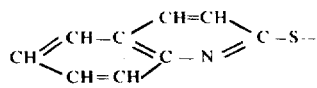

AccS- derived from nitrothiophenol accelerators are nitrophenylthio radicals of the formula

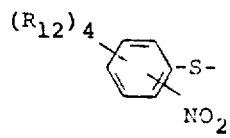

wherein independently each $R_{12}$ is hydrogen, alkyl, chloro, nitro, carboalkoxy, carboxy or acetyl. Carbomethoxy and carboethoxy are desirable carboalkoxy radicals but dinitrophenyl is preferred.

The organic bridging group R which joins two or more accelerator moieties through one or more sulfur atoms includes di-, tri- and tetravalent radicals, preferably hydrocarbon, in which each valence is attached to a carbon atom. The bridging group will generally contain 1 to 24 carbon atoms within which groups of 2 to 12 carbon atoms are preferred. Still more preferred groups are those having 2 to 8 carbon atoms except that some cross-linking agents where R is 1 to 4 carbon atoms produce vulcanizates having distinctive odor but usually no significant odor is noticed from use of cross-linking agent wherein R contains more than four carbon atoms. Whether R is acyclic or cyclic the chain may be interrupted by atoms other than carbon, especially oxygen or sulfur. Similarly, suitable R groups comprise two or more arylene radicals joined by sulfur or oxygen. Also, hybrid bridging groups having one valence to sulfur from an acyclic carbon atom and another from a cyclic carbon atom either aromatic or alicyclic are entirely feasible. It will be understood that arylene includes substituted radicals which substituents may be lower alkyl, lower alkoxy, nitro, halogen or combination thereof, the term "lower" designating 1 to 5 carbon atoms.

One subclass of valuable bridging groups are hydrocarbon radicals which are alkylene or alkylidene of the series $C_nH_{2n}$ and substituted derivatives thereof. The chains may be straight or branched and any branching groups may be attached to a terminal carbon atom or attached to a carbon atom within the chain or both. The aforesaid subclass may be designated by the formula $(X)_{n'}$ where $n'$ is 1 to 24, each X is the same or different and is

where Z and Z' independently are hydrogen, alkyl, cycloalkyl, benzyl or phenyl. Where $n'$ is one and at least one of Z and Z' is not hydrogen, the radicals are alkylidene radicals. Where both Z and Z' are hydrogen in all units present, straight chain alkylene radicals are defined. Illustrative of R when $C_nH_{2n}$ are divalent radicals derived by removal of two hydrogen atoms from methane, ethane, propane, butane, isobutane, pentane, hexane, heptane and octane.

Another subclass is represented by divalent radicals where both valences are on carbon atoms of the type defined by X supra but the chain is interrupted or substituted in a different manner than described above. This subclass may be represented by the formula

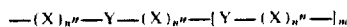

where each $n''$ independently is 1 to 23, $m$ is 0, 1 or 2, X has the same meaning as before and Y is oxygen, sulfur, $-SO_2-$, HN<, $C_6H_5N<$, lower alkyl-N<, $-C(O)O-$, divalent aliphatic cyclic or arylene. Illustrative preferred examples are radicals derived by removal of two hydrogen atoms from each methyl of xylene (phenylenedimethylene).

R also comprises divalent aliphatic cyclic and arylene per se. Thus, a third subclass are divalent cyclic radicals each valence of which is on a carbon atom of an aliphatic ring, said radicals being the residue from removal of hydrogen from carbon is monocyclic, bicyclic or tricyclic hydrocarbon or from said hydrocarbon having up to two ring carbon atoms replaced by oxygen, or from bi(monocyclic hydrocarbon) in which case hydrogen is removed from carbon in two separate monocyclic hydrocarbons joined directly or joined through alkylene or alkenylene not to be confused with the fused ring hydrocarbons. Divalent cyclic radicals preferably contain 5 to 15 ring members and comprise cycloalkylene (saturated monocyclic divalent), cycloalkylidene (two valences on the same carbon), bicycloalkylene, tricycloalkylene (divalent fused rings), bi(monocyclic), such as $-C_6H_{10}-C_6H_{10}-$ (bicyclohexylene), which has the valences on separate cyclic radicals, fused ring radicals having the two valences on the same carbon (bicycloalkylidene and tricycloalkylidene), cycloalkenylene (divalent alicyclic containing unsaturation) and cycloalkenylidene. Illustrative of R when divalent cyclic are radicals derived by removal of two hydrogen atoms from cyclopentane, cyclohexane, cycloheptane, cyclooctane and cyclododecane.

Unsaturated acyclic divalent radicals are suitable bridging groups which subclass are alkylene and alkylidene radicals of the series $C_nH_{2n-2}$ and $C_nH_{2n-4}$ (diene radicals).

A wide variety of divalent aromatic radicals are desirable bridging groups which subclass comprise anthrylene and radicals derived by removal of hydrogen from two ring carbon atoms of a compound of the formula

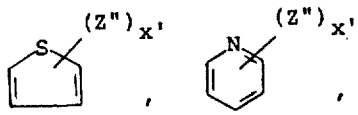

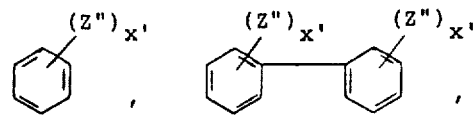

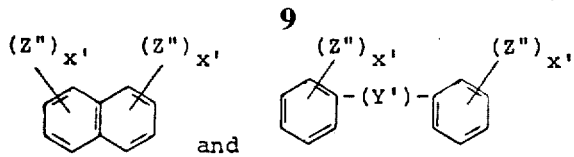

where each Z'' independently is hydrogen, lower alkyl, hydroxy, lower alkoxy, acetyl, phenyl, chloro or nitro, Y' is oxygen, sulfur, —SO$_2$—, —CO—, lower alkylene or lower alkylidene, $x'$ is 1 to 4. In the thiophene, pyridine and benzene rings, $x'$ is 2, 3 and 4, respectively. In the naphthidene ring one $x'$ is 2 to 4 depending upon whether or not the two valence bonds are in one ring, the sum of the two $x'$s being 6. Similarly, where two benzene rings are connected, $x'$ is 3 or 4 depending upon the position of the two valence bonds and the sum of the two $x'$s is 8. Of the arylene subclass unsubstituted radicals or radicals having only one electronegative substituent are preferred.

Further valuable bridging groups are derived from combinations of the aforesaid radicals which combination may be designated as —T-T'— where T is selected from one of the aforesaid subclasses and T' is selected from a different member of the aforesaid subclasses and where the free valence of T is linked to cyclic carbon and the free valence of T' is linked to acyclic carbon.

Oxygen substituted bridging groups are represented by straight and branched chain alkylene substituted by one or more oxo, hydroxy, alkoxy, hydroxyalkoxy, alkoxyalkoxy, carboxy, carboxyalkoxy, carboalkoxy or acetoxy substituents. In place of acetoxy other

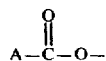

substituents where A is lower alkyl herein referred to as acyloxy may be present.

Suitable trivalent radicals are derived by removal of one hydrogen from any of the aforesaid divalent radicals, for example

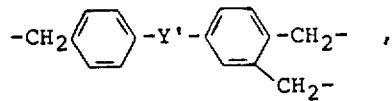

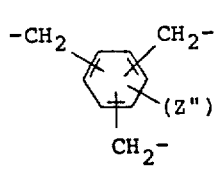

where Y', Z'' and $x'$ have the same meaning as before. Suitable trivalent radicals also include those of the formula

where A' independently is lower alkylene and radicals of the formula

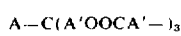

where A is lower alkyl and A' independently is lower alkylene.

Suitable tetravalent radicals are derived by removal of two hydrogen atoms from any of the aforesaid divalent radicals, for example, C(-A'-)$_4$ where A' is lower alkylene which may be regarded as derived from branched chain alkylene, O(-A''=)$_2$ where A'' is 1,2,3-propanetriyl or other lower alkanetriyl, which radicals may be regarded as derived from interrupted chain divalent radical where (X)$_n$ is lower alkylene, Y is oxygen and $m$ is zero and A'(OA''=)$_2$ where A' is lower alkylene and A'' is lower alkanetriyl which may be regarded as derived from interrupted chain divalent radical where (X)$_n$ is lower alkylene, Y is oxygen and $m$ is one. Still other suitable tetravalent radicals are represented by the formulas

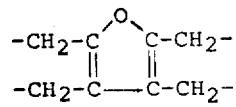

and C(A'OOCA'—)$_4$ where A' independently is lower alkylene.

The nature and variety of the bridging group will be further explained by reference to polythiols useful for making the cross-linking agents. R groups when $n$ is 2 are the residues from removing two -SH radicals from dithiols. Dithiols useful as intermediates in the preparation of the compounds of this invention are 1,1-methanedithiol, 1,2-ethanedithiol, phenyl-1,2-ethanedithiol, 1,3-propanedithiol, 2,2-propanedithiol, 1,2-propanedithiol, 2,2-dimethyl-1,3-propanedithiol, 2-sec-butyl-2-methyl-1,3-propanedithiol, 1,3-diphenyl-2,2-propanedithiol, 1,4-butanedithiol, 2,3-butanedithiol, 2,2-butanedithiol, 1,3-isobutanedithiol, 1,5-pentanedithiol, 1,6-hexanedithiol, 1,2-hexanedithiol, 2-ethyl-1,6-hexanedithiol, 2,5-dimethyl-3,4-hexanedithiol, 2,5-dimethyl-2,4-hexanedithiol, 2-ethyl-1,3-hexanedithiol, 3,5,5-trimethyl-1,1-hexanedithiol, 1,7-heptanedithiol, 1,8-octanedithiol, 1,2-octanedithiol, 2,6-dimethyl-3,7-octanedithiol, 2,6-dimethyl-2,6-octanedithiol, 1,9-nonanedithiol, 1,10-decanedithiol, 1,12-dodecanedithiol, 1,2-diphenyl-1,2-ethanedithiol, 7,8-pentadecanedithiol, 1,10-octadecanedithiol, 1,12-octadecanedithiol, 1,2-hexadecanedithiol, 1,2-octadecanedithiol, 1,18-octadecanedithiol, 1,11-undecanedithiol and 12,12-tricosanedithiol.

4,8-Dithiaundecane-1,11-dithiol, 4,6-dithianonane-1,9-dithiol, 4,7-dithiadecane-1,10-dithiol, 2,2'-oxydiethanedithiol, 2,2'-thiodiethanethiol, 3,3'-thiodipropanethiol, 4,4'-oxydibutane-1-thiol, 4,4'-oxydipentane-1-thiol, 3,3'-oxetanedimethanethiol, 2,2'-(ethylenedithio)diethanethiol (HSC$_2$H$_4$SC$_2$H$_4$SCH$_2$H$_4$SH), 1,1'-cyclohexanedimethanethiol, 1,2-cyclohexanedimethanethiol, 1,4-cyclohexanedimethanethiol, 1,2-bis(3-mercaptocyclohexyl)ethylene, 1,2-bis(4-mercaptocyclohexyl)ethylene, p-benzenediethanethiol, α,α'-p-xylenedithiol, 2,5-dimethyl-α,α'-p-xylenedithiol, 2,3,5,6-tetramethyl-α,α'-p-xylenedithiol, α,α'-dimethyl-α,α'-xylenedithiol and 9,10-anthracenedimethanethiol.

2,2-Camphanedithiol, (1,7,7-trimethyl-2,2-dimercaptobicyclo[2.2.1]heptane), (2,5-mercaptobicyclo[2.2.1]heptane), 2,5-norbornanedithiol, 2,6-norbornanedithiol, 2-mercapto-5-(mercaptomethyl)norbornane, 2-mercapto-5-(2'-mercaptoethyl)norbornane, 4-mercaptocyclohexaneethanethiol, 2-mercaptocyclohexaneethanethiol, 3-mercaptocyclohexaneethanethiol, 2,2,4,4-tetramethyl-1,3-cyclobutanedithiol, 1,1-cyclopentanedithiol, 1,2-cyclopentanedithiol, 1,1-cyclohexanedithiol, 1,2-cyclohexanedithiol, 4-cyclohexene-1,2-dithiol, p-dioxane-2,3-dithiol, 1,2-cyclooctanedithiol, p-menthane-2,9-dithiol, 1,1-cycloheptanedithiol, 2-methyl-1,1-cyclohexanedithiol, 4-tert-butyl-1,1-cyclohexanedithiol, 1,1-cyclododecanedithiol, 1,1-cyclopentadecanedithiol and dimercapto derivative of dicyclopentadiene. 2,6-Pyridinedithiol, 3,4-thiophenedithiol, 2,3-thiophenedithiol, 2,5-thiophenedithiol, o-benzenedithiol, m-benzenedithiol, 4-ethoxy-o-benzenedithiol, 5-nitro-m-benzenedithiol, 4,5-dimethyl-o-benzenedithiol, p-benzenedithiol, 4,5-dimethyl-m-benzenedithiol, 2,4-dimethyl-m-benzenedithiol, 4-ethyl-m-benzenedithiol, 2,5-dichloro-m-benzenedithiol, nitro-p-benzenedithiol, 4,4'-methylenedibenzenethiol, 4,4'-ethylenedibenzenethiol, 4,4'-ethylidenedibenzenethiol, 4,4'-isopropylidenedibenzenethiol, 4,4'-biphenyldimethanethiol, 1,4-bis(mercaptomethyl)naphthalene, 5,8-bis(-mercaptomethyl)tetrahydronaphthalene, 2,4-di(mercaptomethyl)-anisole, 1,4-bis(mercaptomethyl)-2,5-dimethoxybenzene, tetrachloro-1,4-bis(mercaptomethyl)benzene, 1,4-naphthalenedithiol, 1,5-naphthalenedithiol, 2,6-naphthalenedithiol, 2,7-naphthalenedithiol, 1,2,3,4-tetrahydro-2,3-naphthalenedithiol, 2,5-toluenedithiol, dimercapto-o-, m or p-cresol, 5-methoxy-2,4-toluenedithiol, 3,4-toluenedithiol, 2,2'-biphenyldithiol, 4,4'-biphenyldithiol, 3,3'-dimethyl-4,4'-biphenyldithiol, 4,4'-oxybisbbenzenethiol, 4,4'-sulfonyldibenzenethiol, 4,4'-dithiobenzophenone, 2,4-dimercaptoacetophenone and 3,5-dimercaptoacetophenone.

Glycol dimercaptoacetate [$C_2H_4(OOCCH_2-SH)_2$], isopropylene glycol dimercaptoacetate [$HSCH_2COOCH_2CH(CH_3)OOCCH_2SH$], glycol dimercaptopropionate [$C_2H_4(OOCCH_2CH_2-SH)_2$], $HSC_2H_4SO_2C_2H_4SH$, $HSC_2H_4N(CH_3)C_2H_4SH$, $HSCH_2CH_2N(C_2H_5)CH_2CH_2SH$, $HSCH_2CH_2N(C_6H_5)CH_2CH_2SH$, $C_4H_9N[CH(CH_3)CH_2SH]_2$, ethene-1,2-dithiol, 2-butene-1,4-dithiol, hexene-1,6-dithiol, 1,3-butadiene-1,4-dithiol, 2,6-octadiene-1,8-dithiol, 8-cyclododecene-1,4-dithiol, 8-cyclododecene-1,5-dithiol and 9-cyclododecene-1,6-dithiol.

Valuable cross-linking agents are derived from polythiols wherein the residue corresponding to R contains a carboxy, ester, hydroxy, ether or keto substituent. Acid substituents, for example, modify and extend the cross-linking reaction through reactivity with metal oxides. The synthesis and properties of polythiols which serve as intermediates for cross-linking agents are described by Reid, Organic Chemistry of Bivalent Sulfur, Vol. 1 Chemical Publishing Company, 1958. Others have since appeared in the literature. Examples of polythiol intermediates representative of suitable oxygen substituted bridging groups are 1,3-dimercapto-2-propanol, 2,3-dimercapto-1-propanol, 1,3-dimercapto-2-methyl-2-propanol, 2,3-, 2,4- or 3,4-dimercapto-1-butanol, 1,3-, 1,4- or 3,4-dimercapto-2-butanol, 1,4-dimercaptobutanediol-2,3, 2,5- or 4,5-dimercapto-1-pentanol, 1,2-dimercaptopentanetriol-3,4,5,1,6-dimercapto-2-hexanol, 2,11-dimercapto-1-undecanol, 1,4-dimercapto-2,3-butanediol, 2,3-dimercapto-1,4-butanediol, and dithioerythritol.

2,6-Dimercapto hexanoic acid, 2,5-bis(3-mercaptopropyl)hexanoic acid, 5,7-dimercapto heptanoic acid, 2,6- or 6,8-dimercapto octanoic acid, 4 or 7 methyl 6,8-dimercapto octanoic acid, 6,8-dimercapto nonanoic acid, 2,3-dimercapto succinic acid, 2,4-dimercapto glutaric acid, 2,5-dimercapto hexanedioic acid, 2,6-dimercapto heptanedioic acid, and 2,7-dimercapto octanedioic acid.

3-Lower alkoxy-1,2-propanedithiol, (2,3-dimercaptopropoxy-ethanol, (2,3-dimercaptopropoxy)-2-propanol, 3-(dimethoxyethyl)-1,2-propanedithiol, 3-(2,3-dimercaptopropoxy)-1,2-propanediol, 1-(2,3-dimercaptopropoxy)-3-methoxy-2-propanol, 2,3-dimercapto-1-propanol acetate, 4,5-dimercapto-1-pentanol acetate, 2,3-dimercapto-1,4-butanediol diacetate, 1,2-dimercapto-6,7-dihydroxy-4-oxaheptane, 1,2-dimercapto-6,7-dimethoxy-4-oxaheptane, 1,2-dimercapto-5-hydroxymethyl-6-hydroxy-4-oxahexane, 1,2-dimercapto-3-hydroxy-4-methoxybutane and 1,2-dimercapto-3,4,5-trimethoxypentane.

2,3-Dimercapto propanoic acid methyl ester, 2,3-dimercapto propanoic acid, 2,6-dimercapto hexanoic acid ethyl ester, 6,8-dimercapto octanoic acid, 6,8-dimercapto octanoic acid methyl ester, 6,8-dimercapto octanoic acid ethyl ester, 2,3-dimercapto succinic acid, dimethyl, diethyl and dipropyl esters of 2,3-dimercapto succinic acid, 2,3-dimercaptopropyl malonic acid diethyl ester, $\alpha$-(2,3-dimercaptopropyl)-$\alpha$-(lower alkyl)-malonic acid diethyl ester, $\alpha$-(2,3-dimercaptopropyl)-$\alpha$-(2,3-dihydroxypropyl)malonic acid diethyl ester, $\alpha$-(2,3-dimercaptopropyl)-$\alpha$-(3-mercaptopropyl) malonic acid diethyl ester, 3,3-dimercapto hexanoic acid ethyl ester, 3,3-dimercaptobutyric acid ethyl ester, 3,3-dimercapto-2-ethyl butyric acid ethyl ester, 3,3-dimercapto-2-methyl butyric acid ethyl ester, 3,3-dimercapto valeric acid ethyl ester, 2-(1,1-dimercaptoethyl)-valeric acid ethyl ester, 10,11-dimercapto undecanoic acid, 2,3-dimercaptopropoxyacetic acid ($HSCH_2CH(SH)CH_2OCH_2COOH$), $\beta,\beta'$-dimercaptoisobutyric acid and $\beta,\beta'$-dimercaptoacetone.

Trithiols and tetrathiols are of course selected as intermediates when it is desired that $n$ of the general formula of cross-linking agents be 3 or 4. Illustrative examples are 1,2,3-propanetrithiol, 1,2,3-benzenetrithiol, 1,3,5-benzenetrithiol, trimercapto-m-cresol, 2,4,6-trimercapto phenol, 2,4,6-trimethyl-1,3,5-benzenetrithiol, 1,2,3,4-butanetetrathiol, neopentanetetrathiol, 1,5,10-decanetrithiol, tri(2-mercaptoethyl)amine, 4-mercaptomethylphenyl-3',4'-(dimercaptomethyl)phenyloxide, 2,2-[4-mercaptomethylphenyl-3',4'-(dimercaptomethyl)phenyl]propane, 4-mercaptomethylphenyl-3',4'-(dimercaptomethyl)phenyl sulphone, 1,3,5-tri(mercaptomethyl)-4-methyl benzene, 2,3,4,5-tetra(mercaptomethyl)furan, trimethylolethanetri(3-mercaptopropionate), ($CH_3C(CH_2OOCCH_2-CH_2-SH)_3$), trimethylolethanetrithioglycolate, ($CH_3C(CH_2OOCCH_2-SH)_3$), trimethylolpropanetri(3-mercaptopropionate), ($CH_3CH_2C(CH_2OOCCH_2CH_2-SH)_3$), trimethylolpropanetri(thioglycolate), ($CH_3CH_2C(CH_2OOCCH_2-SH)_3$), pentaerythritol tetra(3-mercaptopropionate), ($C(CH_2OOCCH_2CH_2-SH)_4$), pentaerythritol tetrathioglycolate, ($C(CH_2OOCCH_2-SH)_4$),

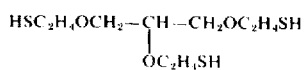

and 3,3'-oxydi-1,2-propanedithiol.

Suitable poly(oxydialkylene)thiols are described in U.S. Pat. No. 2,919,262 Nummy, Dec. 29, 1959, which is incorporated herein by reference. Examples of other suitable polythiols are described in U.S. Pat. Nos. 3,384,671 Louthan May 21, 1968; 3,522,313 Reece et al. July 28, 1970; 3,534,108 Audouze Oct. 13, 1970; and in German Pat. Nos. 2,004,304 published Aug. 6, 1970; 2,004,306 published Aug. 6, 1970; and 2,004,307 published Aug. 6, 1970.

The following compounds are illustrative of cross-linking agents which are suitable in the practice of this invention.

1,1-bis(N,N-dimethylthiocarbamoyldithio)methane
1,2-bis-(N,N-dimethylthiocarbamoyldithio)ethane
1,3-bis(N,N-dimethylthiocarbamoyldithio)propane
1,4-bis(N,N-dimethylthiocarbamoyldithio)butane
1,6-bis(N,N-dimethylthiocarbamoyldithio)hexane
1,8-bis(N,N-dimethylthiocarbamoyldithio)octane
1,10-bis(N,N-dimethylthiocarbamoyldithio)decane
1,10-bis(N,N-dimethylthiocarbamoyldithio)octadecane
1,18-bis(N,N-dimethylthiocarbamoyldithio)octadecane
2,2'-bis(N,N-dimethylthiocarbamoyldithio)oxydiethane
2,2'-bis(N,N-dimethylthiocarbamoyldithio)thiodiethane
4,4'-bis(N,N-dimethylthiocarbamoyldithio)oxydibutane
1,1'-bis(N,N-dimethylthiocarbamoyldithio)-4-cyclohexanedimethane
1,4-bis(N,N-dimethylthiocarbamoyldithio)benzene
α,α'-bis(N,N-dimethylthiocarbamoyldithio)-p-xylene
1,2-bis(N,N-dimethylthiocarbamoyldithio)cyclohexane
1,1-bis(N,N-dimethylthiocarbamoyldithio)cyclohexane
2,9-di(N,N-dimethylthiocarbamoyldithio)-p-menthane
1,4-bis(N,N-dimethylthiocarbamoyldithio)naphthalene
2,5-di(N,N-dimethylthiocarbamoyldithio)toluene
4,4'-bis(N,N-dimethylthiocarbamoyldithio)biphenyl
4,4'-bis(N,N-dimethylthiocarbamoyldithio)oxybisbenzene
bis(N,N-dimethylthiocarbamoyldithio)glycolacetate
bis(N,N-dimethylthiocarbamoyldithio)glycolpropionate
1,2,3-tri(N,N-dimethylthiocarbamoyldithio)propane
1,3,5-tri-(N,N-dimethylthiocarbamoyldithio)benzene
tetra(N,N-dimethylthiocarbamoyldithio)neopentane
tetra(N,N-dimethylthiocarbamoyldithio)pentaerythritol glycolate
1,1-bis(N,N-diethylthiocarbamoyldithio)methane
1,2-bis(N,N-diethylthiocarbamoyldithio)ethane
1,3-bis(N,N-diethylthiocarbamoyldithio)propane
1,4-bis(N,N-diethylthiocarbamoyldithio)butane
1,6-bis(N,N-diethylthiocarbamoyldithio)hexane
1,8-bis(N,N-diethylthiocarbamoyldithio)octane
1,10-bis(N,N-diethylthiocarbamoyldithio)decane
1,10-bis(N,N-diethylthiocarbamoyldithio)octadecane
1,18-bis(N,N-diethylthiocarbamoyldithio)octadecane
2,2'-bis(N,N-diethylthiocarbamoyldithio)oxydiethane
2,2'-bis(N,N-diethylthiocarbamoyldithio)thiodiethane
4,4'-bis(N,N-diethylthiocarbamoyldithio)oxydibutane
1,1'-bis(N,N-diethylthiocarbamoyldithio)-1,4-cyclohexanedimethane
1,4-bis(N,N-diethylthiocarbamoyldithio)benzene
α,α'-bis(N,N-diethylthiocarbamoyldithio)-p-xylene
1,2-bis(N,N-diethylthiocarbamoyldithio)cyclohexane
1,1-bis(N,N-diethylthiocarbamoyldithio)cyclohexane
2,9-di(N,N-diethylthiocarbamoyldithio)-p-menthane
1,4-bis(N,N-diethylthiocarbamoyldithio)naphthalene
2,5-di(N,N-diethylthiocarbamoyldithio)toluene
4,4'-bis(N,N-diethylthiocarbamoyldithio)biphenyl
4,4'-bis(N,N-diethylthiocarbamoyldithio)oxybisbenzene
bis(N,N-diethylthiocarbamoyldithio)glycolacetate
bis(N,N-diethylthiocarbamoyldithio)glycol propionate
1,2,3-tri(N,N-diethylthiocarbamoyldithio)propane
1,3,5-tri(N,N-diethylthiocarbamoyldithio)benzene
tetra(N,N-diethylthiocarbamoyldithio)neopentane
tetra(N,N-diethylthiocarbamoyldithio)pentaerythritol glycolate
1,1-bis(N,N-di-n-butylthiocarbamoyldithio)methane
1,2-bis(N,N-di-n-butylthiocarbamoyldithio)ethane
1,3-bis(N,N-di-n-butylthiocarbamoyldithio)propane
1,4-bis(N,N-di-n-butylthiocarbamoyldithio)butane
1,6-bis(N,N-di-n-butylthiocarbamoyldithio)hexane
1,8-bis(N,N-di-n-butylthiocarbamoyldithio)octane
1,10-bis(N,N-di-n-butylthiocarbamoyldithio)decane
1,10-bis(N,N-di-n-butylthiocarbamoyldithio)octadecane
1,18-bis(N,N-di-n-butylthiocarbamoyldithio)octadecane
2,2'-bis(N,N-di-n-butylthiocarbamoyldithio)oxydiethane
2,2'-bis(N,N-di-n-butylthiocarbamoyldithio)thiodiethane
4,4'-bis(N,N-di-n-butylthiocarbamoyldithio)oxydibutane
1,1'-bis(N,N-di-n-butylthiocarbamoyldithio)-1,4-cyclohexanedimethane
1,4-bis(N,N-di-n-butylthiocarbamoyldithio)benzene
α,α'-bis(N,N-di-n-butylthiocarbamoyldithio)-p-xylene
1,2-bis(N,N-di-n-butylthiocarbamoyldithio)cyclohexane
1,1-bis(N,N-di-n-butylthiocarbamoyldithio)cyclohexane
2,9-di(N,N-di-n-butylthiocarbamoyldithio)-p-menthane
1,4-bis(N,N-di-n-butylthiocarbamoyldithio)naphthalene
2,5-di(N,N-di-n-butylthiocarbamoyldithio)toluene
4,4'-bis(N,N-di-n-butylthiocarbamoyldithio)biphenyl
4,4'-bis(N,N-di-n-butylthiocarbamoyldithio)oxybisbenzene
bis(N,N-di-n-butylthiocarbamoyldithio)glycolacetate
bis(N,N-di-n-butylthiocarbamoyldithio)glycol propionate
1,2,3-tri(N,N-di-n-butylthiocarbamoyldithio)propane
1,3,5-tri(N,N-di-n-butylthiocarbamoyldithio)benzene
tetra(N,N-di-n-butylthiocarbamoyldithio)neopentane
tetra(N,N-di-n-butylthiocarbamoyldithio)pentaerythritol glycolate
1,1-bis(N-cyclohexyl-N-propylthiocarbamoyldithio)methane
1,2-bis(N-cyclohexyl-N-propylthiocarbamoyldithio)ethane
1,3-bis(N-cyclohexyl-N-propylthiocarbamoyldithio)propane
1,4-bis(N-cyclohexyl-N-propylthiocarbamoyldithio)butane
1,6-bis(N-cyclohexyl-N-propylthiocarbamoyldithio)hexane
1,8-bis(N-cyclohexyl-N-propylthiocarbamoyldithio)octane 1,10-bis(N-cyclohexyl-N-propylthiocarbamoyldithio)decane
1,10-bis(N-cyclohexyl-N-propylthiocarbamoyldithio)octadecane
1,18-bis(N-cyclohexyl-N-propylthiocarbamoyldithio)octadecane
2,2'-bis(N-cyclohexyl-N-propylthiocarbamoyldithio)oxydiethane
2,2'-bis(N-cyclohexyl-N-propylthiocarbamoyldithio)thiodiethane
4,4'-bis(N-cyclohexyl-N-propylthiocarbamoyldithio)oxydibutane
1,1'-bis(N-cyclohexyl-N-propylthiocarbamoyldithio)-1,4-cyclohexanedimethane
1,4-bis(N-cyclohexyl-N-propylthiocarbamoyldithio)benzene
α,α'-bis(N-cyclohexyl-N-propylthiocarbamoyldithio)-p-xylene
1,2-bis(N-cyclohexyl-N-propylthiocarbamoyldithio)cyclohexane
1,1-bis(N-cyclohexyl-N-propylthiocarbamoyldithio)cyclohexane
2,9-di(N-cyclohexyl-N-propylthiocarbamoyldithio)-p-menthane
1,4-bis(N-cyclohexyl-N-propylthiocarbamoyldithio)naphthalene
2,5-di(N-cyclohexyl-N-propylthiocarbamoyldithio)toluene
4,4'-bis(N-cyclohexyl-N-propylthiocarbamoyldithio)biphenyl
4,4'-bis(N-cyclohexyl-N-propylthiocarbamoyldithio)oxybisbenzene
bis(N-cyclohexyl-N-propylthiocarbamoyldithio)glycolacetate
bis(N-cyclohexyl-N-propylthiocarbamoyldithio)glycol propionate
1,2,3-tri(N-cyclohexyl-N-propylthiocarbamoyldithio)propane
1,3,5-tri(N-cyclohexyl-N-propylthiocarbamoyldithio)benzene
tetra(N-cyclohexyl-N-propylthiocarbamoyldithio)neopentane
tetra(N-cyclohexyl-N-propylthiocarbamoyldithio)pentaerythritol glycolate
1,1-bis(morpholinothiocarbonyldithio)methane
1,2-bis(morpholinothiocarbonyldithio)ethane
1,3-bis(morpholinothiocarbonyldithio)propane
1,4-bis(morpholinothiocarbonyldithio)butane
1,6-bis(morpholinothiocarbonyldithio)hexane
1,8-bis(morpholinothiocarbonyldithio)octane
1,10-bis(morpholinothiocarbonyldithio)decane
1,10-bis(morpholinothiocarbonyldithio)octadecane
1,18-bis(morpholinothiocarbonyldithio)octadecane
2,2'-bis(morpholinothiocarbonyldithio)oxydiethane
2,2'-bis(morpholinothiocarbonyldithio)thiodiethane
4,4'-bis(morpholinothiocarbonyldithio)oxydibutane
1,1'-bis(morpholinothiocarbonyldithio)-1,4-cyclohexanedimethane
1,4-bis(morpholinothiocarbonyldithio)benzene
α,α'-bis(morpholinothiocarbonyldithio-p-xylene
1,2-bis(morpholinothiocarbonyldithio)cyclohexane
1,1-bis(morpholinothiocarbonyldithio)cyclohexane
2,9-di(morpholinothiocarbonyldithio)-p-menthane
1,4-bis(morpholinothiocarbonyldithio)naphthalene
2,5-di(morpholinothiocarbonyldithio)toluene
4,4'-bis(morpholinothiocarbonyldithio)biphenyl
4,4'-bis(morpholinothiocarbonyldithio)oxybisbenzene
bis(morpholinothiocarbonyldithio)glycolacetate
bis(morpholinothiocarbonyldithio)glycol propionate
1,2,3-tri(morpholinothiocarbonyldithio)propane
1,3,5-tri(morpholinothiocarbonyldithio)benzene
tetra(morpholinothiocarbonyldithio)neopentane
tetra(morpholinothiocarbonyldithio)pentaerythritol glycolate
1,1'-bis(piperidinothiocarbonyldithio)methane
1,2-bis(piperidinothiocarbonyldithio)ethane
1,3-bis(piperidinothiocarbonyldithio)propane
1,4-bis(piperidinothiocarbonyldithio)butane
1,6-bis(piperidinothiocarbonyldithio)hexane
1,8-bis(piperidinothiocarbonyldithio)octane
1,10-bis(piperidinothiocarbonyldithio)decane
1,10-bis(piperidinothiocarbonyldithio)octadecane
1,18-bis(piperidinothiocarbonyldithio)octadecane
2,2'-bis(piperidinothiocarbonyldithio)oxydiethane
2,2'-bis(piperidinothiocarbonyldithio)thiodiethane
4,4'-bis(piperidinothiocarbonyldithio)oxydibutane
1,1'-bis(piperidinothiocarbonyldithio)-1,4-cyclohexanedimethane
1,4-bis(piperidinothiocarbonyldithio)benzene
α,α'-bis(piperidinothiocarbonyldithio)-p-xylene
1,2-bis(piperidinothiocarbonyldithio)cyclohexane
1,1-bis(piperidinothiocarbonyldithio)cyclohexane
2,9-di(piperidinothiocarbonyldithio)-p-methane
1,4-bis(piperidinothiocarbonyldithio)naphthalene
2,5-di(piperidinothiocarbonyldithio)toluene
4,4'-bis(piperidinothiocarbonyldithio)biphenyl
4,4'-bis(piperidinothiocarbonyldithio)oxybisbenzene
bis(piperidinothiocarbonyldithio)glycolacetate
bis(piperidinothiocarbonyldithio)glycol propionate
1,2,3-tri(piperidinothiocarbonyldithio)propane
1,3,5-tri(piperidinothiocarbonyldithio)benzene
tetra(piperidinothiocarbonyldithio)neopentane
tetra(piperidinothiocarbonyldithio)pentaerythritol glycolate
1,1-bis(1-pyrrolidinylthiocarbonyldithio)methane
1,2-bis(1-pyrrolidinylthiocarbonyldithio)ethane
1,3-bis(1-pyrrolidinylthiocarbonyldithio)propane
1,4-bis(1-pyrrolidinylthiocarbonyldithio)butane
1,6-bis(1-pyrrolidinylthiocarbonyldithio)hexane
1,8-bis(1-pyrrolidinylthiocarbonyldithio)octane
1,10-bis(1-pyrrolidinylthiocarbonyldithio)decane
1,10-bis(1-pyrrolidinylthiocarbonyldithio)octadecane
1,18-bis(1-pyrrolidinylthiocarbonyldithio)octadecane
2,2'-bis(1-pyrrolidinylthiocarbonyldithio)oxydiethane
2,2'-bis(1-pyrrolidinylthiocarbonyldithio)thiodiethane
4,4'-bis(1-pyrrolidinylthiocarbonyldithio)oxydibutane
1,1'-bis(1-pyrrolidinylthiocarbonyldithio)-1,4-cyclohexanedimethane
1,4-bis(1-pyrrolidinylthiocarbonyldithio)benzene
α,α'-bis(1-pyrrolidinylthiocarbonyldithio)-p-xylene
1,2-bis(1-pyrrolidinylthiocarbonyldithio)cyclohexane
1,1-bis(1-pyrrolidinylthiocarbonyldithio)cyclohexane
2,9-di(1-pyrrolidinylthiocarbonyldithio)-p-menthane
1,4-bis(1-pyrrolidinylthiocarbonyldithio)naphthalene
2,5-di(1-pyrrolidinylthiocarbonyldithio)toluene
4,4'-bis(1-pyrrolidinylthiocarbonyldithio)biphenyl
4,4'-bis(1-pyrrolidinylthiocarbonyldithio)oxybisbenzene
bis(1-pyrrolidinylthiocarbonyldithio)glycolacetate
bis(1-pyrrolidinylthiocarbonyldithio)glycol propionate
1,2,3-tri(1-pyrrolidinylthiocarbonyldithio)propane
1,3,5-tri(1-pyrrolidinylthiocarbonyldithio)benzene
tetra(1-pyrrolidinylthiocarbonyldithio)neopentane
tetra(1-pyrrolidinylthiocarbonyldithio)pentaerythritol glycolate 1,1-bis(hexahydro-1H-azepin-1-ylthiocarbonyldithio)methane
1,2-bis(hexahydro-1H-azepin-1-ylthiocarbonyldithio)ethane
1,3-bis(hexahydro-1H-azepin-1-ylthiocarbonyldithio)propane
1,4-bis(hexahydro-1H-azepin-1-ylthiocarbonyldithio)butane
1,6-bis(hexahydro-1H-azepin-1-ylthiocarbonyldithio)hexane
1,8-bis(hexahydro-1H-azepin-1-ylthiocarbonyldithio)octane
1,10-bis(hexahydro-1H-azepin-1-ylthiocarbonyldithio)decane
1,10-bis(hexahydro-1H-azepin-1-ylthiocarbonyldithio)octadecane
1,18-bis(hexahydro-1H-azepin-1-ylthiocarbonyldithio)octadecane
2,2'-bis(hexahydro-1H-azepin-1-ylthiocarbonyldithio)oxydiethane
2,2'-bis(hexahydro-1H-azepin-1-ylthiocarbonyldithio)thiodiethane
4,4'-bis(hexahydro-1H-azepin-1-ylthiocarbonyldithio)oxydibutane
1,1'-bis(hexahydro-1H-azepin-1-ylthiocarbonyldithio)-1,4-cyclohexanedimethane
1,4bis(hexahydro-1H-azepin-1-ylthiocarbonyldithio)benzene
αα'-bis(hexahydro-1H-azepin-1-ylthiocarbonyldithio)-p-xylene
1,2bis(hexahydro-1H-azepin-1-ylthiocarbonyldithio)cyclohexane
1,1bis(hexahydro-1H-azepin-1-ylthiocarbonyldithio)cyclohexane
2,9di(hexahydro-1H-azepin-1-ylthiocarbonyldithio)-p-menthane
1,4bis(hexahydro-1H-azepin-1-ylthiocarbonyldithio)naphthalene
2,5di(hexahydro-1H-azepin-1-ylthiocarbonyldithio)toluene
4,4'bis(hexahydro-1H-azepin-1-ylthiocarbonyldithio)biphenyl
4,4'bis(hexahydro-1H-azepin-1-ylthiocarbonyldithio)oxybisbenzene
bis(hexahydro-1H-azepin-1-ylthiocarbonyldithio)glycolacetate
bis(hexahydro-1H-azepin-1-ylthiocarbonyldithio)glycol propionate
1,2,3-tri(hexahydro-1H-azepin-1-ylthiocarbonyldithio)propane
1,3,5-tri(hexahydro-1H-azepin-1-ylthiocarbonyldithio)benzene
tetra(hexahydro-1H-azepin-1-ylthiocarbonyldithio)neopentane
tetra(hexahydro-1H-azepin-1-ylthiocarbonyldithio)pentaerythritol glycolate
1,1-bis(2-benzothiazolyldithio)methane
1,2-bis(2-benzothiazolyldithio)ethane
1,3-bis(2-benzothiazolyldithio)propane
1,4-bis(2-benzothiazolyldithio)butane
1,6-bis(2-benzothiazolyldithio)hexane
1,8-bis(2-benzothiazolyldithio)octane
1,10-bis(2-benzothiazolyldithio)decane
1,10-bis(2-benzothiazolyldithio)octadecane
1,18-bis(2-benzothiazolyldithio)octadecane
2,2'-bis(2-benzothiazolyldithio)oxydiethane
2,2'-bis(2-benzothiazolyldithio)thiodiethane
4,4'-bis(2-benzothiazolyldithio)oxydibutane
1,1'-bis(2-benzothiazolyldithio)-1,4-cyclohexanedimethane
1,4-bis(2-benzothiazolyldithio)benzene
α,α'-bis(2-benzothiazolyldithio)-p-xylene
1,2-bis(2-benzothiazolyldithio)cyclohexane
1,1-bis(2-benzothiazolyldithio)cyclohexane
2,9-di(2-benzothiazolyldithio)-p-menthane
1,4-bis(2-benzothiazolyldithio)naphthalene
2,5-di(2-benzothiazolyldithio)toluene
4,4'-bis(2-benzothiazolyldithio)biphenyl
4,4'-bis(2-benzothiazolyldithio)oxybisbenzene
bis(2-benzothiazolyldithio)glycolacetate
bis(2-benzothiazolyldithio)glycol propionate
1,2,3-tri(2-benzothiazolyldithio)propane
1,3,5-tri(2-benzothiazolyldithio)benzene
tetra(2-benzothiazolyldithio)neopentane
tetra(2-benzothiazolyldithio)pentaerythritol glycolate
1,1-bis(2-thiazolyldithio)methane
1,2-bis(2-thiazolyldithio)ethane
1,3-bis(2-thiazolyldithio)propane
1,4-bis(2-thiazolyldithio)butane
1,6-bis(2-thiazolyldithio)hexane
1,8-bis(2-thiazolyldithio)octane
1,10-bis(2-thiazolyldithio)decane
1,10-bis(2-thiazolyldithio)octadecane
1,18-bis(2-thiazolyldithio)octadecane
2,2'-bis(2-thiazolyldithio)oxydiethane
2,2'-bis(2-thiazolyldithio)thiodiethane
4,4'-bis(2-thiazolyldithio)oxydibutane
1,1'-bis(2-thiazolyldithio)-1,4-cyclohexanedimethane
1,4-bis(2-thiazolyldithio)benzene
α,α'-bis(2-thiazolyldithio)-p-xylene
1,2-bis(2-thiazolyldithio)cyclohexane
1,1-bis(2-thiazolyldithio)cyclohexane
2,9-bis(2-thiazolyldithio)-p-menthane
1,4-bis(2-thiazolyldithio)naphthalene
2,5-bis(2-thiazolyldithio)toluene
4,4'-bis(2-thiazolyldithio)biphenyl
4,4'-bis(2-thiazolyldithio)oxybisbenzene
bis(2-thiazolyldithio)glycolacetate
bis(2-thiazolyldithio)glycol propionate
1,2,3-tri(2-thiazolyldithio)propane
1,3,5-tri(2-thiazolyldithio)benzene
tetra(2-thiazolyldithio)neopentane
tetra(2-thiazolyldithio)pentaerythritol glycolate
1,1-bis[2(4-phenyl-5-thioxo)-1,3,4-thiadiazolyldithio]methane
1,2-bis[2(4-phenyl-5-thioxo)-1,3,4-thiadiazolyldithio]ethane
1,3-bis[2(4-phenyl-5-thioxo)-1,3,4-thiadiazolyldithio]propane
1,4-bis[2(4-phenyl-5-thioxo)-1,3,4-thiadiazolyldithio]butane
1,6-bis[2(4-phenyl-5-thioxo)-1,3,4-thiadiazolyldithio]hexane
1,8-bis[2(4-phenyl-5-thioxo)-1,3,4-thiadiazolyldithio]octane
1,10-bis[2(4-phenyl-5-thioxo)-1,3,4-thiadiazolyldithio]decane
1,10-bis[2(4-phenyl-5-thioxo)-1,3,4-thiadiazolyldithio]octadecane
1,18-bis[2(4-phenyl-5-thioxo)-1,3,4-thiadiazolyldithio]octadecane
2,2'-bis[2(4-phenyl-5-thioxo)-1,3,4-thiadiazolyldithio]oxydiethane
2,2'-bis[2(4-phenyl-5-thioxo)-1,3,4-thiadiazolyldithio]thiodiethane 4,4'-bis[2(4-phenyl-5-thioxo)-1,3,4-thiadiazolyldithio]oxydibutane
1,1'-bis[2(4-phenyl-5-thioxo)-1,3,4-thiadiazolyldithio]-1,4-cyclohexanedimethane
1,4-bis[2(4-phenyl-5-thioxo)-1,3,4-thiadiazolyldithio]benzene
α,α'-bis[2(4-phenyl-5-thioxo)-1,3,4-thiadiazolyldithio]-p-xylene
1,2-bis[2(4-phenyl-5-thioxo)-1,3,4-thiadiazolyldithio]cyclohexane
1,2-bis[2(4-phenyl-5-thioxo)-1,3,4-thiadiazolyldithio]cyclohexane
2,9-di[2(4-phenyl-5-thioxo)-1,3,4-thiadiazolyldithio]-p-menthane
1,4-bis[2(4-phenyl-5-thioxo)-1,3,4-thiadiazolyldithio]naphthalene
2,5-di[2(4-phenyl-5-thioxo)-1,3,4-thiadiazolyldithio]toluene
4,4'-bis[2(4-phenyl-5-thioxo)-1,3,4-thiadiazolyldithio]biphenyl
4,4'-bis[2(4-phenyl-5-thioxo)-1,3,4-thiadiazolyldithio]oxybisbenzene
bis[2(4-phenyl-5-thioxo)-1,3,4-thiadiazolyldithio]glycolacetate
bis[2(4-phenyl-5-thioxo)-1,3,4-thiadiazolyldithio]glycol propionate
1,2,3-tri[2(4-phenyl-5-thioxo)-1,3,4-thiadiazolyldithio]propane
1,3,5-tri[2(4-phenyl-5-thioxo)-1,3,4-thiadiazolyldithio]benzene
tetra[2(4-phenyl-5-thioxo)-1,3,4-thiadiazolyldithio]neopentane
tetra[2(4-phenyl-5-thioxo)-1,3,4-thiadiazolyldithio]pentaerythritol glycolate
1,1-bis(O,O'-di-n-butylphosphorotrithioyl)methane
1,2-bis(O,O'-di-n-butylphosphorotrithioyl)ethane
1,3-bis(O,O'-di-n-butylphosphorotrithioyl)propane
1,4-bis(O,O'-di-n-butylphosphorotrithioyl)butane
1,6-bis(O,O'-di-n-butylphosphorotrithioyl)hexane
1,8-bis(O,O'-di-n-butylphosphorotrithioyl)octane
1,10-bis(O,O'-di-n-butylphosphorotrithioyl)decane
1,10-bis(O,O'-di-n-butylphosphorotrithioyl)octadecane
1,18-bis(O,O'-di-n-butylphosphorotrithioyl)octadecane
2,2'-bis(O,O'-di-n-butylphosphorotrithioyl)oxydiethane
2,2'-bis(O,O'-di-n-butylphosphorotrithioyl)thiodiethane
4,4'-bis(O,O'-di-n-butylphosphorotrithioyl)oxydibutane
1,1'-bis(O,O'-di-n-butylphosphorotrithioyl)-1,4-cyclohexanedimethane
1,4-bis(O,O'-di-n-butylphosphorotrithioyl)benzene
α,α'-bis(O,O'-di-n-butylphosphorotrithioyl)-p-xylene
1,2-bis(O,O'-di-n-butylphosphorotrithioyl)cyclohexane
1,1-bis(O,O'-di-n-butylphosphorotrithioyl)cyclohexane
2,9-di(O,O'-di-n-butylphosphorotrithioyl)-p-menthane
1,4-bis(O,O'-di-n-butylphosphorotrithioyl)naphthalene
2,5di(O,O'-di-n-butylphosphorotrithioyl)toluene
4,4'-bis(O,O'-di-n-butylphosphorotrithioyl)biphenyl
4,4'-bis(O,O'-di-n-butylphosphorotrithioyl)oxybisbenzene
bis(O,O'-di-n-butylphosphorotrithioyl)glycolacetate
bis(O,O'-di-n-butylphosphorotrithioyl)glycol propionate
1,2,3-tri(O,O'-di-n-butylphosphorotrithioyl)propane
1,3,5-tri(O,O'-di-n-butylphosphorotrithioyl)benzene
tetra(O,O'-di-n-butylphosphorotrithioyl)neopentane
tetra(O,O'-di-n-butylphosphorotrithioyl)pentaerythritol glycolate
1,1-bis(O,O'-diethylphosphorotrithioyl)methane
1,2-bis(O,O'-diethylphosphorotrithioyl)ethane
1,3-bis(O,O'-diethylphosphorotrithioyl)propane
1,4-bis(O,O'-diethylphosphorotrithioyl)butane
1,6-bis(O,O'-diethylphosphorotrithioyl)hexane
1,8-bis(O,O'-diethylphosphorotrithioyl)octane
1,10-bis(O,O'-diethylphosphorotrithioyl)decane
1,10-bis(O,O'-diethylphosphorotrithioyl)octadecane
1,18-bis(O,O'-diethylphosphorotrithioyl)octadecane
2,2'-bis(O,O'-diethylphosphorotrithioyl)oxydiethane
2,2'-bis(O,O'-diethylphosphorotrithioyl)thiodiethane
4,4'-bis(O,O'-diethylphosphorotrithioyl)oxydibutane
1,1'-bis(O,O'-diethylphosphorotrithioyl)-1,4-cyclohexanedimethane
1,4-bis(O,O'-diethylphosphorotrithioyl)benzene
α,α'-bis(O,O'-diethylphosphorotrithioyl)-p-xylene
1,2-bis(O,O'-diethylphosphorotrithioyl)cyclohexane
1,1-bis(O,O'-diethylphosphorotrithioyl)cyclohexane
2,9-di(O,O'-diethylphosphorotrithioyl)-p-menthane
1,4bis(O,O,'-diethylphosphorotrithioyl)naphthalene
2,5-di(O,O'-diethylphosphorotrithioyl)toluene
4,4'-bis(O,O'-diethylphosphorotrithioyl)biphenyl
4,4'-bis(O,O'-diethylphosphorotrithioyl)oxybisbenzene
bis(O,O'-diethylphosphorotrithioyl)glycolacetate
bis(O,O'-diethylphosphorotrithioyl)glycol propionate
1,2,3-tri(O,O'-diethylphosphorotrithioyl)propane
1,3,5-tri(O,O'-diethylphosphorotrithioyl)benzene
tetra(O,O'-diethylphosphorotrithioyl)neopentane
tetra(O,O'-diethylphosphorotrithioyl)pentaerythritol glycolate
1,1-bis(O,O'-dimethylphosphorotrithioyl)methane
1,2-bis(O,O'-dimethylphosphorotrithioyl)ethane
1,3-bis(O,O'-dimethylphosphorotrithioyl)propane
1,4-bis(O,O'dimethylphosphorotrithioyl)butane
1,6-bis(O,O'-dimethylphosphorotrithioyl)hexane
1,8-bis(O,O'-dimethylphosphorotrithioyl)octane
1,10-bis(O,O'-dimethylphosphorotrithioyl)decane
1,10-bis(O,O'-dimethylphosphorotrithioyl)octadecane
1,18-bis(O,O'-dimethylphosphorotrithioyl)octadecane
2,2'-bis(O,O'-dimethylphosphorotrithioyl)oxydiethane
2,2'-bis(O,O'-dimethylphosphorotrithioyl)thiodiethane
4,4'-bis(O,O'-dimethylphosphorotrithioyl)oxydibutane
1,1'-bis(O,O'-dimethylphosphorotrithioyl)-1,4-cyclohexanedimethane
1,4-bis(O,O'-dimethylphosphorotrithioyl)benzene
α,α'-bis(O,O'-dimethylphosphorotrithioyl)-p-xylene
1,2-bis(O,O'-dimethylphosphorotrithioyl)cyclohexane
1,1-bis(O,O'-dimethylphosphorotrithioyl)cyclohexane
2,9-di(O,O'-dimethylphosphorotrithioyl)-p-menthane
1,4-bis(O,O'-dimethylphosphorotrithioyl)naphthalene
2,5-bis(O,O'-dimethylphosphorotrithioyl)toluene
4,4'-bis(O,O'-dimethylphosphorotrithioyl)biphenyl
4,4'-bis(O,O'-dimethylphosphorotrithioyl)oxybisbenzene
bis(O,O'-dimethylphosphorotrithioyl)glycolacetate
bis(O,O'-dimethylphosphorotrithioyl)glycol propionate
1,2,3-tri(O,O'-dimethylphosphorotrithioyl)propane
1,3,5-tri(O,O'-dimethylphosphorotrithioyl)benzene tetra(O,O'-dimethylphosphorotrithioyl)neopentane
tetra(O,O-dimethylphosphorotrithioyl)pentaerythritol glycolate
1,1-bis(isopropoxythiocarbonyldithio)methane
1,2-bis(isopropoxythiocarbonyldithio)ethane
1,3-bis(isopropoxythiocarbonyldithio)propane
1,4-bis(isopropoxythiocarbonyldithio)butane
1,6-bis(isopropoxythiocarbonyldithio)hexane
1,8-bis(isopropoxythiocarbonyldithio)octane
1,10-bis(isopropoxythiocarbonyldithio)decane
1,10-bis(isopropoxythiocarbonyldithio)octadecane
1,18-bis(isopropoxythiocarbonyldithio)octadecane
2,2'-bis(isopropoxythiocarbonyldithio)oxydiethane
2,2'-bis(isopropoxythiocarbonyldithio)thiodiethane
4,4'-bis(isopropoxythiocarbonyldithio)oxydibutane
1,1'-bis(isopropoxythiocarbonyldithio)-1,4-cyclohexanedimethane
1,4-bis(isopropoxythiocarbonyldithio)bnzene
α,α'-bis(isopropoxythiocarbonyldithio)-p-xylene
1,2-bis(isopropoxythiocarbonyldithio)cyclohexane
1,1-bis(isopropoxythiocarbonyldithio)cyclohexane
2,9-di(isopropoxythiocarbonyldithio)-p-menthane
1,4-bis(isopropoxythiocarbonyldithio)naphthalene
2,5-di(isopropoxythiocarbonyldithio)toluene
4,4'-bis(isopropoxythiocarbonyldithio)biphenyl
4,4'-bis(isopropoxythiocarbonyldithio)oxybisbenzene
bis(isopropoxythiocarbonyldithio)glycolacetate
bis(isopropoxythiocarbonyldithio)glycol propionate
1,2,3-tri(isopropoxythiocarbonyldithio)propane
1,3,5-tri(isopropoxythiocarbonyldithio)benzene
tetra(isopropoxythiocarbonyldithio)neopentane
tetra(isopropoxythiocarbonyldithio)pentaerythritol glycolate
1,1-bis(ethoxythiocarbonyldithio)methane
1,2-bis(ethoxythiocarbonyldithio)ethane
1,3-bis(ethoxythiocarbonyldithio)propane
1,4-bis(ethoxythiocarbonyldithio)butane
1,6-bis(ethoxythiocarbonyldithio)hexane
1,8-bis(ethoxythiocarbonyldithio)octane
1,10-bis(ethoxythiocarbonyldithio)decane
1,10-bis(ethoxythiocarbonyldithio)octadecane
1,18-bis(ethoxythiocarbonyldithio)octadecane
2,2'-bis(ethoxythiocarbonyldithio)oxydiethane
2,2'-bis(ethoxythiocarbonyldithio)thiodiethane
4,4'-bis(ethoxythiocarbonyldithio)oxydibutane
1,1'-bis(ethoxythiocarbonyldithio)-1,4-cyclohexanedimethane
1,4-bis(ethoxythiocarbonyldithio)benzene
α,α'-bis(ethoxythiocarbonyldithio)-p-xylene
1,2-bis(ethoxythiocarbonyldithio)cyclohexane
1,1-bis(ethoxythiocarbonyldithio)cyclohexane
2,9-di(ethoxythiocarbonyldithio)-p-menthane
1,4-bis(ethoxythiocarbonyldithio)naphthalene
2,5-di(ethoxythiocarbonyldithio)toluene
4,4'-bis(ethoxythiocarbonyldithio)biphenyl
4,4'-bis(ethoxythiocarbonyldithio)oxybisbenzene
bis(ethoxythiocarbonyldithio)glycolacetate
bis(ethoxythiocarbonyldithio)glycol propionate
1,2,3-tri(ethoxythiocarbonyldithio)propane
1,3,5-tri(ethoxythiocarbonyldithio)benzene
tetra(ethoxythiocarbonyldithio)neopentane
tetra(ethoxythiocarbonyldithio)pentaerythritol glycolate
1,1-bis(methoxythiocarbonyldithio)methane
1,2-bis(methoxythiocarbonyldithio)ethane
1,3-bis(methoxythiocarbonyldithio)propane
1,4-bis(methoxythiocarbonyldithio)butane
1,6-bis(methoxythiocarbonyldithio)hexane
1,8-bis(methoxythiocarbonyldithio)octane
1,10-bis(methoxythiocarbonyldithio)decane
1,10-bis(methoxythiocarbonyldithio)octadecane
1,18-bis(methoxythiocarbonyldithio)octadecane
2,2'-bis(methoxythiocarbonyldithio)oxydiethane
2,2'-bis(methoxythiocarbonyldithio)thiodiethane
4,4'-bis(methoxythiocarbonyldithio)oxydibutane
1,1'-bis(methoxythiocarbonyldithio)-1,4-cyclohexanedimethane
1,4-bis(methoxythiocarbonyldithio)benzene
α,α'-bis(methoxythiocarbonyldithio)-p-xylene
1,2-bis(methoxythiocarbonyldithio)cyclohexane
1,1-bis(methoxythiocarbonyldithio)cyclohexane
2,9-di(methoxythiocarbonyldithio)-p-menthane
1,4-bis(methoxythiocarbonyldithio)naphthalene
2,5-di(methoxythiocarbonyldithio)toluene
4,4'-bis(methoxythiocarbonyldithio)biphenyl
4,4'-bis(methoxythiocarbonyldithio)oxybisbenzene
bis(methoxythiocarbonyldithio)glycolacetate
bis(methoxythiocarbonyldithio)glycol propionate
1,2,3-tri(methoxythiocarbonyldithio)propane
1,3,5-tri(methoxythiocarbonyldithio)benzene
tetra(methoxythiocarbonyldithio)neopentane
tetra(methoxythiocarbonyldithio)pentaerythritol glycolate
1,1-bis(2-pyrimidinyldithio)methane
1,2-bis(2-pyrimidinyldithio)ethane
1,3-bis(2-pyrimidinyldithio)propane
1,4-bis(2-pyrimidinyldithio)butane
1,6-bis(2-pyrimidinyldithio)hexane
1,8-bis(2-pyrimidinyldithio)octane
1,10-bis(2-pyrimidinyldithio)decane
1,10-bis(2-pyrimidinyldithio)octadecane
1,18-bis(2-pyrimidinyldithio)octadecane
2,2'-bis(2-pyrimidinyldithio)oxydiethane
2,2'-bis(2-pyrimidinyldithio)thiodiethane
4,4'-bi(2-pyrimidinyldithio)oxydibutane
1,1'-bis(2-pyrimidinyldithio)-1,4-cyclohexanedimethane
1,4-bis(2-pyrimidinyldithio)benzene
α,α'-bis(2-pyrimidinyldithio)-p-xylene
1,2-bis(2-pyrimidinyldithio)cyclohexane
1,1-bis(2-pyrimidinyldithio)cyclohexane
2,9-di(2-pyrimidinyldithio)-p-menthane
1,4-bis(2-pyrimidinyldithio)naphthalene
2,5-di(2-pyrimidinyldithio)toluene
4,4'-bis(2-pyrimidinyldithio)biphenyl
4,4'-bis(2-pyrimidinyldithio)oxybisbenzene
bis(2-pyrimidinyldithio)glycolacetate
bis(2-pyrimidinyldithio)glycol propionate
1,2,3-tri(2-pyrimidinyldithio)propane
1,3,5-tri(2-pyrimidinyldithio)benzene
tetra(2-pyrimidinyldithio)neopentane
tetra(2-pyrimidinyldithio)pentaerythritol glycolate
1,1-bis[2(4,6-dimethylpyrimidinyl)dithio]methane
1,2-bis[2(4,6-dimethylpyrimidinyl)dithio]ethane
1,3-bis[2(4,6-dimethylpyrimidinyl)dithio]propane
1,4-bis[2(4,6-dimethylpyrimidinyl)dithio]butane
1,6-bis[2(4,6-dimethylpyrimidinyl)dithio]hexane
1,8-bis[2(4,6-dimethylpyrimidinyl)dithio]octane
1,10-bis[2(4,6-dimethylpyrimidinyl)dithio]decane
1,10-bis[2(4,6-dimethylpyrimidinyl)dithio]octadecane
1,18-bis[2(4,6-dimethylpyrimidinyl)dithio]octadecane
2,2'-bis[2(4,6-dimethylpyrimidinyl)dithio]oxydiethane
2,2'-bis[2(4,6-dimethylpyrimidinyl)dithio]thiodiethane 4,4'-bis[2(4,6-dimethylpyrimidinyl)dithio]oxydibutane
1,1'-bis[2(4,6-dimethylpyrimidinyl)dithio]-1,4-cyclohexanedimethane
1,4-bis[2(4,6-dimethylpyrimidinyl)dithio]benzene
α,α'-bis[2(4,6-dimethylpyrimidinyl)dithio]-p-xylene
1,2-bis[2(4,6-dimethylpyrimidinyl)dithio]cyclohexane
1,1-bis[2(4,6-dimethylpyrimidinyl)dithio]cyclohexane
2,9-di[2(4,6-dimethylpyrimidinyl)dithio]-p-menthane
1,4-bis[2(4,6-dimethylpyrimidinyl)dithio]naphthalene
2,5-di[2(4,6-dimethylpyrimidinyl)dithio]toluene
4,4'-bis[2(4,6-dimethylpyrimidinyl)dithio]biphenyl
4,4'-bis[2(4,6-dimethylpyrimidinyl)dithio]oxybisbenzene
bis[2(4,6-dimethylpyrimidinyl)dithio]glycolacetate
bis[2(4,6-dimethylpyrimidinyl)dithio]glycol propionate
1,2,3-tri[2(4,6-dimethylpyrimidinyl)dithio]propane
1,3,5-tri[2(4,6-dimethylpyrimidinyl)dithio]benzene
tetra[2(4,6-dimethylpyrimidinyl)dithio]neopentane
tetra[2(4,6-dimethylpyrimidinyl)dithio]pentaerythritol glycolate
1,1-bis[2(4,6-dimethylamino)-s-triazinyldithio]methane
1,2-bis[2(4,6-dimethylamino)-s-triazinyldithio-]ethane
1,3-bis[2(4,6-dimethylamino)-s-triazinyldithio]propane
1,4-bis[2(4,6-dimethylamino)-s-triazinyldithio]butane
1,6-bis[2(4,6-dimethylamino)-s-triazinyldithio]hexane
1,8-bis[2(4,6-dimethylamino)-s-triazinyldithio]octane
1,10-bis[2(4,6-dimethylamino)-s-triazinyldithio]decane
1,10-bis[2(4,6-dimethylamino)-s-triazinyldithio]octadecane
1,18-bis[2(4,6-dimethylamino)-s-triazinyldithio]octadecane
2,2'-bis[2(4,6-dimethylamino)-s-triazinyldithio]oxydiethane
2,2'-bis[2(4,6-dimethylamino)-s-triazinyldithio]thiodiethane
4,4'-bis[2(4,6-dimethylamino)-s-triazinyldithio]oxydibutane
1,1'-bis[2(4,6-dimethylamino)-s-triazinyldithio]-1,4-cyclohexanedimethane
1,4-bis[2(4,6-dimethylamino)-s-triazinyldithio]benzene
α,α'-bis[2(4,6-dimethylamino)-s-triazinyldithio]-p-xylene
1,2-bis[2(4,6-dimethylamino)-s-triazinyldithio]cyclohexane
1,1-bis[2(4,6-dimethylamino)-s-triazinyldithio]cyclohexane
2,9-di[2(4,6-dimethylamino)-s-triazinyldithio]-p-menthane
1,4-bis[2(4,6-dimethylamino)-s-triazinyldithio]naphthalene
2,5-di[2(4,6-dimethylamino)-s-triazinyldithio]toluene
4,4'-bis[2(4,6-dmethylamino)-s-triazinyldithio]biphenyl
4,4'-bis[2(4,6-dimethylamino)-s-triazinyldithio]oxybisbenzene
bis[2(4,6-dimethylamino)-s-triazinyldithio]glycolacetate
bis[2(4,6-dimethylamino)-s-triazinyldithio]glycol propionate
1,2,3-tri[2(4,6-dimethylamino)-s-triazinyldithio]propane
1,3,5-tri[2(4,6-dimethylamino)-s-triazinyldithio]benzene
tetra[2(4,6-dimethylamino)-s-triazinyldithio]neopentane
tetra[2(4,6-dimethylamino)-s-triazinyldithio]pentaerythritol glycolate
1,1-bis(2-pyridinyldithio)methane
1,2-bis(2-pyridinyldithio)ethane
1,3-bis(2-pyridinyldithio)propane
1,4-bis(2-pyridinyldithio)butane
1,6-bis(2-pyridinyldithio)hexane
1,8-bis(2-pyridinyldithio)octane
1,10-bis(2-pyridinyldithio)decane
1,10-bis(2-pyridinyldithio)octadecane
1,18-bis(2-pyridinyldithio)octadecane
2,2'-bis(2-pyridinyldithio)oxydiethane
2,2'-bis(2-pyridinyldithio)thiodiethane
4,4'-bis(2-pyridinyldithio)oxydibutane
1,1'-bis(2-pyridinyldithio)-1,4-cyclohexanedimethane
1,4-bis(2-pyridinyldithio)benzene
α,α'-bis(2-pyridinydithio)-p-xylene
1,2-bis(2-pyridinyldithio)cyclohexane
1,1-bis(2-pyridinyldithio)cyclohexane
2,9-di(2-pyridinyldithio)-p-menthane
1,4-bis(2-pyridinyldithio)naphthalene
2,5-di(2-pyridinyldithio)toluene
4,4'-bis(2-pyridinyldithio)biphenyl
4,4'-bis(2-pyridinyldithio)oxybisbenzene
bis(2-pyridinyldithio)glycolacetate
bis(2-pyridinyldithio)glycol propionate
1,2,3-tri(2-pyridinyldithio)propane
1,3,5-tri(2-pyridinyldthio)benzene
tetra(2-pyridinyldithio)neopentane
tetra(2-pyridinyldithio)pentaerythritol glycolate The above compounds are illustrative of compounds of the general formula wherein $x$ is one, however, analogous compounds having one or more additional sulfur atoms are included in this invention. The trisulfides are named by changing the dithio in the above compounds to trithio.

The fact that mono and disulfidic cross-links are thermally more stable than higher polysulfidic cross-links accounts for the excellent reversion properties of vulcanizates from cross-linking agents $(AccSS_x)_nR$-$S_xAcc$ where $x$ is 1. The vulcanizate prepared from cross-link agents of the formula $(AccSS)_nRSSAcc$ have a substantial proportion of monosulfidic cross-links and considerably higher than vulcanizates prepared with conventional sulfenamide-sulfur cure systems according to the percent of non-reducible cross-links determined by the procedure described by A. Y. Coran, *Rubber Chem. and Tech.*, V37, p 668 (1964).

The amount of cross-linking agent used may vary from 0.1 to 30 parts per 100 parts rubber; normally the amount is 0.5 – 6 parts per 100 parts rubber with 1.0 – 4.0 parts being preferred. Generally the modulus of the vulcanizate varies proportionally with the amount of cross-linking agent used.

The cross-linking agents of this invention may be incorporated into rubber by conventional mixing procedures, for example, by adding them in a Banbury mixer or by adding them to the rubber on a mill. Ordinarily with liquid or low melting solid cross-linking agents no special precautions are necessary for obtaining good dispersions. However, when using higher melting cross-linking agents it is recommended that they be ground to a fine powder, preferably 200 mesh or less, to assure adequate dispersion. The cross-linking agent alone effects cross-linking of rubber in the absence of other ingredients but it is preferred to use it in conjunction with conventional compounding ingredients. The rubber stocks may include reinforcing carbon blacks, pigments such as titanium dioxide and silicon dioxide, metal oxide activators such as zinc oxide and magnesium oxide, stearic acid, hydrocarbon softeners and extender oils, amine, ether, and phenolic antidegradants, phenylenediamine antidegradants, tackifiers and phenolic and resorcinol resin adhesive agents. The stocks may also contain prevulcanization inhibitors but in many stocks their use is unwarranted because of the excellent processing safety of the instant cross-linking agents.

In many applications, the cross-linking agents of this invention will be used without sulfur or accelerating agent. However, for certain applications it is desirable to use them with sulfur, accelerator or both, particularly if very high modulus properties are required. The amount of elemental sulfur will usually be within the range of 0–1.5 parts by weight and it is preferred that the amount of elemental sulfur, if present, be within the range of 0.5–1.5 parts per hundred parts by weight of the rubber as characteristic of low sulfur cures. Larger amounts of sulfur result in decreased processing safety and vulcanizates having less reversion resistance. It will be understood that any sulfur-vulcanizing agent may be used in place of sulfur and suitable vulcanizates obtained with the cross-linking agents of the invention.

Rubber stocks containing the cross-linking agents of this invention may be heated over a wide range of temperatures to effect vulcanization. Generally higher cure temperatures are used with synthetic rubber stocks than with natural rubber stocks. Cure temperatures of 250°–550°F are suitable with temperatures of 280°–350°F being more frequently used. The selection of the proper cure temperature depends upon the ingredients in the rubber composition. A compounder may determine the proper curing parameters for any particular stock by testing the composition with an oscillating disk rheometer. The cross-linking agents having thiocarbamoyl accelerating moieties generally require cure temperatures similar to those used in conventional sulfur-sulfenamide accelerator stocks, usually between 280°–350°F. The cross-linking agents having thiazolyl, particularly benzothiazolyl, accelerating moieties are especially adaptable for higher cure temperatures, for example, 300°–400°F or higher. Certain cross-linking agents with xanthogen accelerating moieties may be cured at lower temperatures, for example, certain rubber compositions may cure at room temperature over several hours. The cure time may be shortened by increasing the temperature; cure temperatures of 100°–250°F are sometimes advantageous.

The cross-linking agents of the invention are suitable for any rubber having sufficient unsaturation to be sulfurvulcanizable. Any of the diene rubbers, natural rubber, synthetic rubber of mixtures thereof are suitable. Synthetic rubbers which may be vulcanized by the process of this invention include cis-1,4-polybutadiene, butyl rubber, ethylene-propylene terpolymers, homopolymers of 1,3-butadiene and isoprene such as polybutadiene and polyisoprene, copolymers of 1,3-butadiene with other monomers, for example styrene, acrylonitrile, isobutylene and methyl methacrylate. In addition, certain specialty elastomers which depend upon the presence of active halogen for vulcanizates but are not commonly regarded as sulfur vulcanizable are cross-linked by the agents of the invention, for example, chlorobutyl rubber, chlorosulfonated polyethylene and polychloropropene, commonly called neoprene. The nature of the cross-link and the mechanism by which it is formed in specialty rubber is unknown. The cross-link agents are, of course, applicable to mixtures of diene and specialty rubber.

Rubber stocks containing the cross-linking agents of this invention are suitable for bonding to natural or synthetic textile materials. The use of bonding agents commonly used for the particular filament is recommended. Generally, by using the conventional adhesive systems good adhesion is obtained with continuous or discontinuous filaments of cotton, rayon, nylon, glass, polyester or steel. The degree of adhesion obtaned varies somewhat from cross-link agent to cross-link agent and sometimes mixtures of two or more cross-link agents give better adhesion.

It is particularly advantageous to use the cross-linking agents of this invention in stocks which will be in contact with polyester fiber. Certain accelerating and vulcanization systems are known to have a deleterious effect toward polyester aged stability. However, polyester fibers bonded to rubber cross-linked with the subject cross-linking agents show excellent strength retention even after aging at elevated temperature.

For the rubber stocks tested and described herein as illustrative of the invention, Mooney scorch times at 121° and 135°C are determined by means of a Mooney plastometer. The time in minutes ($t_5$) required for the Mooney reading to rise five points above the minimum viscosity is recorded. Longer times on the Mooney scorch test are desirable because this indicates greater processing safety. Cure characteristics are determined at the designated temperatures by means of the Monsanto Oscillating Disk Rheometer which is described by Decker, Wise and Guerry in *Rubber World*, December 1962, page 68. From the rheometer data, the minimum torque, R min., in rheometer units is recorded. The increase in torque is a measure of the degree of vulcanization and is proportional to the cross-link density. The time, $t_2$, in minutes for a rise of two rheometer units above the minimum reading of the rubber sample and the time, $t_{90}$, required to obtain a torque of 90% of the maximum is recorded. The difference, $t_{90}-t_2$, is a measure of the cure rate of the sample. Vulcanizates are prepared by press curing at the selected temperature for the time indicated by the rheometer data to obtain optimum cure. The physical properties of the vulcanizates are measured by conventional methods.

PREFERRED EMBODIMENTS

PREPARATION OF COMPOUNDS

The compounds are prepared by reacting a polysulfenyl chloride with a thiol, a thioic acid or alkali metal salt of a thioic acid. The polysulfenyl chloride intermediate is prepared by reacting chlorine with a polythiol. A typical procedure for preparing sulfenyl chloride intermediate is as follows: 1,2-ethanedithiol (94 g., 1.0 mole) and 1000 ml. of benzene is placed in a 2 liter flask equipped with a condenser, stirrer and gas inlet tube. To the stirred solution maintained at 25°C by a water bath, there is added 1.0 mole of chlorine at the rate of about one gram per minute. At first a colorless solid precipitates but as the chlorine addition continues, the precipitate dissolves and a clear orange solution is obtained when all the chlorine is added. Then, 100 ml. of benzene is removed on a rotary evaporator. The resulting benzene solution of 1,2-ethanedisulfenyl chloride is ready for use as reactant without further purification. Other sulfenyl chloride solutions are prepared by analogous procedures. Sometimes, it is desirable to conduct the chlorine addition at lower temperatures, often 0°C is satisfactory. Also, solvents other than benzene may be used and sometimes are preferred.

In a three liter flask equipped with stirrer, condenser and funnel is placed 80 g. (2.0 mole) of sodium hydroxide, 1040 g. of water and 360 ml. (2.0 mole) of 25% aqueous dimethylamine. The solution is cooled to 5°–10°C and 152 g. (2.0 mole) of carbon disulfide is added to the stirred solution over a 45 minute period. When the addition is complete, the temperature bath is removed and stirring is continued for 90 minutes. The 1,2-ethanedisulfenylchloride solution prepared above is added to the aqueous solution of sodium dimethyldithiocarbamate over a 1-hour period while maintaining the temperature at 20°–40°C. The mixture is stirred 1 additional hour. The precipitate which forms is collected by filtration, washed with water and dried to give 235 grams (71% yield) of 1,2-bis(dimethylthiocarbamoyldithio)ethane. The product recrystallized three times from toluene is a pale yellow solid, m.p. 141.5°–143°C. Identification is confirmed by nuclear magnetic resonance spectral analysis. NMR: 3.55, by broad singlet (12H); 3.17, singlet (4H). A Varian A-60 NMR spectrometer is used for all NMR measurements and the absorption bands are reported using the delta scale.

The above preparation is illustrated by the following equation:

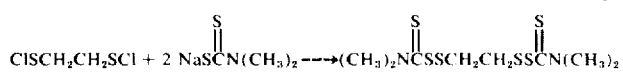

In a similar manner other dithiocarbamate-sulfenyl chloride derivatives are prepared. In case of liquid products, the solvents are removed by evaporation. The compounds and their properties are given in Table I.

An alternative procedure comprises preparing the compounds via Bunte salt intermediates. For example, a Bunte salt is prepared by refluxing for one hour sodium thiosulfate pentahydrate (0.22 mole) and trans-1,4-dichloro-2-butene (0.1 mole) in 100 ml. of water and 70 ml. of ethanol. The ethanol is vacuum stripped and 200 ml. of water added. Sodium acetate trihydrate (0.3 mole) and 20 ml. of 35% aqueous formaldehyde are added to the Bunte salt solution. To this mixture, there is added dropwise over 30 minutes with stirring, sodium hexahydro-1H-azepin-1-ylthiocarbothiolate at room temperature. After stirring 1.5 hours, the oily product is extracted with chloroform, washed with water, dried with sodium sulfate and vacuum stripped. 1,4-Bis(hexahydro-1H-azepin-1-ylthiocarbonyldithio)-2-butene is recovered.

Similarly, the reaction of the Bunte salt of $\alpha,\alpha'$-dichloro-p-xylene gives the following compounds:

$\alpha,\alpha'$-bis(N,N-dimethylthiocarbamoyldithio)-p-xylene, m.p. 155°C.

$\alpha,\alpha'$-bis(N,N-diethylthiocarbamoyldithio)-p-xylene, m.p. 119°–122°C.

$\alpha,\alpha'$-bis(N,N-diisopropylthiocarbamoyldithio)-p-xylene, m.p. 158°–160°C.

$\alpha,\alpha'$-bis(N,N-di-n-butylthiocarbamoyldithio)-p-xylene, m.p. 54°–56°C.

$\alpha,\alpha'$-bis(N,N-dicyclohexylthiocarbamoyldithio)-p-xylene, m.p. 90°–95°C.

$\alpha,\alpha'$-bis(piperidinothiocarbonyldithio)-p-xylene, m.p. 125°–128°C.

$\alpha,\alpha'$-bis(2,6-dimethylmorpholinothiocarbonyldithio)-p-xylene, m.p. 170°–172°C.

TABLE I

| Compound | Melting Point, °C | NMR |
|---|---|---|
| 1,2-bis(N,N-di-n-propylthiocarbamoyldithio)ethane | 87–88[a] | 3.8 very broad (8H); 3.17 singlet (4H); 1.4–2.1 multiplet (8H); 0.97 triplet (12H) |
| 1,1'-bis(N,N-dimethylthiocarbamoyldithio)-2,2'-oxydiethane | 90.5–91.5[b] | 3.77 triplet; 3.55 singlet; 3.05 triplet |
| 1,2-bis(hexahydro-1H-azepin-1-ylthiocarbonyldithio)ethane* | 135[c] | 4.1 mult. (8H); 3.16 singlet (4H); 1.8 mult. (16H) |
| 1,2-bis(N-butyl-N-ethylthiocarbamoyldithio)ethane | Liquid | 3.8 singlet; 3.17 singlet; 2.0 mult.; 1.0 mult. |
| 1,2-bis(N-cyclohexyl-N-n-propylthiocarbamoyldithio)ethane | Oil | 3.7 mult.; 3.15 singlet; 2.0 mult.; 1.0 triplet |
| 1,2-bis(N,N-diisopropylthiocarbamoyldithio)ethane | 127.5–128.5[b] | 4.8 broad; 3.1 singlet; 1.5 doublet |
| 1,2-bis(N,N-diethylthiocarbamoyldithio)ethane | 100–102[a] | 4.0 mult. (8H); 3.17 singlet (4H); 1.3 triplet (12H) |
| 1,3-bis(morpholinothiocarbonyldithio)propane | Oil | 4.1 mult.; 3.8 mult.; 3.1 mult.; 2.2 mult. |
| $\alpha,\alpha'$-bis(morpholinothiocarbonyldithio)-p-xylene | 149 | 7.2 singlet; 4.1 mult.; 3.75 mult. |
| 1,2-bis(1-pyrrolidinylthiocarbonyldithio)ethane | 160–161[c] | 3.8 mult.; 3.17 singlet; 2.1 mult. |
| 1,2-bis(piperidinothiocarbonyldithio)ethane | 155–157 | 4.15 singlet; 3.17 singlet; 1.7 singlet |
| 1,2-bis(2,6-dimethylmorpholinothiocarbonyldithio)ethane | 144–146[b] | 5.0 mult.; 3.8 mult.; 3.15 singlet; 1.25 doublet |

TABLE I-continued

| Compound | Melting Point, °C | NMR |
|---|---|---|
| α,α'-bis(piperidinothiocarbonyl-dithio)-m-xylene | 118–120[a] | 7.2 mult.; 4.1 mult.; 1.7 mult. |
| α,α'-bis(1-pyrrolidinylthio-carbonyldithio)-p-xylene | 170 | 7.3 mult.; 4.1 singlet; 4.1–3.4 mult.; 2.1–1.8 mult. |
| 2,9-di(1-pyrrolidinylthio-carbonyldithio)-p-menthane | Glass | 4.0 mult.; 3.0–1.0 mult. |
| 1,2-di(N,N-dimethylthiocarbamoyl-dithio)-1-phenylethane | Oil | 7.33 singlet (5H); 5.2, 5.35 triplets (1H); 3.5–3.7 mult. (2H); 3.4 singlet (12H) |
| α,α'-bis(hexahydro-1H-azepin-1-ylthiocarbamoyldithio)-p-xylene | 148–150 | 7.22 singlet (4H); 4.03 singlet (4H); 3.7–4.3 mult. (8H); 1.4–2.1 mult. (16H) |
| 1,2-di(hexahydro-1H-azepin-1-ylthiocarbamoyldithio)-n-hexane | Oil | 3.7–4.3 mult. (8H); 2.9–3.4 mult. (3H); 1.1–2.2 mult. (22H); 0.92 triplet (3H) |
| 1,2-di(hexahydro-1H-azepin-1-ylthiocarbamoyldithio)-n-octane | Oil | 3.8–4.4 mult. (8H); 2.9–3.5 mult. (3H); 1.0–2.2 mult. (26H); 0.88 triplet (3H) |
| 1,2-di(hexahydro-1H-azepin-1-ylthiocarbamoyldithio)-1-phenylethane | Oil | 7.32 singlet (5H); 5.2 triplet (1H); 3.3–4.25 mult. (10H); 1.3–2.05 mult. (16H) |

[a]Recrystallized from isopropyl alcohol
[b]Recrystallized from heptane/toluene
[c]Recrystallized from toluene
[d]Recrystallized from heptane
*Chemical analysis gives 43.65% C, 6.21% H, 6.53% N and 43.80% S compared to 43.60% C, 6.40% H, 6.35% N and 43.64% S calculated for $C_{16}H_{28}N_2S_8$.

Bis-dithiocarbamates from primary amines are similarly prepared. For example, addition of 1,2-ethanedisulfenyl chloride solution to an aqueous solution of sodium benzyldithiocarbamate gives nearly a quantitative yield of 1,2-bis(N-benzylthiocarbamoyldithio)ethane, m.p. 105°–110°C, decom., NMR 7.3 singlet, 4.9 mult., 3.4 singlet and 3.15 singlet.

An alternative procedure for preparing the bis(dithiocarbamate) cross-linking agents comprises reacting carbon disulfide with a bis sulfenamide as described by Dunbar and Rogers, J. of Org. Chem. 35, 279 (1970), who indicated that they prepared bis(morpholinothiocarbonyldithio)pentane by this reaction. For example, 1,2-bis(morpholinothio)ethane is prepared by adding 1,2-ethanedisulfenyl chloride (0.4 mole) prepared as previously described in 275 ml. of benzene to a stirred solution of 139.2 g. of morpholine and 100 ml. of benzene at 25°–35°C over a 20 minute period. The mixture is stirred one hour and the precipitate collected by filtration, washed with water and dried. The 1,2-bis(morpholinothio)ethane melts after recrystallization from toluene at 108.7°–109.5°C. The 1,2-bis(morpholinothio)ethane, 7.92 g. (0.03 mole) and 50 ml. of carbon disulfide are charged into a flask equipped with a condenser; and the mixture is heated at reflux for 30 minutes. An additional charge of 50 ml. of carbon disulfide is added to the reactor and the mixture is refluxed an additional 30 minutes; after which time the mixture is cooled and allowed to stand overnight. A colorless precipitate is recovered by filtration and air dried. A 90% yield (11.2 g.) of 1,2-bis(morpholinothiocarbonyldithio)ethane, m.p. 169°C, is recovered. NMR: 4.1–4.3 mult. (8H); 3.7–3.9 mult. (8H); 3.18 singlet (4H).

Substituting 1,6-bis(morpholinothio)hexane in the above procedure gives 1,6-bis(morpholinothiocarbonyldithio)hexane, m.p. 92°–93°C, recrystallized from toluene-heptane. NMR: 4.1–4.3 multiplet (8H); 3.7–3.9 multiplet (8H); 2.88 triplet (4H); 1.4–1.8 multiplet (8H). Substituting 2,2'-bis(morpholinothio)oxydiethane in the above procedure gives 2,2'-bis(morpholinothiocarbonyldithio)oxydiethane, an oil at room temperature. NMR: 4.1–4.3 mult. (8H); 3.6–3.9 mult. (8H); 3.08 triplet (4H).

Reaction of carbon disulfide with the di(morpholinothio)benzenes of Feher et al., Z. Naturforsch 26b, 67 (1971) gives the corresponding dithiocarbamate cross-linking agents with an aromatic bridging group.

Cross-linking agents with azole accelerating moieties may be prepared by condensing a polysulfenyl chloride with a 2-mercaptoazole in the presence of an acid acceptor, or with an alkali metal salt of a mercaptoazole. Alternatively, 2-azolylsulfenyl chloride, for example, 2-benzothiazolylsulfenyl chloride, may be condensed with a dithiol, preferably in the presence of an acid acceptor, to give the desired bis-compounds. The following preparations illustrate suitable synthesis procedures.

Into a 2 liter glass reactor equipped with a stirrer, condenser and funnel is charged 175 g. (1.0 mole) 2-mercaptobenzothiazole (95% purity), 500 ml. of benzene and 122 g. (1.01 mole) of collidine. 1,2-Ethanedisulfenyl chloride (0.5 mole) is added slowly over 45 minutes to the stirred mixture at 10°C. After stirring the mixture 5 hours at room temperature, the solids are slurried in 2 liters of water to remove the collidine hydrochloride, collected on a filter, washed with 500 ml. of 1% aqueous HCl, 500 ml. of water and 1000 ml. of 1% aqueous sodium hydroxide and dried. 1,2-bis-(2-benzothiazolyldithio)ethane, m.p. 119°–120.5°C recrystallized from benzene, is obtained. NMR: 7.7–8.0 mult. (4H); 7.3–7.5 mult. (4H); 3.36 singlet (4H).

Substituting 2-mercaptothiazoline in the above procedure gives 1,2-bis(2-thiazolinyldithio)ethane, a colorless solid, m.p. 101.5°–102°C, recrystallized from heptane. NMR: 4.4 triplet; 3.4 triplet; 3.2 singlet. Substituting 2-mercaptothiazole gives 1,2-bis(2-thiazolyldithio)ethane.

Using 4,5,6,7(tetrahydro)-2-mercaptobenzothiazole as the reactant gives 1,2-bis[2(4,5,6,7-tetrahydro)benzothiazolyldithio]ethane, a tan solid, m.p. 91°–93°C. NMR: 3.25 singlet (4H); 2.70 mult. (8H); 1.8 mult. (8H). 2-Mercapto-4-methylthiazole gives 1,2-bis[2(4-methylthiazolyl)dithio]ethane, a brown liquid. NMR: 7.5 mult. (2H); 3.26 singlet (4H); 2.32 doublet (6H). 2Mercapto-4-methyl-5-carboethoxythiazole gives 1,2-bis[2(4-methyl-5-carboethoxythiazolyl)dithio]ethane, a brown oil. NMR: 4.2 triplet (4H) J=7 cps; 3.24 singlet (4H); 3.0 triplet (4H) J=7 cps; 2.20 singlet (6H); 2.0 singlet (6H).

Reacting 2-mercaptobenzoxazole with 1,2-ethanedisulfenyl chloride in the presence of pyridine gives 1,2-bis-(2-benzoxazolyldithio)ethane, a white solid, m.p. 124°–125°C recrystallized from petroleum ether-chloroform. NMR: 7.16–7.6 mult. (8H); 3.43 singlet (4H).

Similarly, reacting α,α'-p-xylenedisulfenyl chloride with 2-mercaptobenzothiazole gives α,α'-bis(2-benzothiazolyldithio)-p-xylene[1,1'-bis(2-benzothiazolyldithio)-p-phenylenedimethane], m.p. 141°–142°C recrystallized from dioxane. NMR: 7.7–8.0 mult. (4H); 7.3–7.5 mult. (8H); 4.12 singlet (4H). Another preparation recrystallized twice from toluene analyzes 52.86% C, 2.91% H, 5.69% N and 38.31% S compared to 52.76% C, 3.22% H, 5.59% N and 38.47% S calculated for $C_{22}H_{16}N_2S_6$.

Similarly, reacting α,α'-o-xylenedisulfenyl chloride with 2-mercaptobenzothiazole gives α,α'-bis(2-benzolthiazolyldithio)-o-xylene, a red oil. NMR: 8.0–7.0 mult.; 4.75–4.40 mult.

Using 2-mercapto-4-methylthiazole gives α,α'-bis[2(4-methylthiazolyldithio)]-p-xylene, a tan solid, m.p. 67°–69°C recrystallized from ethanol. NMR: 7.1 singlet (4H); 6.7 mult. (2H); 4.0 singlet (4H); 2.3 singlet (6H).

Using α,α'-m-xylenedisulfenyl chloride as the reactant gives α,α'-bis(2-benzothiazolyldithio)-m-xylene, a tan solid, m.p. 94°–96°C. NMR: 8.0–7.0 mult. (12H); 4.1 singlet (4H).

1,2-Ethanedisulfenyl chloride (0.2 mole) in 120 ml. of benzene is added over a period of one hour to a stirred mixture of 2-mercaptobenzimidazole (60 g., 0.4 mole), pyridine (0.4 mole) and 550 ml. of benzene while the temperature is controlled between 25°–30°C. During the addition, a white precipitate forms. After stirring the mixture two additional hours at room temperature, the precipitate is recovered by filtration. A buff colored solid is obtained, m.p. 250°–275°C, which is the HCl salt of the desired product. The solid is slurried in one liter of water containing 100 grams of sodium bicarbonate and the mixture stirred for one hour. The precipitate is recovered by filtration and washed with water. The material is reslurried in 500 ml. of methanol and the mixture stirred 30 minutes. The product is recovered by filtration to give 67.5 grams of 1,2-bis(2-benzimidazolyldithio)ethane, m.p. 190°–192°C. NMR: 7.1–7.7 mult.; 6.5 broad; 3.42 singlet. Infrared spectral analysis shows no thiocarbonyl, a NH group 3380 cm⁻¹, and S-CH₂ groups 2780 cm⁻¹.

1-Phenylethane-1,2-disulfenyl chloride (0.72 mole) in 50 ml. of benzene is slowly added over one hour to a mixture of 2-mercaptobenzothiazole (23.3 g., 0.14 mole) and 32 ml. of pyridine in 100 ml. of benzene at 25°–30°C. After stirring for two hours at room temperature, the pyridine hydrochloride is separated by filtration and the mixture washed five times with 200 ml. portions of water. The benzene layer is dried over sodium sulfate and evaporated to yield an amber oil. After adding ethyl ether to the oil, 2.3 grams of 2,2-bis benzothiazolyldisulfide is recovered by filtration. The addition of petroleum ether results in an amber oil separating from the mixture. The oil is extracted three times with a mixture of one part ether and two parts petroleum ether. After the last extraction, the residual oil is dried in vacuo to give 12.2 grams of substantially pure 1,2-di(2-benzothiazolyldithio)-1-phenylethane. NMR: 7.0–7.9 mult.; 7.24 singlet; 5.14 triplet; 3.4–3.7 mult.

By a similar procedure 1,1'-bis(chlorosulfenyl)-2,2'-oxydipropane (0.2 mole) prepared from 2-mercaptoisopropyl ether is reacted with 66.8 g. (0.4 mole) of 2-mercaptobenzothiazole and 33 ml. of pyridine in 500 ml. benzene to give 91 grams of 1,1'-bis(2-benzothiazolyldithio)-2,2'-oxydipropane, an amber oil. NMR: 7.58–7.82 mult.; 7.1–7.54 mult.; 3.55–4.06 sextet; 2.98–3.23 mult.; 1.17–1.5 mult.

2-Mercaptobenzothiazole (0.4 mole) is reacted with p-methane-2,9-disulfenyl chloride (0.2 mole) to give 2,9-di(2-benzothiazolyldithio)-p-menthane, a sticky glass. NMR: 7.9–7.0 mult.; 3.5–0.8 mult.

2-Mercaptobenzothiazole (16.7 g., 0.1 mole) and triethylamine (10.1 g., 0.1 mole) dissolved in 100 ml. of benzene is charged into a suitable reactor at room temperature and there is added dropwise while controlling the temperature between 25°–30°C 1,2-n-octanedisulfenyl chloride (0.05 mole) in 50 ml. of benzene. The reaction mixture is stirred for one hour and the triethylamine salt is separated by filtration. The benzene filtrate is washed three times with 200 ml. portions of water and dried over sodium sulfate. The benzene is vacuum stripped at 40°C giving an oil containing a small amount of solid material. Ethyl acetate is added and 1.2 grams of 2-benzothiazole disulfide is removed by filtration. Heptane (250 ml.) is added to the filtrate and the mixture is cooled to yield 16.1 grams of 1,2-di(2-benzothiazolyldithio)-n-octane, a brown oil. NMR: 7.15–7.95 mult. (8H); 2.9–3.5 mult. (3H); 0.86 triplet (3H); 1.0–2.0 mult. (10H).

Similarly, by reacting 1,2-n-hexane disulfenyl chloride, 55 grams of an oil, identified as 1,2-di(2-benzothiazolyldithio)-n-hexane is recovered.

Chlorination of 2-ethyl bicyclo[2.2.1]heptane[5 or 6]dithiol gives the corresponding disulfenyl chloride which is reacted with two molar portions of sodium 2-mercaptobenzothiazole to give 2-[β-(2-benzothiazolyldithioethyl)]-5- or -6-(2-benzothiazolyldithio)bicyclo[2.2.1]heptane of the formula

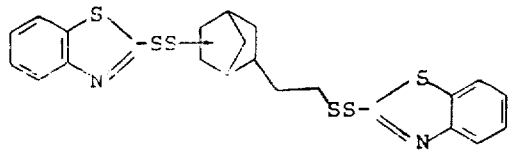

NMR is consistent with the proposed structure.

1,2-Propane disulfenyl chloride (0.1 mole) in about 90 ml. of hexane is added to sodium 2mercaptobenzothiazole (38 grams) in 200 ml. of benzene at 5°–10°C. After warming to room temperature, by-product is removed by filtration and the filtrate evaporated to yield a tan oil. The oil is dissolved in a mixture of toluene and heptane. White crystals slowly precipitate from the solution over a period of several days. Ten grams of 1,2-di(2-benzothiazolyldithio)propane, m.p. 63°–65°C is obtained. NMR: 7.0–8.0 mult. (8H); 3.0–3.6 mult. (3H); 1.5 doublet (3H).

1,3-(2-Hydroxy)-propane disulfenyl chloride, prepared by chlorination of 1,3-dimercapto-2-propanol, in about 270 ml. of dichloroethane is added to a slurry of sodium 2-mercaptobenzothiazole (38 grams) in 100 ml. of dichloroethane at 0°C. The mixture is filtered to remove solid by-product and the filtrate evaporated to yield an oily paste. The paste is slurried in ether, filtered to remove solid by-product, and the ether filtrate is evaporated to give 7.8 grams of a reddish, glassy product which is identified by NMR and infrared analyses as being substantially 1,3-bis(2-benzothiazolyldithio)-2-hydroxypropane.

1,6-Hexanedisulfenyl chloride (0.2 mole) in 150 ml. of carbon tetrachloride is added slowly with stirring over a period of one hour to a solution of 210 g. (0.4 mole) aqueous sodium 2-mercaptobenzothiazole and 250 ml. of benzene. During the addition, the temperature rises from 25° to 37°C. The benzene layer is separated, dried over $Na_2SO_4$ and filtered. The benzene is removed by evaporation to give 80.6 g. of 1,6-bis(2-benzothiazolyldithio)hexane, a dark liquid. Identification is confirmed by nuclear magnetic resonance spectral analysis. NMR: 7.5 mult. (8H); 2.85 triplet (4H); 1.0–1.9 mult. (8H).

1,2-Ethanedisulfenyl chloride (0.05 mole) in 50 ml. of benzene is added at 5°–10°C to a stirred solution of the potassium salt of 2-mercapto-4-phenyl-1,3,4-thiadiazoline-5-thione (26.4 g., 0.10 mole) and 250 ml. of dimethyl formamide. The mixture is stirred for one hour and then held overnight at room temperature. Water (1500 ml.) is added to dissolve the salt. The yellow solid is collected by filtration, washed with water and dried. 1,2-bis[2(4-phenyl-5-thioxo)-1,3,4-thiadiazolinyldithio]ethane (23 g.), m.p. 158°–160°C recrystallized from dimethylsulfoxide, is obtained. NMR: 7.5 mult.; 3.1 singlet.

The following example illustrates the preparation of cross-linking agents containing a xanthogen accelerating moiety. 1,2-Ethanedisulfenyl chloride (0.1 mole) in 100 ml. of benzene is added at room temperature to 34.8 g. (0.2 mole) of potassium isopropyl xanthate in 250 ml. of dimethylformamide. After adding one liter of water, the reaction mixture is extracted with benzene. The benzene extract is dried over $Na_2SO_4$ and the benzene is removed by evaporation to give a yellow oil which solidifies within a few minutes. The solid is rinsed with heptane and dried to give 16 grams of 1,2-bis(isopropoxythiocarbonyldithio)ethane, a white solid, m.p. 66°C. NMR: 5.8 septet (2H); 3.1 singlet (4H); 1.5 doublet (12H). Chemical analysis gives 32.97% C, 5.09% H, and 52.40% S compared to 33.12% C, 5.00% H and 53.05% S calculated for $C_{10}H_{18}O_2S_6$.

1,2-Bis[2(4,6-dimethylpyrimidinyl)dithio]ethane is prepared by adding 0.1 mole of 1,2-ethanedisulfenyl chloride in 100 ml. of benzene at room temperature to 28 grams (0.2 mole) of 2-mercapto-4,6-dimethylpyridine and 20 g triethylamine in 200 ml. of benzene. The precipitate is collected by filtration, washed with water and dried. 1,2-Bis[2(4,6-dimethylpyrimidinyl)dithio]ethane, m.p. 125°–128°C recrystallized from heptane is recovered. NMR: 6.65 singlet (2H); 3.2 singlet (4H); 2.2 singlet (12H).

A solution of 1,2-ethanedisulfenyl chloride (0.1 mole) in 100 ml. of benzene is added dropwise over a period of one hour at 25°–30°C to a stirred solution containing 2-mercaptopyridine (0.2 mole) and triethylamine (0.2 mole) in 100 ml. of benzene. After stirring one hour, the mixture is filtered and the filter cake washed with 300 ml. of benzene. The benzene filtrate is washed three times with 100 ml. portions of water and then dried over $Na_2SO_4$. The benzene is evaporated under vacuum at 40°C to yield 22 grams of a red oil. The oil is precipitated twice from methylene chloride to give 16.3 grams of 1,2-bis(2-pyridinyldithio)ethane. NMR: 8.37–8.6 mult. (1H); 7.55–7.75 mult. (2H); 6.95–7.25 mult. (1H); 3.12 singlet (2H).

While controlling the temperature between 25°–30°C, 2,4-dinitrobenzenesulfenyl chloride 46.9 g. (0.2 mole) is added over 42 minutes to a solution of ethanedithiol 9.4 g. (0.1 mole) and 16 ml. of pyridine and 250 ml. of benzene. The bright red slurry slowly changes to an orange color as the addition proceeds. After stirring two hours, the precipitate is recovered by filtration, washed with water and air dried. 56.3 grams of an orange solid m.p. 212°–220°C is obtained. The solid is slurried in a solution of 50 grams sodium bicarbonate and 300 ml. of $H_2O$ and filtered to give a lighter colored solid. The solid is reslurried in 200 ml. of methanol and recovered by filtration to give 45.5 grams of 1,2-bis(2,4-dinitrophenyldithio)ethane, a yellow solid, m.p. 232°–235°C. A number of bis(dinitrophenyldithio)alkane compounds suitable for the practice of this invention are described in J. Org. Chem., 20 50 (1955).

Similarly, 2,4-dinitrobenzenesulfenyl chloride is reacted with 1-phenylethane-1,2-dithio to give 83% yield of 1,2-di(2,4-dinitrophenyldithio)-1-phenylethane, m.p. 136°–138°C.

A di-Bunte salt is prepared by refluxing for one hour a mixture comprising sodium thiosulfate (31.6 g., 0.2 mole) in 100 ml. of water and dibromoethane (18.8 g., 0.1 mole) in 100 ml. of ethanol. The di-Bunte salt solution while still hot is added in small portions over 10 minutes to a slurry of 2-mercapto-4,6-diallylamino-s-triazine (44.6 g., 0.2 mole) and 10 g. (0.25 mole) sodium hydroxide in 300 ml. of water. During the addition the temperature of the mixture rises from 25° to 40°C. The mixture is stirred at 40°C for 1.5 hours after which it is filtered to remove 6 grams of unreacted triazine. 120 Grams of sodium chloride is dissolved in the filtrate and the mixture allowed to stand overnight. A white solid, 24 grams, is recovered by filtration. The solid is dissolved in hot chloroform, and the solution concentrated by evaporation of the solvent. The addition of 100 ml. of methanol precipitates a crystalline white solid which is recovered. After drying, 12 grams of a white solid, m.p. 156°–157°C, believed to be the monohydrate of 1,2-[2(4,6-di[diallylamino])-s-triazinyldithio]ethane is recovered. Chemical analysis gives 44.29% C, 5.35% H, 25.73% N, 22.96% S and 1.04% O compared to 43.35% C, 5.41% H, 25.25% N, 23.10% S and 2.89% O calculated for $C_{20}H_{30}N_{10}OS_4$. Molecular weight found 566 (554 theory).

Reacting 1,2-ethanedisulfenyl chloride in benzene with 2-mercapto-4,6-dipropylamino-s-triazine in water yields a white solid, m.p. 147°–149°C believed to be the monohydrate of 1,2-bis[2(4,6-di[dipropylamino])-s-triazinyldithio]ethane. Chemical analysis gives 42.99% C, 6.70% H, 25.33% N, 20.91% S, and 2.16% O compared to 42.70% C, 6.76% H, 24.94% N, 22.80% S and 2.80% O calculated for C₂₀H₃₈N₁₀OS₄. Molecular weight found 564 (562 theory).

Chlorocarbonylsulfenylchloride, C.A. 65, 12112 (1966), 26.2 g. in 100 ml. of benzene is added at room temperature to 9.4 g. ethanedithiol. HCl evolves during the addition. A white precipitate forms a morpholine (35 grams) is added to the reaction mixture. The white solid is recovered by filtration, washed well with water and air dried. 1,2-Bis(morpholinocarbonyldithio)ethane

m.p. 178°–179°C is obtained. NMR: 4.6 singlet; 3.0 singlet. The product is soluble in hot toluene, alcohol, dimethylformamide and ethyl acetate.

Chlorocarbonylsulfenylchloride (12.2 g. in 50 ml. benzene) is added to 4.3 grams of ethanol and the mixture heated at 50°C for one hour. Ethanedithiol (4.4 g. in 50 ml. benzene) is added with evolution of HCl. The solvent is vacuum stripped to yield a tan oil identified as 1,2-bis(ethoxycarbonyldithio)-ethane

NMR: 4.35 quartet; 3.1 singlet; 1.35 triplet, J=8 cps.

3,4-Toluenedisulfenylchloride is prepared by adding 4.7 grams of chlorine dissolved in 100 ml. of CCl₄ to a solution of 3,4-toluenedithiol in 50 ml. of CCl₄. The disulfenyl chloride is added at room temperature to 11 grams of 2-mercaptobenzothiazole and 6.7 grams of triethylamine. The mixture is filtered and the benzene evaporated to give 11 grams of 3,4-di(2-benzothiazolyldithio)toluene, a red solid, m.p. 125°–140°C. NMR: 7.0–8.0 mult. (11H); 2.3 singlet (3H).

The tetrasulfenyl chloride of pentaerythritol tetra(3-mercaptopropionate) is prepared by reacting chlorine with 48.8 g. (0.1 mole) of the propionate in 500 ml. of benzene. One half of the sulfenyl chloride solution is added to a slurry of 2-mercaptobenzothiazole (33 g.) and triethylamine (20 g.) in 300 ml. of benzene. The temperature rises to 35°C upon the addition. The amine salt is removed by filtration and the filtrate is evaporated to give a yellow glass. The solid is redissolved in 100 ml. of benzene and filtered to remove residual amine salt. The clear solution is evaporated to give a yellow glassy solid identified as substantially pure tetra(2-benzothiazolyldithio)pentaerythritol propionate,

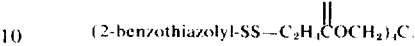

NMR: 7.8–7.2 mult. (4H); 4.17 singlet (2H); 3.3–2.7 quartet (4H).

A solution (65 ml., 0.05 mole) of 2-benzothiazolylsulfenyl chloride in 1,2-dichloroethane is added to 6.7 g. of 1,3-diphenyl 2,2-dithiolpropane, J. Am. Chem. Soc., 81, 3148 (1959), in 50 ml. of 1,2-dichloroethane. Hydrogen chloride evolves during the addition. The mixture is stirred for three hours and the liquid evaporated to give 2,2-bis(2-benzothiazolyldithio)-1,3-diphenylpropane, a yellow glassy solid. NMR: 7.8–7.0 mult. (21H); 3.4 singlet (4H).

3-Chloro-1,2,4-thiadiazol-5-ylsulfenyl chloride, J. Org. Chem., 36, 14 (1971), is added at 0°C to ethanedithiol (9.4 g.) and triethylamine (20 g.) in 50 ml. of methylene chloride. The mixture is filtered to give a yellow solid, washed with water and air dried. 1,2-Bis[5(3-chloro-1,2,4-thiadiazolyldithio)]ethane, m.p. 156°–157°C is obtained. Chemical analysis gives 14.08% N and 48.17% S compared to 14.16% N and 48.65% calculated for C₆H₄Cl₂N₄S₆.

A typical preparation of cross-linking agents of the formula

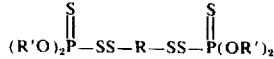

comprises combining polysulfenyl chloride and the amine or sodium salt of an O,O'-dialkylphosphorodithioic acid. Solid products are recovered by filtration. Liquid products are recovered by extraction and evaporation of the organic solvent. Compounds prepared by this procedure are shown in Table II. They are also prepared from (R'O)₂P(S)SH and a Bunte salt as described by Lorenz U.S. patent 3,035,082, May 15, 1962 who prepared (C₂H₅O)₂P(S)SSCH₂-SS(S)P(OC₂H₅)₂ from sodium thiosulfate, methylene bromide and (C₂H₅O)₂P(S)SH.

TABLE II

| Compound | Melting Point, °C | NMR |
|---|---|---|
| 1,2-bis(O,O'-diethylphosphoro-trithioyl)ethane[1] | 54–57 | 4.2 mult.; 3.2 singlet; 1.35 triplet; J=7 cps. |
| 1,2-bis(O,O'-diisopropylphos-phorotrithioyl)ethane[2] | 60–61 | 4.83 mult. (4H); 3.21 singlet (4H); 1.36 doublet (24H) |
| α,α'-bis(O,O'-diisopropylphos-phorotrithioyl-p-xylene | 97–99 | 7.3 singlet (4H); 4.9 mult. (4H); 4.2 doublet (4H); 1.4 doublet (24H) |
| α,α'-di(O,O'-diisopropylphos-phorotrithioyl)-o-xylene | Red Oil | 7.2 mult. (4H); 4.8 mult.; 4.2 doublet (3H); 1.5 doublet (22H) |
| α,α'-bis(O,O'-di-n-butylphos-phorotrithioyl)-p-xylene | Pink Liquid | 7.2 mult. (4H); 4.1 mult. (12H); 2.0–1.0 mult. (28H) |
| 2,9-di(O,O'-diisopropylphos-phorotrithioyl)-p-menthane | Yellow Oil | 4.9 mult.; 1.4 doublet; 3.0–1.0 mult. |
| 1,2-di(O,O'-diethylphosphoro-trithioyl)-n-octane | Dark Brown | 3.9–4.6 mult. (8H); 2.9–3.5 mult. (3H); |

TABLE II-continued

| Compound | Melting Point, °C | NMR |
|---|---|---|
| 1,2-bis(O,O'-di-n-butylphosphorotrithioyl)ethane[3] | Liquid<br>Green Liquid | 0.9 triplet (3H); 1.0-2.0 mult.; 1.4 triplet (22H)<br>4.2 mult. (8H); 3.2 singlet (4H); 1.0-2.0 mult. (30H) |
| 1,2-di(O,O'-diethylphosphorotrithioyl)-n-hexane | Red Liquid | 3.9-4.5 mult. (8H); 2.9-3.5 mult. (3H); 1.4 triplet (12H); 1.15-1.9 mult. (16H); 0.92 triplet (3H) |
| trans-1,2-di(O,O'-diisopropylphosphorotrithioyl)-cyclohexane | Yellow Liquid | 4.5-5.2 heptet (4H); 3.2-3.5 mult. singlet (4H); 1.39 doublet; 0.9-2.0 mult. (32H) |
| 1,2-bis(O,O'-diethylphosphorotrithioyl)-p-xylene | 60-62 | 7.25 singlet (4H); 4.08 doublet (4H); 3.92-4.5 mult. (8H); 1.38 triplet (12H) |
| 1,2-di(O,O'-diisopropylphosphorotrithioyl)-1-phenylethane | Yellow Oil | 7.2-7.38 mult. (5H); 5.17 triplet (1H); 3.85 heptet (2H); 3.45-3.8 mult. (2H); 1.37 doublet (12H) |
| 1,2-di(O,O'-diethylphosphorotrithioyl)-1-phenylethane | Yellow Liquid | 7.27-7.47 mult. (5H); 5.23-5.27 triplet (1H); 3.4-3.8 mult. (2H); 3.9-4.6 mult. (8H); 1.36 triplet (12H) |
| 2[β-(O,O'-diethylphosphorotrithioylethyl)]-5- or -6-(O,O'-diethylphosphorotrithioyl)-bicyclo(2.2.1)-heptane | Yellow Oil | 3.9-4.5 quintet (8H); 2.7-3.2 broad peak (3H); 0.6-2.5 broad peak; 1.36 triplet (23H) |
| α,α'-bis(O,O'-di-sec-butylphosphorotrithioyl)-p-xylene | 83-85 | 7.3 singlet (4H); 5.0-4.5 sextet (4H); 4.2 doublet (4H); 1.3-2.0 mult.-1.4 doublet (20H); 0.95 triplet (12H) |
| α,α'-bis(O,O'-diisobutylphosphorotrithioyl)-p-xylene | 58-60 | 7.3 singlet (4H); 4.1 doublet-4.0-3.8 mult. (12H); 2.3-1.7 septet (4H); 0.95 doublet (24H) |
| α,α'-bis(O,O'-dicyclohexylphosphorotrithioyl)-p-xylene | 93-96 | 7.3 singlet (4H); 4.9-4.4 mult. (4H); 4.2 doublet (4H); 2.0-1.0 mult. (20H) |
| α,α'-bis(O,O'-di-2-ethylhexylphosphorotrithioyl)-p-xylene | Brown Oil | 7.2 singlet (4H); 4.1-3.9 mult. (12H); 1.6-0.6 mult. (60H) |
| α,α'-bis(O,O'-di-n-hexylphosphorotrithioyl)-p-xylene | Amber Oil | 7.2 singlet (4H); 4.2-4.0 mult. (12H); 1.9-0.7 mult. (44H) |

[1]Chemical analysis gives 26.44% C and 5.35% H compared to 25.96% C and 5.23% H calculated for $C_{10}H_{24}O_4P_2S_6$.

[2]Chemical analysis gives 32.49% C, 6.47% H, 36.84% S and 11.73% P compared to 32.41% C, 6.22% H, 37.09% S and 11.94% P calculated for $C_{14}H_{32}O_4P_2S_6$.

[3]This compound is prepared by reacting 1,2-ethanedisulfenyl chloride with an equal molar quantity of zinc O,O'-di-n-butylphosphorodithioate and removing the zinc chloride by-product by dissolution in water.

The reaction of a bis-sulfenyl chloride with a mixture of two different thiols gives mixtures comprising cross-linking agent having the same accelerating moieties and a portion of cross-linking agents having a different accelerating moiety on each end of the molecule. To illustrate the preparation of mixed cross-link agents, one-third portions of a 1,2-ethanedisulfenyl chloride solution prepared by reacting chlorine with 56.4 grams ethanedithiol are reacted with a thiol mixture comprising various proportions of 2-mercaptobenzothiazole and the triethylamine salt of ethyl phosphorodithioate. The amount of reactants used and the ratio of products obtained are shown below:

| | MIXED CROSS-LINKING AGENTS | | | |
|---|---|---|---|---|
| Experiment | Reactant | Amount Grams | Product | Mole Fraction |
| A | BT—SH | 16.7 | $[(C_2H_5O)_2\overset{S}{\overset{\|}{P}}SSCH_2]_2$ | 9 |
| | $(C_2H_5O)_2\overset{S}{\overset{\|}{P}}$—SH | 55.8 | $(BT-SS-CH_2)_2$ | 1 |
| | | | $(C_2H_5O)_2\overset{S}{\overset{\|}{P}}SSC_2H_4SS-BT$ | 6 |

-continued

MIXED CROSS-LINKING AGENTS

| Experiment | Reactant | Amount Grams | Product | Mole Fraction |
|---|---|---|---|---|
| B | BT—SH | 33.4 | $[(C_2H_5O)_2\overset{S}{\overset{\|}{P}}SSCH_2]_2$ | 1 |
|  | $(C_2H_5O)_2\overset{S}{\overset{\|}{P}}$—SH | 37.2 | $(BT—SS—CH_2)_2$ | 1 |
|  |  |  | $(C_2H_5O)_2\overset{S}{\overset{\|}{P}}SSC_2H_4SS—BT$ | 2 |
| C | BT—SH | 50.1 | $[(C_2H_5O)_2\overset{S}{\overset{\|}{P}}SSCH_2]_2$ | 1 |
|  | $(C_2H_5O)_2\overset{S}{\overset{\|}{P}}$—SH | 18.6 | $(BT—SS—CH_2)_2$ | 9 |
|  |  |  | $(C_2H_5O)_2\overset{S}{\overset{\|}{P}}SSC_2H_4SS—BT$ | 6 |

BT = 2-benzothiazolyl

The reaction of α,α'-p-xylenesulfenyl chloride and the salt of O,O'-diphenylphosphorodithioic acid gives α,α'-bis(O,O'-diphenylphosphorotrithioyl)-p-xylene.

One half (0.05 mole) of the tetra-sulfenyl chloride of pentaerythritol 3-mercaptopropionate, as previously prepared, is added to a slurry of ethyl phosphorodithioate, 37 g., and triethylamine, 20 g., in 200 ml. of benzene at room temperature. The temperature rises slightly and a white precipitate forms. The triethylamine salt is separated by filtration and the filtrate evaporated to give 57 grams of tetra(O,O'-diethyl phosphorotrithioyl)pentaerythritol propionate,

a pale oil. NMR: 4.5–3.9 mult., 3.2–3.7 quartet, 1.4 triplet.

Bis-trisulfides are prepared by reacting two molar proportions of sulfur dichloride with a dithiol to yield bis-thiosulfenyl chloride which is then reacted with a salt of Acc-SH, such as, a salt of a dithiocarbamic acid, a salt of a mercaptoazole, or a salt of a dithiophosphoric acid to give the desired bis-trisulfide. Dithiocarbamate derivatives are prepared as follows:

To a reactor containing 56.6 g. (0.55 mole) of sulfur dichloride at −78°C there is added slowly over a 25 minute period 23.5 g. (0.25 mole) of 1,2-ethanedithiol in 25 ml. of ether. The mixture is allowed to slowly warm to room temperature and the reactor is evacuated to remove by-product HCl. In a separate reactor, the triethylamine salt of N,N-diethyl dithiocarbamic acid is prepared by adding dropwise at room temperature 38.0 g. (0.50 mole) of carbon disulfide to a solution containing diethylamine (36.5 g.; 0.50 mole) and triethylamine (50.5 g.; 0.50 mole) in 100 ml. of hexane. After stirring for 30 minutes, the hexane layer is separated from the dithiocarbamic acid salt which salt is used in the next reaction sequence. The dithiocarbamic acid salt is added over a 30 minute period to the reactor containing the bis-1,2-ethane thiosulfenyl chloride at room temperature. The reactor is kept cool by a water bath maintained at room temperature. After stirring the mixture for 90 minutes, one liter of benzene and 400 ml. of water are added. The benzene layer is separated, dried over Na$_2$SO$_4$ and vacuum stripped to yield 86 g. (76% yield) of a brown oil identified as 1,2-bis(N,N-diethylthiocarbamoyltrithio)ethane containing a minor amount of unidentified by-products. NMR: 3.7–4.2 mult. (4H); 3.1–3.5 mult. (2H); 1.32 triplet (6H).

In a similar manner by substituting dimethylamine in the above procedure, 1,2-bis(N,N-dimethylthiocarbamoyltrithio)ethane, a gummy solid, is obtained.

To 47 g. (0.2 mole) of the amine salt of 1,1-dimethyldithiocarbazinic acid slurried in 200 ml. of benzene, there is added 1,2-ethanedisulfenyl chloride (0.1 mole) in 100 ml. of benzene at room temperature. The temperature rises as the amine salt is added and a white solid forms. After cooling the mixture, the white solid is removed by filtration, washed with water and dried. Thirty grams of 1,2-bis(N,N-dimethylaminothiocarbamoyldithio)ethane,

m.p. 105°C, is obtained.

Cross-Linking Rubber

The vulcanization of rubber with the cross-linking agents of this invention is demonstrated with the following rubber masterbatches. All parts are by weight. Santoflex 13, an antidegradant, is N-1,3-dimethylbutyl-N'-phenyl-p-phenylenediamine; Flectol H, an antidegradant, is polymerized 1,2-dihydro-2,2,4-trimethylquinoline and Santocure NS, an accelerator, is N-tert-butyl-2-benzothiazolesulfenamide.

MASTERBATCHES

| A. Natural Rubber | 100.0 | B. Oil-extended SBR | 137.5 |
|---|---|---|---|

MASTERBATCHES-continued

| | | | | | |
|---|---|---|---|---|---|
| ISAF Carbon Black | 45.0 | | ISAF Carbon Black | 65.0 | |
| Zinc Oxide | 3.0 | | Zinc Oxide | 3.0 | |
| Stearic Acid | 2.0 | | Stearic Acid | 1.0 | |
| Hydrocarbon Softener | 5.0 | | Hydrocarbon Softener | 1.5 | |
| Santoflex 13 | 2.0 | | Santoflex 13 | 2.0 | |
| | 157.0 | | | 210.0 | |
| C. cis-4-Polybutadiene | 100.0 | D. | Butadiene Acrylo- | 100.0 | |
| HAF Carbon Black | 90.0 | | nitrile rubber | | |
| Highly Aromatic Oil | 50.0 | | FEF Carbon Black | 55.0 | |
| Zinc Oxide | 3.0 | | Dioctyl Phthalate | 10.0 | |
| Stearic Acid | 1.5 | | Flectol H | 2.0 | |
| | 244.5 | | Zinc Oxide | 5.0 | |
| | | | Stearic Acid | 1.0 | |
| | | | | 173.0 | |
| E. Butyl Rubber | 100.0 | F. | Ethylene-propylene- | 100.0 | |
| ISAF Carbon Black | 40.0 | | diene terpolymer | | |
| Zinc Oxide | 5.0 | | FEF Carbon Black | 80.0 | |
| Stearic Acid | 1.0 | | Naphthenic Oil | 40.0 | |
| Hydrocarbon Softener | 10.0 | | Zinc Oxide | 5.0 | |
| | 156.0 | | Stearic Acid | 1.0 | |
| | | | | 226.0 | |
| G. Polyisoprene Rubber | 100.0 | H. | Chlorobutyl Rubber | 100.0 | |
| ISAF Carbon Black | 45.0 | | HAF Carbon Black | 50.0 | |
| Zinc Oxide | 3.0 | | Stearic Acid | 1.0 | |
| Stearic Acid | 2.0 | | | 151.0 | |
| Aromatic Oil | 5.0 | | | | |
| | 155.0 | | | | |
| I. Neoprene W Rubber | 100.0 | J. | Chlorosulfonated | 100.0 | |
| SRF Carbon Black | 30.0 | | polyethylene | | |
| MT Carbon Black | 40.0 | | (Hypalon 40) | | |
| Naphthenic Oil | 10.0 | | SRF Carbon Black | 30.0 | |
| | 180.0 | | MT Carbon Black | 40.0 | |
| | | | Naphthenic Oil | 15.0 | |
| | | | | 185.0 | |

The data of Table III illustrates the cross-linking properties of 1,2-bis(thiocarbamoyldithio)ethanes in natural rubber. Three parts of the cross-linking agents are tested with 157 parts of Masterbatch A. Stock 1 is a control with 2.0 parts sulfur and 0.5 parts Santocure NS as accelerator.

The data demonstrate that the cross-linking agents, in the absence of sulfur or an accelerator, cross-link rubber and produce vulcanizates having satisfactory physical properties. The stocks containing the cross-linking agents have greater processing safety, as indicated by the Mooney Scorch values, than the stock

TABLE III $$R_2N\overset{S}{\overset{\|}{C}}SSCH_2CH_2SS\overset{S}{\overset{\|}{C}}NR_2$$

| Stock | 1 | 2 | 3 | 4 | 5 | 6 | 7 | 8 | 9 |
|---|---|---|---|---|---|---|---|---|---|
| $R_2N-$ | — | $(CH_3)_2N-$ | $(C_2H_5)_2N-$ | $(iC_3H_7)_2N-$ | $\begin{array}{c}C_2H_5\\C_4H_9\end{array}\!\!>\!\!N-$ | $\begin{array}{c}C_3H_7\\C_6H_{11}\end{array}\!\!>\!\!N-$ | 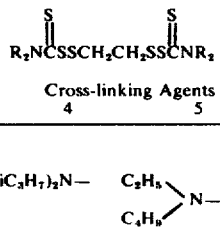 |  |  |
| Mooney Scorch at 121°C | | | | | | | | | |
| $t_5$, min. | 32.0 | 41.0 | 60.1 | 87.5 | 57.6 | 66.1 | 62.0 | 53.3 | 89.0 |
| Rheometer Data at 144°C | | | | | | | | | |
| $t_{90}-t_2$, min. | 12.6 | 32.5 | 33.7 | 45.6 | 43.3 | 39.2 | 35.3 | 37.5 | 31.7 |
| R Max. | 66.0 | 64.2 | 57.6 | 46.0 | 47.6 | 39.2 | 53.1 | 55.0 | 54.0 |
| R Min. | 26.0 | 24.3 | 25.7 | 25.6 | 25.6 | 25.2 | 25.6 | 25.6 | 24.8 |
| Rheometer Data at 164°C | | | | | | | | | |
| $t_{90}-t_2$, min. | 3.9 | 8.7 | 9.7 | 8.0 | 11.5 | 10.0 | 8.5 | 9.7 | 5.4 |
| R Max. | 64.0 | 60.7 | 48.0 | 34.6 | 38.0 | 26.6 | 48.0 | 51.3 | 47.3 |
| R Min. | 6.0 | 5.9 | 2.8 | 2.7 | 2.1 | 2.9 | 5.4 | 6.4 | 6.6 |
| Reversion (10 min.) | 11.2 | 0.0 | 0.0 | 0.0 | 0.0 | 0.0 | 0.0 | 0.0 | 0.0 |
| Stress-Strain Data at 144°C | | | | | | | | | |
| Cure Time, min. | 30 | 120 | 120 | 120 | 120 | 90 | 120 | 120 | 90 |
| 300% Modulus, psi | 1450 | 1530 | 1240 | 940 | 860 | 580 | 1200 | 1290 | 1190 |
| Ult. Tensile Strength, psi | 3840 | 2540 | 2240 | 3250 | 3300 | 2400 | 3750 | 3650 | 3350 |
| Ult. Elongation, % | 550 | 400 | 420 | 600 | 620 | 600 | 600 | 580 | 550 | containing sulfur and sulfenamide accelerator. The added processing safety is a valuable property which in many applications will eliminate the need for prevulcanization inhibitors. The rheometer data at 164°C illustrate the stability of the vulcanizates produced with the cross-linking agents of this invention. The sulfur cured stock loses 11 rheometer torque units by heating the vulcanizate 10 minutes beyond the time when the maximum cure is obtained, whereas in the other stocks no loss in rheometer torque is observed. The reversion resistance of the stocks containing the cross-linking agents of this invention permits the use of higher curing temperatures while minimizing the loss of modulus due to overcure. On the other hand, stocks (not shown) containing 3 parts of 1,2-bis(thiocarbamoylthio)ethanes failed to cure.

The data of Table IV compares the properties of bis(thiocarbamoyldithio)alkanes at three parts in 157 parts of Masterbatch A.

The data show that increasing the size of the alkylene bridge does not materially affect the cross-linking properties. The surprising result is the relatively weak cross-linking ability of the cross-linking agent having a morpholino amine moiety. The result is unexpected and difficult to explain particularly in view of the efficacy of other heterocyclic amine moieties as shown in Table III.

Table V illustrates the properties of 1,2-bis-(thiocarbamoyldithio) ethanes in styrene-butadiene copolymer rubber. Three parts of the cross-linking agent is tested with 208 parts of Masterbatch B. Stock 1 is a control with 2.0 parts sulfur and 1.0 parts Santocure NS as accelerator. The data demonstrate that the cross-linking agents produce satisfactory vulcanizates with synthetic rubber. The rheometer data at 173°C illustrate the vulcanizates produced with the bis-disulfides are resistant to reversion.

TABLE IV $$R_2NCSS-X-SSCNR_2$$
(with S double-bonded to each C)

| Stock | Cross-linking Agents | | | | | |
|---|---|---|---|---|---|---|
| | 1 | 2 | 3 | 4 | 5 | 6 |
| $R_2N-$ | $(CH_3)_2N-$ | $(CH_3)_2N-$ | 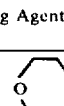 | 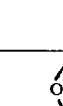 | 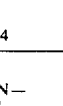 | 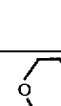 |
| $-X-$ | $-C_2H_4-$ | $-C_2H_4OC_2H_4-$ | $-C_2H_4-$ | $-C_2H_4OC_2H_4-$ |  | $-(CH_2)_6-$ |
| Mooney Scorch at 121°C | | | | | | |
| $t_5$, min. | 33.9 | 38.7 | 132.9 | 97.5 | 91.0 | — |
| Rheometer Data at 144°C | | | | | | |
| $t_{90}-t_2$, min. | 20.4 | 18.1 | 24.0 | 15.4 | 12.5 | — |
| R Max. | 55.2 | 46.7 | 22.3 | 21.4 | 19.0 | — |
| R Min. | 12.4 | 12.7 | 12.7 | 13.3 | 3.0 | — |
| Rheometer Data at 164°C | | | | | | |
| $t_{90}-t_2$, min. | — | — | — | — | — | 4.8 |
| R Max. | — | — | — | — | — | 16.0 |
| R Min. | — | — | — | — | — | 0.8 |
| % Reversion | — | — | — | — | — | 0 |
| Stress-Strain Data at 144°C | | | | | | |
| Cure Time, minutes | 60 | 60 | 60 | 60 | 40 | — |
| 300% Modulus, psi | 1700 | 1450 | 390 | 280 | 250 | — |
| Ult. Tensile, psi | 2190 | 2800 | 940 | 660 | 1040 | — |
| Ult. Elongation, % | 320 | 450 | 450 | 450 | 530 | — |

TABLE V $$R_2NCSS-X-SSCNR_2$$
(with S double-bonded to each C)

| Stock | Cross-linking Agents | | | | | |
|---|---|---|---|---|---|---|
| | 1 | 2 | 3 | 4 | 5 | 6 |
| $R_2N-$ | — | $(CH_3)_2N-$ | $(CH_3)_2N-$ | 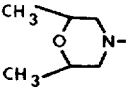 |  |  |
| $-X-$ | — | $-C_2H_4-$ | $-C_2H_4OC_2H_4-$ | $-C_2H_4-$ | $-C_2H_4-$ | $-C_2H_4-$ |
| Mooney Scorch Data at 135°C | | | | | | |
| $t_5$, min. | 17.5 | 9.8 | 21.9 | 14.9 | 11.4 | 14.7 |
| Rheometer Data at 153°C | | | | | | |
| $t_{90}-t_2$, min. | 17.5 | 11.2 | 12.8 | 16.6 | 17.0 | 17.3 |
| R Max. | 51.6 | 47.1 | 34.2 | 35.0 | 35.5 | 37.1 |
| R Min. | 8.0 | 8.8 | 7.8 | 7.7 | 8.0 | 8.0 |
| Rheometer Data at 173°C | | | | | | |
| $t_{90}-t_2$, min. | 5.4 | 3.3 | 7.7 | 4.6 | 5.6 | 10.0 |
| R Max. | 46.0 | 41.6 | 31.1 | 30.5 | 31.3 | 36.4 |
| R Min. | 8.0 | 8.7 | 7.8 | 7.7 | 8.4 | 8.0 |
| Reversion (10 min.) | 1.8 | 0.0 | 0.0 | 0.0 | 0.0 | 0.0 |
| Stress-Strain Data at 153°C | | | | | | |
| Cure Time, minutes | 45 | 45 | 60 | 60 | 60 | 60 |
| 300% Modulus, psi | 1080 | 950 | 510 | 500 | 600 | 600 |
| Ult. Tensile Strength, psi | 3150 | 1410 | 1750 | 2480 | 2540 | 2490 |

TABLE V-continued $$R_2N\overset{S}{\overset{\|}{C}}SS-X-SS\overset{S}{\overset{\|}{C}}NR_2$$

Cross-linking Agents

| Stock | 1 | 2 | 3 | 4 | 5 | 6 |
|---|---|---|---|---|---|---|
| Ult. Elongation, % | 600 | 420 | 650 | 800 | 720 | 700 |

Table VI demonstrates the cross-linking of stocks comprising various elastomers and shows the applicability to diene and specialty rubbers. Three parts of 1,2-bis(N,N-dimethylthiocarbamoyldithio) ethane is added to the amount of each masterbatch shown except for Stock 6 wherein four parts are added. Similar stocks containing sulfur as an additional ingredient give substantially higher states of cure. Similarly, substantial cross-linking is observed in the above masterbatches illustrate the use of the cross-linking agent with sulfur. Increasing the amount of sulfur reduces the processing safety and increases the cure rate and state of cure. Comparison of Stocks 2–4 with 5–7 indicates that vulcanizates having comparable physical properties can be obtained either by using the cross-linking agent alone or by using a combination of sulfur and cross-linking agent. However, the stocks containing cross-linking agents alone have greater reversion resistance.

TABLE VI

| Stock | 1 | 2 | 3 | 4 | 5 | 6 | 7 | 8 |
|---|---|---|---|---|---|---|---|---|
| Masterbatch | C | D | E | F | G | H | I | J |
| Parts | 244.5 | 173.0 | 156.0 | 226.0 | 155.0 | 151.0 | 180.0 | 185.0 |
| Mooney Scorch | | | | | | | | |
| Temp., °C | 121 | 135 | 135 | 135 | 121 | 121 | 121 | 121 |
| $t_s$, min. | 27.3 | 21.5 | 15.6 | 20.0 | 22.6 | >120 | 39.7 | 24.1 |
| Rheometer Data | | | | | | | | |
| Temp., °C | 153 | 163 | 153 | 160 | 153 | 153 | 153 | 153 |
| $t_{90}-t_2$, min. | 16.2 | 17.0 | 18.7 | 17.9 | 18.2 | 78.0 | 93.6 | 20.1 |
| R Max. | 65.3 | 31.8 | 32.9 | 20.6 | 74.0 | 28.7 | >32.0 | 20.8 |
| R Min. | 26.6 | 13.0 | 24.7 | 13.8 | 26.9 | 6.6 | 5.8 | 1.2 |
| Stress-Strain Data | | | | | | | | |
| Temp., °C | 153 | 163 | 153 | 160 | 153 | 153 | 153 | 153 |
| Cure Time, min. | 60 | 60 | 60 | 50 | 60 | 120 | 120 | 40 |
| 300% Modulus, psi | 840 | 1350 | 90 | 260 | 1440 | 900 | 280 | 1450 |
| Ult. Tensile, psi | 1920 | 2360 | 1650 | 390 | 4000 | 1810 | 1740 | 1680 |
| Ult. Elongation, % | 550 | 510 | 950 | 540 | 550 | 500 | 550 | 360 |

TABLE VII

| Stock | 1 | 2 | 3 | 4 | 5 | 6 | 7 |
|---|---|---|---|---|---|---|---|
| Masterbatch A | 157.0 | | | | | | |
| 1,2-bis(N,N-dimethyl-thiocarbamoyl-dithio)ethane | 1.0 | 2.0 | 3.0 | 4.0 | 1.0 | 1.0 | 1.0 |
| Sulfur | — | — | — | — | 0.3 | 1.0 | 1.7 |
| Mooney Scorch at 121°C | | | | | | | |
| $t_s$, min. | 59.8 | 54.1 | 53.2 | 55.3 | 44.0 | 32.1 | 25.7 |
| Rheometer Data at 144°C | | | | | | | |
| $t_{90}-t_2$, min. | 32.0 | 38.5 | 23.9 | 22.7 | 17.4 | 5.5 | 4.1 |
| R Max. | 16.5 | 37.0 | 55.0 | 66.0 | 37.6 | 55.9 | 68.7 |
| R Min. | 4.8 | 4.0 | 4.2 | 4.5 | 5.7 | 5.8 | 5.3 |
| Rheometer Data at 154°C | | | | | | | |
| $t_{90}-t_2$, min. | 18.9 | 24.3 | 19.4 | 17.7 | 9.4 | 3.1 | 2.2 |
| R Max. | 13.9 | 35.8 | 53.5 | 65.6 | 23.0 | 52.2 | 65.4 |
| R Min. | 4.0 | 4.8 | 4.7 | 4.7 | 5.8 | 6.0 | 5.8 |
| Rheometer Data at 164°C | | | | | | | |
| $t_{90}-t_2$, min. | 10.3 | 14.1 | 12.7 | 10.8 | 3.5 | 1.3 | 1.3 |
| R Max. | 12.2 | 30.0 | 49.0 | 61.2 | 28.9 | 46.3 | 60.7 |
| R Min. | 4.5 | 4.2 | 4.0 | 4.2 | 6.0 | 7.2 | 5.8 |
| Reversion (15 min.) | 0.0 | 0.0 | 0.0 | 0.0 | 0.2 | 0.5 | 5.0 |
| Stress-Strain at 153°C | | | | | | | |
| Cure Time, minutes | 60 | 60 | 60 | 60 | 50 | 40 | 20 |
| 300% Modulus, psi | 250 | 740 | 1380 | 1600 | 900 | 1440 | 1670 |
| Ult. Tensile, psi | 690 | 1790 | 2400 | 2020 | 1840 | 2060 | 1850 |
| Ult. Elongation, % | 500 | 500 | 420 | 400 | 450 | 400 | 330 | when 1,2-bis(O,O'-diethylphophorotrithioyl)ethane is used as the cross-linking agent.

In Stocks 1–4, Table VII, the amount of cross-linking agent is varied from 1.0–4.0 parts. The data indicate the concentration of cross-linking agent has very little effect upon processing safety while the cross-link density and the cure rate increase proportionally with the amount of cross-linking agent used. Stocks 5, 6 and 7

Table VIII illustrates the effect of sulfenamide accelerator with combinations of sulfur and cross-linking agent. Generally, the presence of accelerator reduces processing safety and enhances cure rate and the state of cure.

Table IX shows the cross-linking of rubber with bis(1-pyrrolidinylthiocarbonyldithio)alkanes. Stocks 3 and 4 illustrate a cross-linking agent wherein the bridging group is derived from 2,9-menthane dithiol which is a hybrid linking group wherein one end is attached to cycloalkyl and the other end is attached to alkyl. It is noted that this particular bridging group enhances processing safety.

Table X demonstrates the cross-linking of rubber with bis-trisulfides. The data indicate that the trisulfides are fast curing, strong vulcanizing agents but the uncured stocks are deficient in processing safety.

TABLE VIII

| Stock | 1 | 2 | 3 | 4 | 5 | 6 |
|---|---|---|---|---|---|---|
| Masterbatch A | 157.0 | | | | | |
| 1,2-bis(N,N-dimethyl-thiocarbamoyl-dithio)ethane | 1.0 | 1.73 | 1.5 | 1.5 | 1.5 | 1.5 |
| Sulfur | 0.5 | 0.5 | 0.25 | 0.25 | 0.75 | 0.75 |
| Santocure NS | 0.5 | 0.5 | 0.25 | 0.75 | 0.25 | 0.75 |
| Mooney Scorch at 121°C | | | | | | |
| $t_5$, min. | 33.7 | 31.8 | 39.8 | 33.9 | 29.7 | 26.6 |
| Rheometer Data at 144°C | | | | | | |
| $t_{90}-t_2$, min. | 10.6 | 9.5 | 18.5 | 11.8 | 10.3 | 11.9 |
| R Max. | 65.6 | 72.1 | 54.0 | 62.0 | 74.0 | 84.8 |
| R Min. | 4.9 | 5.1 | 6.0 | 6.0 | 5.8 | 5.9 |
| Rheometer Data at 154°C | | | | | | |
| $t_{90}-t_2$, min. | 6.4 | 9.6 | 12.1 | 9.3 | 4.8 | 7.9 |
| R Max. | 56.8 | 74.0 | 50.8 | 58.4 | 68.7 | 82.9 |
| R Min. | 4.6 | 5.0 | 4.5 | 5.1 | 5.1 | 5.3 |
| Rheometer Data at 164°C | | | | | | |
| $t_{90}-t_2$, min. | 3.0 | 4.8 | 6.1 | 5.5 | 2.9 | 3.0 |
| R Max. | 51.4 | 69.5 | 47.3 | 55.7 | 65.7 | 75.8 |
| R Min. | 4.9 | 4.9 | 4.9 | 5.1 | 5.1 | 5.1 |
| Reversion (15 min.) | 0.0 | 0.0 | 0.0 | 0.0 | 0.7 | 0.0 |
| Stress-Strain Data at 144°C | | | | | | |
| Cure Time, minutes | 55 | 55 | 60 | 60 | 60 | 60 |
| 300% Modulus, psi | 1650 | 1850 | 1440 | 1550 | 1880 | — |
| Ult. Tensile, psi | 2350 | 1890 | 2200 | 2240 | 1880 | 1700 |
| Ult. Elongation, % | 380 | 300 | 430 | 380 | 300 | 270 |

TABLE IX

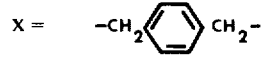

| | Cross-linking Agent | | | | | |
|---|---|---|---|---|---|---|
| Stock | 1 | 2 | 3 | 4 | 5 | 6 |
| Masterbatch A | 157.0 ———————————→ | | | | | |
| X = 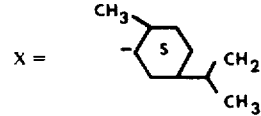 | 3.0 | 1.0 | — | — | — | — |
| X = 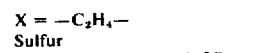 | — | — | 3.0 | 1.0 | — | — |
| X = $-C_2H_4-$ | — | — | — | — | 3.0 | 1.0 |
| Sulfur | — | 1.0 | — | 1.0 | — | 1.0 |
| Mooney Scorch at 121°C | | | | | | |
| $t_5$, min. | 36.6 | 20.2 | 56.4 | 20.0 | 39.7 | 27.6 |
| Rheometer Data at 144°C | | | | | | |
| $t_{90}-t_2$, min. | 19.9 | 4.7 | 69.0 | 9.8 | 25.2 | 11.0 |
| R Max. | 24.5 | 53.5 | 22.5 | 50.0 | 45.0 | 63.0 |
| R Min. | 3.0 | 2.9 | 2.6 | 2.9 | 3.0 | 3.0 |
| Rheometer Data at 164°C | | | | | | |
| $t_{90}-t_2$, min. | 4.0 | 1.5 | 19.8 | 2.1 | — | — |
| R Max. | 22.7 | 46.0 | 18.7 | 40.9 | — | — |
| R Min. | 2.6 | 3.4 | 2.2 | 3.7 | — | — |
| Reversion (10 min.) | 0.3 | 2.0 | 0.0 | 1.9 | — | — |
| Stress-Strain Data at 144°C | | | | | | |
| Cure Time, min. | 120 | 40 | 120 | 40 | 90 | 90 |
| 300% Modulus, psi | 610 | 1600 | 455 | 1450 | 1100 | 1690 |
| Ult. Tensile, psi | 2370 | 3850 | 1600 | 3960 | 2640 | 3500 |
| Ult. Elongation, % | 610 | 550 | 560 | 600 | 510 | 490 |

TABLE X $$R\!\!>\!\!NCSSSC_2H_4SSSCH\!\!<\!\!R \quad \text{(with S=S above each C)}$$

| Stock | Cross-linking Agents | | | |
|---|---|---|---|---|
| | 1 | 2 | 3 | 4 |
| Masterbatch A* | 158.0 | 158.0 | 158.0 | 158.0 |
| R = —$C_2H_5$ | 5.0 | 5.0 | — | — |
| R = —$CH_3$ | — | — | 5.0 | 5.0 |
| Sulfur | — | 0.5 | — | 0.5 |
| Mooney Scorch at 121°C | | | | |
| $t_5$, min. | 4.9 | 4.4 | 3.2 | 3.3 |
| Rheometer Data at 144°C | | | | |
| $t_{90}-t_2$, min. | 18.0 | 12.6 | 17.2 | 14.2 |
| R Max. | 56.2 | 59.7 | 69.3 | 73.8 |
| R Min. | 11.8 | 12.0 | 13.5 | 13.5 |
| Rheometer Data at 171°C | | | | |
| $t_{90}-t_2$, min. | — | — | 4.4 | 3.4 |
| R Max. | — | — | 60.0 | 63.6 |
| R Min. | — | — | 13.0 | 13.0 |
| Stress-Strain Data at 171°C | | | | |
| Cure Time, minutes | 20 | 20 | 20 | 20 |
| Ult. Tensile, psi | 2600 | 2650 | 2050 | 2000 |
| Ult. Elongation, % | 290 | 260 | 200 | 190 |

*Contained one additional part of stearic acid.

The cross-linking properties of bis(2-benzothiazolyldithio)alkanes are illustrated in Tables XI, XII, XIII and XIV. The invention is illustrated with a natural rubber stock, however, similar results are obtained using styrene-butadiene copolymer stocks or stocks comprising an elastomer blend of natural rubber and styrene-butadiene rubber. The effect of concentration and the presence of sulfur and accelerator is substantially the same as with the dithiocarbamate cross-linking agents. However, the benzothiazole cross-linking agents usually require larger amounts to achieve the same degree of cure. The data indicate that higher cure temperatures may be used with the benzothiazole cross-linking agents but with sulfur the reversion resistance is diminished. A stock comprising 5.0 parts of 1,6-bis(2-benzothiazolyldithio)hexane and 157.0 parts of masterbatch A cured at 171°C gives a 21.6 in.-lb. rise in rheometer torque and a value for $t_{90}-t_2$ of 26.3 minutes. Table XII also illustrates a cross-link agent having a 2-mercaptobenzoxazole accelerating moiety.

TABLE XI

| Stock | Bis(Benzothiazolyldithio)alkanes Cross-linking Agents | | | | | |
|---|---|---|---|---|---|---|
| | 1 | 2 | 3 | 4 | 5 | 6 |
| Masterbatch A | 157.0 → | | | | | |
| 1,2-bis(2-benzothiazolyldithio)ethane | 4.0 | 6.0 | 10.0 | — | — | — |
| α,α'-bis(2-benzothiazolyldithio)-p-xylene | — | — | — | 4.0 | 6.0 | 10.0 |
| Mooney Scorch at 135°C | | | | | | |
| $t_5$, min. | — | 112.3 | 89.7 | 27.5 | 43.9 | 38.4 |
| Rheometer Data at 164°C | | | | | | |
| $t_{90}-t_2$, min. | 23.0 | 36.6 | 51.0 | 17.5 | 21.3 | 22.8 |
| R Max. | 13.4 | 25.0 | 45.0 | 24.3 | 32.4 | 44.0 |
| R Min. | 3.1 | 3.6 | 3.1 | 10.1 | 10.2 | 9.8 |
| Rheometer Data at 174°C | | | | | | |
| $t_{90}-t_2$, min. | — | 17.6 | 24.8 | 6.7 | 8.1 | 12.5 |
| R Max. | 7.0 | 26.7 | 44.7 | 22.0 | 32.0 | 45.4 |
| R Min. | 3.4 | 3.4 | 3.2 | 10.2 | 11.8 | 8.9 |
| Reversion (10 min.) | 0.0 | 0.3 | 0.3 | 0.0 | 0.0 | 0.0 |
| Rheometer Data at 184°C | | | | | | |
| $t_{90}-t_2$, min. | — | 9.2 | 11.9 | — | — | — |
| R Max. | — | 26.1 | 45.7 | — | — | — |
| R Min. | — | 2.6 | 3.2 | — | — | — |
| Reversion (10 min.) | — | 0.1 | 0.8 | — | — | — |
| Stress-Strain Data at 164°C | | | | | | |
| Cure Time, min. | 90 | 90 | 90 | 30 | 30 | 45 |
| 300% Modulus, psi | 150 | 450 | 750 | 240 | 450 | 800 |
| Ult. Tensile, psi | 270 | 1100 | 2340 | 1380 | 1700 | 2710 |
| Ult. Elongation, % | 380 | 480 | 580 | — | 580 | 580 |

TABLE XII

| Stock | 1 | 2 | 3 | 4 |
|---|---|---|---|---|
| Masterbatch A | 157.0 → | | | |
| Sulfur | — | 1.0 | — | 1.0 |
| 1,2-bis(2-benzoxazolyldithio)ethane | 3.0 | 1.0 | — | — |
| α,α'-bis(2-benzothiazolyldithio)-m-xylene | — | — | 3.0 | 1.0 |
| Mooney Scorch at 121°C | | | | |
| $t_5$, min. | 126 | 76 | — | 67 |

TABLE XII-continued

| Stock | 1 | 2 | 3 | 4 |
|---|---|---|---|---|
| Rheometer Data at 144°C | | | | |
| t₉₀-t₂, min. | 62.0 | 55.8 | 52.0 | 25.9 |
| R Max. | 7.3 | 15.9 | 12.1 | 36.1 |
| R Min. | 2.0 | 2.8 | 2.1 | 2.7 |
| Rheometer Data at 164°C | | | | |
| t₉₀-t₂, min. | 23.6 | 11.0 | 9.8 | 5.4 |
| R Max. | 8.7 | 13.2 | 10.5 | 31.0 |
| R Min. | 3.0 | 1.3 | 2.5 | 2.2 |
| Reversion | 0 | 0.3 | 0.2 | 1.2 |
| Stress-Strain at 144°C | | | | |
| Cure Time, min. | — | 120 | — | 60 |
| 300% Modulus, psi | — | 260 | — | 900 |
| Ult. Tensile Strength, psi | — | 1380 | — | 3250 |
| Ult. Elongation, % | — | 610 | — | 600 |

TABLE XIII

| Stock | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Masterbatch A | 157.0 | → | | | | | | | | | | | | |
| 1,2-bis(2-benzothiazolyl-dithio)ethane | 1.0 | 1.0 | 2.0 | 2.0 | 2.0 | 3.0 | 3.0 | — | — | — | — | — | — | — |
| α,α'-bis(2-benzothiazolyl-dithio)-p-xylene | — | — | — | — | — | — | — | 1.0 | 1.0 | 2.0 | 2.0 | 2.0 | 3.0 | 3.0 |
| Sulfur | 0.5 | 1.5 | 0.3 | 1.0 | 1.7 | 0.5 | 1.5 | 0.5 | 1.5 | 0.3 | 1.0 | 1.7 | 0.5 | 1.5 |
| Mooney Scorch at 121°C | | | | | | | | | | | | | | |
| t₅, min. | 67.9 | 34.4 | 74.2 | 33.6 | 30.0 | 44.1 | 26.4 | 46.1 | 27.2 | 44.5 | 26.2 | 21.6 | 30.9 | 21.0 |
| Rheometer Data at 154°C | | | | | | | | | | | | | | |
| t₉₀-t₂, min. | 12.3 | 5.9 | 13.4 | 4.7 | 3.4 | 9.1 | 3.8 | 7.5 | 6.4 | 6.7 | 4.9 | 4.0 | 6.1 | 4.4 |
| R Max. | 24.5 | 41.2 | 32.7 | 49.7 | 56.4 | 48.0 | 65.0 | 36.0 | 57.1 | 38.7 | 60.9 | 72.9 | 54.7 | 78.0 |
| R Min. | 5.5 | 4.8 | 4.7 | 4.3 | 3.5 | 4.5 | 5.0 | 6.8 | 6.4 | 5.9 | 6.4 | 6.1 | 5.9 | 6.3 |
| Rheometer Data at 164°C | | | | | | | | | | | | | | |
| t₉₀-t₂, min. | 8.2 | 4.2 | 7.7 | 2.5 | 2.6 | 5.7 | 2.0 | — | — | — | — | — | — | — |
| R Max. | 21.9 | 39.3 | 30.6 | 48.8 | 56.7 | 47.2 | 62.3 | — | — | — | — | — | — | — |
| R Min. | 3.6 | 4.6 | 5.1 | 4.8 | 3.7 | 4.4 | 5.1 | — | — | — | — | — | — | — |
| Rheometer Data at 174°C | | | | | | | | | | | | | | |
| t₉₀-t₂, min. | 3.3 | 2.0 | 2.4 | 1.4 | 1.0 | 2.8 | 1.2 | 2.0 | 2.3 | 1.9 | 1.7 | 1.7 | 2.0 | 1.7 |
| R Max. | 18.2 | 35.8 | 24.8 | 44.1 | 50.1 | 42.0 | 61.9 | 31.6 | 34.9 | 36.7 | 57.9 | 72.8 | 51.3 | 76.3 |
| R Min. | 4.2 | 4.6 | 4.3 | 4.0 | 3.7 | 4.6 | 4.7 | 5.8 | 5.8 | 7.1 | 5.8 | 6.5 | 5.5 | 5.7 |
| Reversion (10 min.) | 0.6 | 4.8 | 1.1 | 2.9 | 8.0 | 1.6 | 4.6 | 4.6 | 11.5 | 4.5 | 9.7 | 12.9 | 5.3 | 11.0 |
| Stress-Strain at 154°C | | | | | | | | | | | | | | |
| Cure Time, min. | 35 | 15 | 40 | 20 | 10 | 35 | 15 | 20 | 15 | 20 | 15 | 15 | 15 | 15 |
| 300% Modulus, psi | 500 | 1030 | 650 | 1230 | 1350 | 1130 | 1510 | 660 | 1200 | 800 | 1350 | 1490 | 1150 | 1600 |
| Ult. Tensile, psi | 1500 | 2510 | 1950 | 2840 | 3100 | 3010 | 3360 | 2080 | 3260 | 2400 | 3680 | 3800 | 3580 | 4050 |
| Ult. Elongation, % | 550 | 520 | 530 | 530 | 530 | 550 | 520 | 550 | 550 | 540 | 600 | 570 | 610 | 580 |

TABLE XIV

| Stock | 1 | 2 | 3 | 4 | 5 | 6 | 7 | 8 | 9 | 10 | 11 | 12 |
|---|---|---|---|---|---|---|---|---|---|---|---|---|
| Masterbatch A | 157.0 | → | | | | | | | | | | |
| 1,2-(2-benzothiazolyl-dithio)ethane | 1.0 | 1.0 | 1.0 | 1.0 | 2.0 | 3.0 | — | — | — | — | — | — |
| α,α'-(2-benzothiazolyl-dithio)-p-xylene | — | — | — | — | — | — | 1.0 | 1.0 | 1.0 | 1.0 | 2.0 | 3.0 |
| Sulfur | 0.25 | 0.25 | 0.75 | 0.75 | 0.5 | 0.5 | 0.25 | 0.25 | 0.75 | 0.75 | 0.5 | 0.5 |
| Santocure NS | 0.25 | 0.75 | 0.25 | 0.75 | 0.5 | 0.5 | 0.25 | 0.75 | 0.25 | 0.75 | 0.5 | 0.5 |
| Mooney Scorch at 121°C | | | | | | | | | | | | |
| t₅, min. | 76.2 | 53.7 | 41.0 | 33.3 | 40.7 | 38.3 | 43.7 | 32.7 | 27.5 | 23.7 | 25.4 | 23.7 |
| Rheometer Data at 154°C | | | | | | | | | | | | |
| t₉₀-t₂, min. | 12.3 | 9.1 | 5.4 | 3.7 | 6.5 | 8.1 | 6.8 | 5.5 | 4.8 | 3.5 | 4.8 | 5.2 |
| R Max. | 19.8 | 27.9 | 35.0 | 47.7 | 46.0 | 53.2 | 32.3 | 42.0 | 53.0 | 62.2 | 58.8 | 65.6 |
| R Min. | 3.8 | 3.8 | 3.9 | 3.8 | 3.4 | 4.0 | 6.0 | 6.3 | 6.4 | 6.4 | 6.5 | 5.5 |
| Rheometer Data at 164°C | | | | | | | | | | | | |
| t₉₀-t₂, min. | 9.4 | 6.6 | 4.0 | 2.7 | 4.9 | 5.9 | — | — | — | — | — | — |
| R Max. | 18.9 | 26.4 | 33.5 | 46.3 | 44.4 | 51.0 | — | — | — | — | — | — |
| R Min. | 3.8 | 3.7 | 3.9 | 3.8 | 3.8 | 3.8 | — | — | — | — | — | — |
| Rheometer Data at 174°C | | | | | | | | | | | | |
| t₉₀-t₂, min. | 5.5 | 3.1 | 2.0 | 1.1 | 2.4 | 3.2 | 2.1 | 1.9 | 1.5 | 1.4 | 1.7 | 1.8 |
| R Max. | 17.0 | 24.7 | 31.1 | 43.9 | 42.3 | 49.0 | 28.8 | 39.1 | 50.1 | 60.2 | 53.2 | 61.0 |
| R Min. | 4.2 | 4.8 | 4.8 | 5.1 | 4.8 | 3.8 | 6.8 | 6.5 | 7.8 | 6.8 | 6.8 | 5.5 |
| Reversion (10 min.) | 0.1 | 0.0 | 1.7 | 3.0 | 2.1 | 0.6 | 3.5 | 4.1 | 7.4 | 9.3 | 6.3 | 5.2 |
| Stress-Strain at 154°C | | | | | | | | | | | | |
| Cure Time, min. | 35 | 30 | 20 | 20 | 25 | 35 | 25 | 15 | 15 | 15 | 15 | 15 |
| 300% Modulus, psi | 320 | 520 | 750 | 1110 | 1060 | 1300 | 550 | 700 | 950 | 1200 | 1190 | 1250 |
| Ult. Tensile, psi | 1180 | 1600 | 1990 | 2960 | 3040 | 3300 | 2150 | 2600 | 3150 | 3900 | 2760 | 3790 |
| Ult. Elongation, % | 530 | 520 | 530 | 550 | 580 | 540 | 600 | 600 | 620 | 610 | 620 | 580 |

The improved stability of the cross-links formed by using the cross-linking agents of this invention is demonstrated in a series of tests wherein the fatigue properties of vulcanizates are compared between sulfenamide accelerator/sulfur and cross-linking agent/sulfur vulcanizatin systems. The comparisons are conducted at various sulfur/accelerator ratios and the fatigue properties compared at equal modulus. The comparisons show that vulcanizates produced with the cross-linking agent have approximately twice the creep resistance, about 30% greater fatigue resistance and about twice the thermal stability as evidenced by reversion data.

Part of the data used in the above-mentioned comparisons is reproduced in Table XV. Stock 1 is the control having 0.5 parts N-tert-butyl-2-benzothiazolesulfenamide accelerator. The fatigue test comprises repeatedly flexing a rubber specimen to 100% elongation and measuring the number of times the sample is flexed until failure occurs. (Monsanto Bulletin O/RC 21). The creep test comprises subjecting a rubber specimen to a constant load of 45 psi at 100°C and measuring the time required for the sample to elongate 50%.

TABLE XV

| Stock | 1 | 2 | 3 | 4 | 5 | 6 | 7 |
|---|---|---|---|---|---|---|---|
| Masterbatch A | 157.0 → | | | | | | |
| α,α'-(2-benzothiazolyl-dithio)-p-xylene | — | 0.72 | 1.52 | 2.95 | 5.27 | — | — |
| 2,9-di(1-pyrrolidinylthio-carbonyldithio)menthane | — | — | — | — | — | 1.16 | 1.64 |
| Sulfur | 2.0 | 4.80 | 3.31 | 2.24 | 1.32 | 1.16 | 0.66 |
| Mooney Scorch at 121°C | | | | | | | |
| $t_5$, min. | 34.9 | 28.2 | 27.2 | 27.2 | 30.0 | 23.6 | 25.3 |
| Rheometer Data at 144°C | | | | | | | |
| $t_{90}-t_2$, min. | 14.9 | 21.6 | 15.6 | 12.1 | 12.3 | 9.9 | 19.7 |
| R Max. | 50.0 | 66.0 | 70.1 | 71.5 | 70.7 | 50.8 | 49.2 |
| Rheometer Data at 164°C | | | | | | | |
| $t_{90}-t_2$, min. | 3.4 | 5.3 | 4.1 | 3.2 | 3.8 | 1.7 | 2.6 |
| R Max. | 58.2 | 61.2 | 66.2 | 71.7 | 70.3 | 48.0 | 44.9 |
| Reversion (10 min.) in-lbs. | 9.0 | 4.8 | 7.6 | 6.0 | 3.1 | 1.2 | 0.5 |
| Stress-Strain Data at 144°C | | | | | | | |
| Cure Time, min. | 40 | 60 | 40 | 40 | 50 | 50 | 60 |
| 300% Modulus, psi | 1300 | 1420 | 1520 | 1600 | 1600 | 1500 | 1440 |
| Ult. Tensile, psi | 3840 | 3510 | 3840 | 3900 | 3800 | 3900 | 3950 |
| Ult. Elongation, % | 600 | 550 | 560 | 550 | 540 | 560 | 580 |
| Fatigue, 100% Extension | | | | | | | |
| kc. to Failure (unaged) | 131 | 165 | 213 | 130 | 104 | 94 | 65 |
| kc. to Failure (aged 4 days at 90°C) | 85 | — | — | — | — | 108 | 99 |
| kc. to Failure (aged 7 days at 90°C) | 15 | — | — | — | — | 90 | 107 |
| Creep | | | | | | | |
| Hours to 50% Extension | — | 32 | 64 | 220 | 336 | — | — |
| Tear Strength, lb/in. | | | | | | | |
| 25°C | — | 447 | 485 | 463 | 633 | — | — |
| 100°C | — | 300 | 353 | 323 | 322 | — | — |

Table XVI illustrates the properties of cross-linking agents having thiazolinyl and thiadiazolinyl accelerating moieties. Table XVII illustrates cross-linking agents having thiazolyl and pyrimidinyl accelerating moieties.

TABLE XVI

| Stock | Acc—SSCH$_2$—CH$_2$SS—Acc Cross-linking Agent | | | |
|---|---|---|---|---|
| | 1 | 2 | 3 | 4 |
| Masterbatch A | 157.0 | 157.0 | 157.0 | 157.0 |
| Acc = 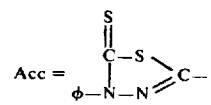 | 3.0 | 1.0 | — | — |
| Acc = 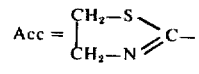 | — | — | 3.0 | 1.0 |
| Sulfur | — | 1.0 | — | 1.0 |
| Mooney Scorch at 121°C | | | | |
| $t_5$, min. | 93.7 | 20.7 | 75.1 | 38.3 |
| Rheometer Data at 144°C | | | | |
| $t_{90}-t_2$, min. | 40.0 | 36.0 | 58.0 | 23.1 |
| R Max. | 11.0 | 28.0 | 17.0 | 43.0 |
| R Min. | 3.0 | 3.0 | 3.0 | 3.0 |
| Stress-Strain Data at 144°C | | | | |
| Cure Time, minutes | 120 | 80 | 120 | 60 |
| 300% Modulus, psi | — | 490 | 200 | 960 |
| Ult. Tensile, psi | 340 | 1500 | 810 | 3210 |
| Ult. Elongation, % | 550 | 540 | 510 | 620 |

TABLE XVII

| Stock | Acc—SSC$_2$H$_4$SS—Acc | | | | | |
|---|---|---|---|---|---|---|
| | 1 | 2 | 3 | 4 | 5 | 6 |
| Masterbatch A | 157.0 → | | | | | |
| Sulfur | — | 1.0 | — | 1.0 | — | 1.0 |

TABLE XVII-continued

| Stock | Acc—SSC$_2$H$_4$SS—Acc | | 3 | 4 | 5 | 6 |
|---|---|---|---|---|---|---|
| | 1 | 2 | | | | |
| Acc = $\underset{CH_3COCH_2CH_2-C-S}{\overset{O\ \ \ \ \ CH_3-C-N}{\|\ \ \ \ \ \ \ \ \ \|}}\!\!\!\!\!\!\!\!\!\!\!\!\!\!\!>C-$ | 3.0 | 1.0 | — | — | — | — |
| Acc = $\underset{HC-S}{\overset{CH_3-C-N}{\|}}\!\!\!\!\!\!\!\!\!\!\!>C-$ | — | — | 3.0 | 1.0 | — | — |
| Acc = $HC\underset{CH_3}{\overset{CH_3}{<}}\!\!\!\!\!\!\!\!\!>\!\!\!\underset{C=N}{\overset{C-N}{<}}\!\!\!\!\!\!\!\!\!>C-$ | — | — | — | — | 3.0 | 1.0 |
| Mooney Scorch at 121°C | | | | | | |
| t$_5$, min. | — | 79 | — | 63 | — | 65 |
| Rheometer Data at 144°C | | | | | | |
| t$_{90}$-t$_2$, min. | 48.8 | 36.3 | 87.9 | 31.3 | — | 31.2 |
| R Max. | 7.0 | 39.9 | 15.2 | 42.2 | — | 36.8 |
| R Min. | 1.3 | 2.7 | 4.5 | 2.9 | — | 2.8 |
| Rheometer Data at 164°C | | | | | | |
| t$_{90}$-t$_2$, min. | 14.0 | 14.3 | 22.4 | 6.3 | 33.0 | 5.5 |
| R Max. | 8.3 | 32.3 | 16.0 | 34.9 | 8.4 | 32.2 |
| R Min. | 2.2 | 2.5 | 2.3 | 2.2 | 1.0 | 2.4 |
| Reversion | 0.2 | 0.4 | 0.1 | 0.6 | 0.0 | 0.3 |
| Stress-Strain at 144°C | | | | | | |
| Cure Time, min. | — | 120 | — | 90 | — | 90 |
| 300% Modulus, psi | — | 1150 | — | 1160 | — | 1080 |
| Ult. Tensile Strength, psi | — | 3120 | — | 3450 | — | 3000 |
| Ult. Elongation, % | — | 570 | — | 590 | — | 580 |

The properties of rubber stocks containing bis(phosphorotrithioates) are shown in Table XVIII. The processing safety is substantially greater than stocks containing cross-linking agents having dithiocarbamates or azole accelerating moieties; and the cross-linking ability generally appears between that found for dithiocarbamate and azole accelerating moieties.

Another low-temperature cross-linking agent is 1,2-bis(N-benzylthiocarbamoyldithio)ethane, for example, a seven in. lb. rise in rheometer torque is observed temperature. Satisfactory cure is obtained by heating the stock overnight at 100°C. Notice the cure rate, t$_{90}$-t$_2$, is in hours rather than minutes. Slight cure is achieved by heating the stock at 144°C. The reduced activity at the higher temperature is apparently due to the inability of the xanthate to survive the higher temperature.

TABLE XVIII $$Y\!\!>\!\!\underset{Y}{\overset{S}{P}}\!SS\!-\!X\!-\!SS\!\underset{Y}{\overset{S}{P}}\!<\!Y$$

| Stock | Cross-linking Agents | | | | | | | | | |
|---|---|---|---|---|---|---|---|---|---|---|
| | 1 | 2 | 3 | 4 | 5 | 6 | 7 | 8 | 9 | 10 |
| X | —C$_2$H$_4$— | | —C$_2$H$_4$— | | -CH$_2$-C$_6$H$_4$-CH$_2$- | | -CH$_2$-C$_6$H$_4$-CH$_2$- | | -(CH$_3$-cyclohexyl-CH$_2$-CH$_3$)- | |
| Y | C$_2$H$_5$O— | | nC$_4$H$_9$O— | | iC$_3$H$_7$O— | | nC$_4$H$_9$O— | | iC$_3$H$_7$O— | |
| Cross-linking Agent | 3.0 | 1.0 | 3.0 | 1.0 | 3.0 | 1.0 | 3.0 | 1.0 | 3.0 | 1.0 |
| Sulfur | — | 1.0 | — | 1.0 | — | 1.0 | — | 1.0 | — | 1.0 |
| Masterbatch A | 157.0 → | | | | | | | | | |
| Mooney Scorch at 121°C | | | | | | | | | | |
| t$_5$, min. | 121.5 | 88.0 | 110.0 | 69.2 | 158.5 | 92.8 | 50.2 | 44.5 | — | 110.9 |
| Rheometer Data at 144°C | | | | | | | | | | |
| t$_{90}$-t$_2$, min. | 41.7 | 26.3 | 54.0 | 42.3 | 43.5 | 20.4 | 39.0 | 21.6 | — | 33.6 |
| R Max. | 31.5 | 32.9 | 28.0 | 27.0 | 22.2 | 29.2 | 21.5 | 26.2 | — | 22.5 |
| R Min. | 3.0 | 2.3 | 3.0 | 2.0 | 3.0 | 2.4 | 2.5 | 2.7 | — | 2.2 |
| Rheometer Data at 164°C | | | | | | | | | | |
| t$_{90}$-t$_2$, min. | 8.8 | 5.7 | — | — | 6.8 | 4.4 | 7.0 | 5.4 | 37.0 | 5.6 |
| R Max. | 32.3 | 28.0 | — | — | 20.8 | 26.1 | 17.7 | 21.9 | 8.7 | 20.2 |
| R Min. | 3.3 | 3.1 | — | — | 4.2 | 2.7 | 1.5 | 1.6 | 2.5 | 2.9 |
| Reversion (10 min.) | 0.2 | 1.2 | — | — | 0.1 | 2.0 | 0.2 | 2.0 | 0.0 | 1.3 |
| Stress-Strain Data at 144°C | | | | | | | | | | |
| Cure Time, min. | 120 | 90 | 120 | 90 | 120 | 60 | 120 | 55 | 120 | 90 |
| 300% Modulus, psi | 690 | 750 | 460 | 500 | 440 | 540 | 350 | 600 | 90 | 490 |
| Ult. Tensile, psi | 2540 | 2450 | 2200 | 1700 | 1400 | 2680 | 1050 | 1710 | 380 | 1690 |
| Ult. Elongation, % | 620 | 590 | 630 | 580 | 570 | 600 | 500 | 540 | 610 | 580 |

The cross-linking agents having xanthogen accelerating moieties are illustrated in Table XIX. It is important that stocks containing bis xanthates be cured at low when a rubber specimen comprising masterbatch A (157 parts) and cross-linking agent (4 parts) are heated at 35°C for 22 hours.

TABLE XIX $$(CH_3)_2CHO\overset{S}{\overset{\|}{C}}SSCH_2CH_2SS\overset{S}{\overset{\|}{C}}OCH(CH_3)_2$$

| Stock | Cross-linking Agent | |
|---|---|---|
| | 1 | 2 |
| Masterbatch A | 157.0 | 157.0 |
| 1,2-bis(isopropyloxythio-carbonyldithio)ethane | 5.0 | 2.0 |
| Sulfur | — | 1.0 |
| Rheometer Data at 100°C | | |
| $t_{90}$-$t_2$, Hrs. | 17.2 | 5.5 |
| R Max. | 40.5 | 21.8 |
| R Min. | 19.3 | 10.0 |

The cross-linking properties of a number of different cross-linking agents of the inventions are compared in Table XX. Numbers preceded by > signs mean that the maximum value has not been reached and the number listed is the value obtained after two hours. Five parts of cross-linking agent is tested in each stock. The stock number and the corresponding cross-linking agent are listed below:

Stock

1 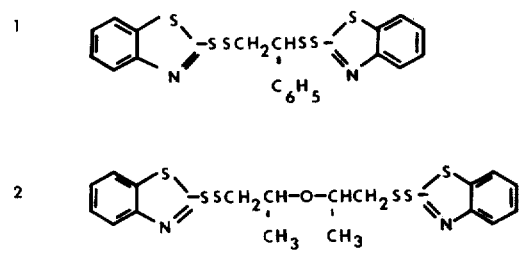

2 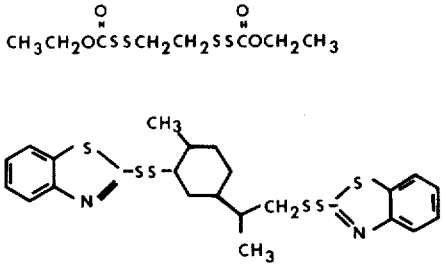

3 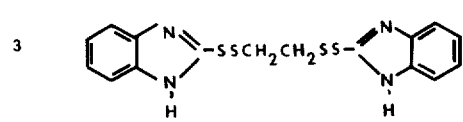

4 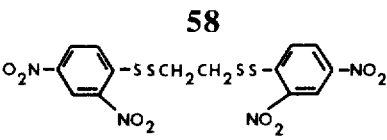

5 $$CH_3CH_2O\overset{O}{\overset{\|}{C}}SSCH_2CH_2SS\overset{O}{\overset{\|}{C}}OCH_2CH_3$$

6 (structure)

7 (structure)

8 (structure)

9 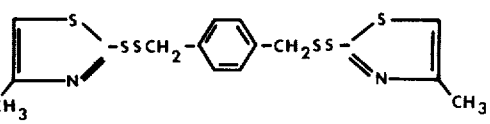

10 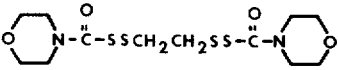

TABLE XX

| Stock | 1 | 2 | 3 | 4 | 5 | 6 | 7 | 8 | 9 | 10 |
|---|---|---|---|---|---|---|---|---|---|---|
| Masterbatch A | 157.0 → | | | | | | | | | |
| Mooney Scorch at 121°C | | | | | | | | | | |
| $t_5$, min. | 19.4 | 96.1 | 107.0 | >120.0 | >120.0 | 79.9 | >120.0 | 90.9 | 35.1 | 4.9 |
| Rheometer Data at 144°C | | | | | | | | | | |
| $t_{90}$-$t_2$, min. | 36.6 | 93.0 | 71.7 | 53.0 | 57.0 | 78.6 | 86.3 | 66.5 | 19.4 | 20.8 |
| R Max. | 51.8 | 27.5 | 17.0 | 11.4 | 23.4 | 26.4 | 33.0 | 39.3 | 31.3 | 29.5 |
| R Min. | 5.0 | 5.8 | 10.1 | 7.2 | 5.0 | 6.3 | 5.6 | 6.3 | 6.3 | 9.4 |
| Rheometer Data at 164°C | | | | | | | | | | |
| $t_{90}$-$t_2$, min. | 8.0 | 32.3 | 25.1 | 83.0 | 22.5 | 42.2 | 24.3 | 17.2 | 6.1 | 6.9 |
| R Max. | 49.5 | 36.0 | 19.8 | 20.7 | 20.1 | 27.0 | 35.6 | 37.2 | 27.0 | 22.5 |
| R Min. | 5.5 | 5.8 | 10.1 | 6.7 | 5.2 | 6.4 | 4.9 | 6.2 | 6.2 | 9.4 |
| Reversion | 0.3 | 0.2 | 0.2 | 0.0 | 0.0 | 0.0 | 0.0 | 0.0 | 0.2 | 1.3 |
| Stress-Strain Data at 144°C | | | | | | | | | | |
| Cure Time, min. | 90 | 120 | 120 | 120 | 120 | 120 | 120 | 120 | 70 | 45 |
| 300% Modulus, psi | 1280 | 600 | 400 | 200 | 240 | 420 | 610 | 740 | 1000 | 560 |
| Ult. Tensile, psi | 3490 | 2090 | 1190 | 690 | 950 | 1410 | 2330 | 2700 | 3310 | 2100 |
| Ult. Elongation, % | 570 | 550 | 500 | 530 | 580 | 500 | 600 | 600 | 620 | 580 |

The cross-linking properties of other cross-linking agents are illustrated in Table XXI. Three parts of cross-linking agent is used in each stock. The stocks contain no sulfur except for Stock 1, the control, which has 2 parts sulfur and 0.5 part N-tert-butyl-2-benzothiazolesulfenamide.

| Stock No. | Cross-linking Agent |
|---|---|
| 1 | Control |
| 2 | 1,2-bis(2-pyridinyldithio)ethane |
| 3 | tetra(O,O'-diethylphosphorotrithioyl)-pentaerythritolpropionate |
| 4 | 3,5-di(2-benzothiazolyldithio)toluene |
| 5 | tetra(2-benzothiazolyldithio)pentaerythritolpropionate |
| 6 | product of Experiment A |
| 7 | product of Experiment B |
| 8 | product of Experiment C |
| 9 | 1,2,-di(2-benzothiazolyldithio)-n-octane |
| 10 | 1,2-di(O,O'-diethylphosphorotrithioyl)-n-octane |
| 11 | 1,2-bis[2(4,6-di[diallylamino])-s-triazinyldithio]ethane |
| 12 | 1,2-bis[2(4,6-di[dipropylamino])-s-triazinyldithio]ethane |

Table XXII illustrates curing vulcanizable compositions using a mixture of two cross-linking agents. The data demonstrate the use of a combination of cross-linking agents to control the scorch time and cure rate of the vulcanizable compositions by varying the amount of each cross-linking agent. The data further illustrate that the combination gives a higher state of cure than either agent alone.

Table XXIII illustrates the use of the cross-linking agents in silica-reinforced stocks and further demonstrates the synergistic effect on vulcanizate properties when using a combination of two cross-linking agents.

TABLE XXI

| Stock | 1 | 2 | 3 | 4 | 5 | 6 | 7 | 8 | 9 | 10 | 11 | 12 |
|---|---|---|---|---|---|---|---|---|---|---|---|---|
| Masterbatch A | 157.0 | — | — | — | — | — | — | — | — | — | — | — |
| Mooney Scorch at 121°C | | | | | | | | | | | | |
| $t_5$, min. | 33.3 | 105.0 | 49.3 | 51.5 | 45.9 | 35.1 | 82.8 | 60.5 | 98.9 | >120.0 | — | 124.0 |
| Rheometer Data at 144°C | | | | | | | | | | | | |
| $t_{90}-t_2$, min. | 13.9 | 63.8 | 20.8 | 46.9 | 45.2 | 27.0 | 36.3 | 37.4 | 74.7 | 65.0 | 34.4 | 36.7 |
| R Max. | 67.0 | 46.0 | 31.5 | 32.8 | 30.9 | 53.0 | 54.7 | 45.0 | 29.0 | 43.3 | 11.7 | 33.5 |
| R Min. | 4.2 | 4.7 | 5.5 | 5.3 | 6.2 | 5.3 | 5.3 | 6.7 | 5.2 | 5.0 | 4.4 | 3.7 |
| Rheometer Data at 164°C | | | | | | | | | | | | |
| $t_{90}-t_2$, min. | 4.0 | 29.8 | 5.1 | 10.0 | 10.0 | 8.2 | 9.2 | 9.9 | 25.0 | 14.7 | 5.9 | 9.7 |
| R Max. | 69.1 | 43.0 | 29.2 | 28.7 | 25.9 | 50.0 | 52.2 | 40.3 | 27.5 | 40.3 | 11.4 | 35.7 |
| R Min. | 5.0 | 3.0 | 5.0 | 5.1 | 5.8 | 4.8 | 4.8 | 5.2 | 4.5 | 5.0 | 3.1 | 3.6 |
| Reversion (10 min.) | 12.8 | 0.0 | 0.1 | 0.7 | 0.4 | 0.2 | 0.0 | 0.0 | 0.0 | 0.0 | 0.2 | 0.5 |
| Stress-Strain Data at 144°C | | | | | | | | | | | | |
| Cure Time, min. | 30 | 120 | 60 | 90 | 90 | 80 | 90 | 90 | 120 | 120 | 75 | 85 |
| 300% Modulus, psi | 1550 | 910 | 750 | 850 | 650 | 1340 | 1300 | 1030 | 640 | 960 | 200 | 700 |
| Ult. Tensile, psi | 3860 | 3030 | 2470 | 2840 | 2110 | 3500 | 3680 | 3340 | 2630 | 3250 | 800 | 2560 |
| Ult. Elongation, % | 550 | 580 | 580 | 600 | 540 | 550 | 550 | 550 | 620 | 600 | 510 | 600 |

TABLE XXII

| Stock | 1 | 2 | 3 | 4 | 5 |
|---|---|---|---|---|---|
| Masterbatch A | 157.0 | | | | |
| Sulfur | 1.0 | | | | |
| α,α'-bis(2-benzothiazolyldithio)-p-xylene | 2.0 | — | 1.0 | 1.5 | 0.5 |
| 1,2-bis(O,O'-diisopropylphosphorotrithioyl)ethane | — | 2.0 | 1.0 | 0.5 | 1.5 |
| Mooney Scorch at 121°C | | | | | |
| $t_5$, min. | 27.1 | 77.3 | 44.2 | 37.5 | 59.1 |
| Rheometer Data at 144°C | | | | | |
| $t_{90}-t_2$, min. | 16.2 | 26.9 | 26.0 | 21.8 | 28.4 |
| R Max. | 56.0 | 64.4 | 75.1 | 68.2 | 75.5 |
| R Min. | 7.0 | 6.2 | 5.0 | 5.3 | 5.2 |
| Rheometer Data at 164°C | | | | | |
| $t_{90}-t_2$, min. | 3.9 | 6.3 | 5.0 | 4.1 | 5.7 |
| R Max. | 51.1 | 58.7 | 70.6 | 63.8 | 70.7 |
| R Min. | 4.9 | 3.1 | 4.5 | 4.7 | 4.3 |
| Reversion, in.-lb./10 min. | 2.8 | 0.3 | 0.3 | 0.5 | 0.1 |

TABLE XXIII

| Stock | 1 | 2 | 3 | 4 | 5 | 6 | 7 | 8 | 9 | 10 |
|---|---|---|---|---|---|---|---|---|---|---|
| Natural Rubber | 100.0 | — | — | — | — | — | — | — | — | — |
| Hi-Sil 210 | 50.0 | — | — | — | — | — | — | — | 25.0 | 25.0 |
| HAF Black | — | — | — | — | — | — | — | — | 25.0 | 25.0 |
| Zinc Oxide | 3.0 | — | — | — | — | — | — | — | — | — |
| Stearic Acid | 1.0 | — | — | — | — | — | — | — | — | — |
| Santoflex 13 | 2.0 | — | — | — | — | — | — | — | — | — |
| Sulfur | 3.0 | — | 2.0 | 2.0 | 2.0 | — | 2.0 | 2.0 | 2.5 | 2.0 |
| Santocure NS | 1.0 | — | — | — | — | — | — | — | 0.8 | — |
| Diphenylguanidine | 1.0 | — | — | — | — | — | — | — | 0.8 | — |
| α,α'-bis(2-benzothiazolyldithio)-p-xylene | — | 3.0 | 2.0 | — | 1.0 | — | — | — | — | 1.0 |
| α,α'-bis(O,O'-diisopropylphosphorotrithioyl)-p-xylene | — | 3.0 | — | 2.0 | 1.0 | — | — | 1.0 | — | 1.0 |
| 1,2-bis(hexahydro-1H-azepin-1-ylthio-carbamoyldithio)ethane | — | — | — | — | — | 5.0 | 2.0 | 1.0 | — | — |
| Mooney Scorch at 121°C | | | | | | | | | | |
| $t_5$, min. | 26.0 | 78.0 | 54.2 | 54.5 | 31.0 | 31.9 | 19.7 | 25.5 | 12.9 | 19.7 |
| Rheometer Data at 144°C | | | | | | | | | | |
| $t_{90}-t_2$, min. | 12.1 | 19.6 | 23.7 | 13.8 | 6.4 | 20.5 | 5.1 | 5.6 | 10.7 | 6.0 |

TABLE XXIII-continued

| Stock | 1 | 2 | 3 | 4 | 5 | 6 | 7 | 8 | 9 | 10 |
|---|---|---|---|---|---|---|---|---|---|---|
| R Max. in./lb. | 73.0 | 74.0 | 60.7 | 69.8 | 74.2 | 90.6 | 74.2 | 81.2 | 78.6 | 88.2 |
| R Min. in./lb. | 12.0 | 11.3 | 15.2 | 14.1 | 13.8 | 13.2 | 13.1 | 14.1 | 9.0 | 9.8 |
| Rheometer Data at 164°C | | | | | | | | | | |
| $T_{90}-t_2$, min. | 4.2 | 5.7 | 7.3 | 5.6 | 2.5 | 16.2 | 2.3 | 2.8 | 2.3 | 2.0 |
| R Max. in./lb. | 80.3 | 66.7 | 69.8 | 71.7 | 76.4 | 88.2 | 68.0 | 73.6 | 77.8 | 82.2 |
| R Min. in./lb. | 11.6 | 14.8 | 16.2 | 15.4 | 14.7 | 17.6 | 14.0 | 14.6 | 8.3 | 9.4 |
| Reversion, in./lb. (10 min.) | 13.2 | 1.4 | 5.0 | 0.6 | 3.9 | 0.0 | 10.2 | 8.4 | 10.0 | 3.3 |
| Stress-Strain Data at 144°C | | | | | | | | | | |
| Cure Time, min. | 35 | 60 | 60 | 50 | 25 | 80 | 15 | 15 | 35 | 25 |
| 300% Modulus, psi | 860 | 700 | 560 | 670 | 880 | 1010 | 890 | 990 | 1780 | 1850 |
| Ult. Tensile, psi | 3190 | 3460 | 2450 | 3110 | 3600 | 2580 | 2840 | 3440 | 3840 | 3720 |
| Ult. Elongation, % | 600 | 650 | 600 | 670 | 660 | 470 | 640 | 620 | 530 | 500 |

Table XXIV further illustrates cross-linking properties in natural rubber. Three parts by weight of the cross-linking agent is mixed with 157 parts by weight of Masterbatch A. The cross-linking agent and stock number of Table XXIV are selected as follows:

| Stock No. | Cross-linking Agent |
|---|---|
| 1 | 1,2-bis(O,O'-diisopropylphosphorotrithioyl)ethane |
| 2 | 1,2-bis(O,O'-diethylphosphorotrithioyl)-1-phenylethane |
| 3 | 2-[β-(2-benzothiazolyldithioethyl)]-5- or -6-(2-benzothiazolyldithio)bicyclo(2.2.1)-heptane |
| 4 | 2-[β-(O,O'-diethylphosphorotrithioylethyl)]-5- or -6-(O,O'-diethylphosphorotrithioyl)bicyclo-(2.2.1)heptane |
| 5 | 1,2-di(hexahydro-(1H)-azepin-1-ylthiocarbamoyldithio)-n-octane |
| 6 | 1,2-di(hexahydro-(1H)-azepin-1-ylthiocarbamoyldithio)-n-hexane |
| 7 | 1,2-di(hexahydro-(1H)-azepin-1-ylthiocarbamoyldithio)-1-phenylethane |
| 8 | α,α'-bis(hexahydro-(1H)-azepin-1-ylthiocarbamoyldithio)-p-xylene |

TABLE XXIV

| Stock | 1 | 2 | 3 | 4 | 5 | 6 | 7 | 8 |
|---|---|---|---|---|---|---|---|---|
| Masterbatch A | 157.0 | → | | | | | | |
| Cross-linking Agent | 3.0 | → | | | | | | |
| Mooney Scorch at 121°C | | | | | | | | |
| $t_5$, min. | >144 | 28.7 | >120 | >120 | 12.4 | 15.6 | 5.0 | 40.3 |
| Rheometer Data at 144°C | | | | | | | | |
| $t_{90}-t_2$, min. | 79.1 | 22.4 | — | 73.0 | 31.5 | 33.2 | 19.5 | 24.5 |
| R Max. | 38.5 | 41.0 | — | 32.2 | 47.0 | 47.4 | 40.2 | 48.8 |
| R Min. | 3.5 | 4.3 | — | 7.6 | 4.3 | 4.2 | 4.6 | 4.2 |
| Rheometer Data at 164°C | | | | | | | | |
| $t_{90}-t_2$, min. | 21.9 | 5.3 | 67.0 | 20.4 | 7.0 | 8.5 | 3.9 | 5.0 |
| R Max. | 38.7 | 38.8 | 15.8 | 28.0 | 39.1 | 40.1 | 33.0 | 41.0 |
| R Min. | 3.6 | 4.4 | 7.4 | 6.4 | 2.4 | 2.5 | 4.6 | 2.2 |
| Reversion | 0.0 | 0.0 | — | — | 0.0 | 0.0 | 0.2 | 0.1 |
| Stress-Strain Data at 144°C | | | | | | | | |
| Cure Time, min. | 180 | 80 | — | 160 | 120 | 120 | 80 | 90 |
| 300% Modulus, psi | 950 | 1060 | — | 590 | 1120 | 1200 | 1010 | 1200 |
| Ult. Tensile, psi | 3400 | 3520 | — | 2500 | 3540 | 3160 | 3200 | 3210 |
| Ult. Elongation, % | 630 | 600 | — | 600 | 590 | 550 | 600 | 520 |

Although the invention has been illustrated by typical examples, it is not limited thereto. Changes and modifications of the examples of the invention herein chosen for purposes of disclosure can be made which do not constitute departure from the spirit and scope of the invention.

The embodiments of the invention in which an exclusive property or privilege is claimed are defined as follows:

1. The method of cross-linking which comprises incorporating into diene rubber a cross-linking amount of (AccS-S$_x$)$_n$R-S$_x$-SAcc where AccS is the same or different accelerating moiety, $x$ is 1, 2, 3 or 4, $n$ is 1, 2 or 3 and R is an organic radical of 1 to 24 carbon atoms of valence $n+1$ selected from the group consisting of a. divalent radical of the formula $(X)_{n'}$ where $n'$ is 1 to 24, each X is the same or different and is

where Z and Z' independently are hydrogen, alkyl, cycloalkyl, benzyl or phenyl, b. divalent radical of the formula

where each $n''$ independently is 1 to 23, $m$ is zero, 1 or 2, X has the same meaning as before and Y is oxygen, sulfur, —SO$_2$—, HN<, C$_6$H$_5$N<, lower alkyl-N<, —C(O)O—, divalent cyclic radical of group (c) below or divalent aromatic radical of group (e) below, c. divalent cyclic radical each valence of which is on a ring carbon atom of an aliphatic ring said radical being the radical derived from removal of hydrogen from carbon in monocyclic, bi(monocyclic), bicyclic or tricyclic hydrocarbon or said hydrocarbon having up to two ring carbon atoms replaced by oxygen, d. divalent acyclic olefinic unsaturated radical, e. divalent aromatic radical selected from the group consisting of anthrylene and radicals derived by removal of hydrogen from two ring carbon atoms of a compound of the formula

[Structures: thiophene with (Z")ₓ', pyridine with (Z")ₓ', benzene with (Z")ₓ', biphenyl with (Z")ₓ' groups, naphthalene with (Z")ₓ' groups]

and

[Structure: two benzene rings connected by -(Y')- each with (Z")ₓ' groups]

where each Z" independently is hydrogen, lower alkyl, hydroxy, lower alkoxy, acetyl, phenyl, chloro or nitro, Y' is oxygen, sulfur, $-SO_2-$, $-CO-$, lower alkylene or lower alkylidene and $x'$ is 1 to 4, f. combination of the formula -T-T'- where one valence is linked to cyclic carbon and the other to acyclic carbon, T being selected from the group consisting of (a), (b), (c), (d) and (e) and T' being selected from a different member of the same group, g. straight and branched chain alkylene substituted by one or more radicals selected from the group consisting of oxo, hydroxy, alkoxy, hydroxysubstituted alkoxy, alkoxy-substituted alkoxy, carboxy, carboxy substituted alkoxy, carboalkoxy and acyloxy, h. trivalent radical selected from the group consisting of radical derived by removal of one hydrogen from a radical of group (a), (b), (c), (d), (e), (f) or (g), radical of the formula $-A'-OCH_2CH(OA'-)CH_2OA'-$ where A' is lower alkylene and radical of the formula

A-C(A'OOCA'-)₃ where A is lower alkyl and A' independently is lower alkylene, i. tetravalent radical selected from the group consisting of a radical derived by removal of two hydrogen atoms from a radical of group (a), (b), (c), (d), (e), (f) or (g), radical of the formula

[Structure: -CH₂-C and -CH₂-C linked by O forming epoxide-like ring with =C-CH₂- groups]

and radical of the formula

C(A'OOCA'—)₄ where A' is independently lower alkylene; and the accelerating moiety is selected from the group consisting of 1. radical of the formula

[Structure showing vicinal C-X' and C-N with C-S- group]

where the unsatisfied valences on the vicinal carbon atoms are satisfied independently by hydrogen, lower alkyl, benzyl, acetyl, carboalkoxy, phenyl, by one on each carbon together forming a double bond or by said carbon atoms being members of an unsubstituted aromatic or alicyclic ring, or aromatic ring substituted by a member of the group consisting of lower alkyl, halo, nitro, hydroxy, carboalkoxy, acetyl, lower alkoxy and phenyl and X' is S, O, or NH, 2. radical of the formula $$R_1\!\!\underset{R_2}{\overset{}{\diagdown}}\!\!N-\overset{X''}{\underset{\|}{C}}-S-$$

where $R_1$ and $R_2$ independently are hydrogen, alkyl, cycloalkyl, aralkyl, phenyl or substituted phenyl or $R_1$ and $R_2$ along with the nitrogen atom form a heterocycle of 4–8 carbon atoms, and $X''$ is O or S, 3. radical of the formula $$R_3O\!\!\underset{R_4O}{\overset{}{\diagdown}}\!\!\overset{S}{\underset{\|}{P}}-S-$$

where $R_3$ and $R_4$ independently are alkyl, cycloalkyl, aralkyl, phenyl or alkyl substituted phenyl, 4. radical of the formula $$R_5O-\overset{X''}{\underset{\|}{C}}-S-$$

where $R_5$ is alkyl, cycloalkyl, aralkyl, phenyl and substituted phenyl and $X''$ is O or S, 5. radical of the formula

[Two structures with R₆, R₇, R₈ substituents on C=N and C-N rings with C-S- groups]

where $R_6$, $R_7$ and $R_8$ independently are hydrogen, lower alkyl, lower alkoxy, phenyl, nitro, chloro, lower alkylthio, lower alkylamino, lower dialkylamino, lower dialkenylamino, heterocyclic amino or $R_7$ and $R_8$ along with the adjacent carbon atoms to which they are attached form ortho arylene; and the corresponding dihydro and tetrahydro radicals, 6. radical of the formula

[Structure with R₆, R₇ on C=N, C-N ring with C-S- group]

where $R_6$ and $R_7$ are independent and independently have the same meaning as before, 7. radical of the formula

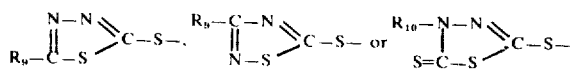

where $R_9$ is acetamido, lower alkyl, phenyl, chloro or bromo, and $R_{10}$ is lower alkyl or phenyl, 8. radical of the formula

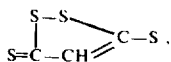

9. radical of the formula

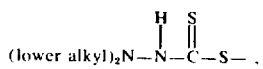

10. radical of the formula

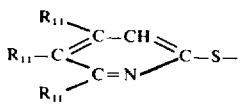

where each $R_{11}$ independently is hydrogen or lower alkyl, 11. radical of the formula

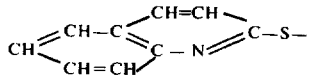 and 12. radical of the formula

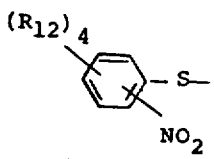

where independently each $R_{12}$ is hydrogen, alkyl, chloro, nitro, carboalkoxy, carboxy or acetyl; with the proviso that when the accelerating moiety is selected from the group consisting of (1), (5), (6), (7), (8), (10) and (11) R cannot be (b) and when the accelerating moiety is (1), (3) or (12) each Acc is different, and effecting cross-linking of the rubber.

2. The method of claim 1 where R is selected from the group consisting of (a), (b) and (c).

3. The method of claim 1 where $n$ is 1 and each Acc is different.

4. The method of claim 1 where $x$ is 1, $n$ is 1, each Acc is the same and R is selected from the group consisting of (a) where $n'$ is 2–12, and (b) where $n''$ is 1–11, $m$ is zero and Y is selected from the group consisting of —O—, —S— and phenylene.

5. The method of claim 4 where R is (a) and Z and Z' are hydrogen.

6. The method of claim 4 where R is (a), Z and Z' are hydrogen in all X's except one where Z is hydrogen and Z'0 is alkyl of 1–10 carbon atoms.

7. The method of claim 6 where $n'$ is 2.

8. The method of claim 4 where R is (b), Z and Z' are hydrogen, $n''$ is 1 and Y is phenylene.

9. The method of claim 4 where Acc-S- is 2-benzothiazolylthio.

10. The method of claim 5 where R is selected from the group consisting of dimethylene, 1-hexyl-1,2-dimethylene, 1-butyl-1,2-dimethylene and 1-phenyl-1,2-dimethylene.

11. The method of claim 10 where R is dimethylene.

12. The method of claim 4 where R is p-phenylenedimethylene.

13. The method of claim 4 where Acc-S— is 4,6-di(-substituted amino)-s-triazinylthio.

14. The method of claim 4 where Acc-S— is

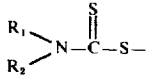

and $R_1$ and $R_2$ are lower alkyl or together with the nitrogen form a heterocycle.

15. The method of claim 14 where R is selected from the group consisting of dimethylene, phenylenedimethylene, 1-hexyl-1,2-dimethylene, 1-butyl-1,2-dimethylene and 1-phenyl-1,2-dimethylene.

16. The method of claim 15 where R is p-phenylenedimethylene.

17. The method of claim 4 where Acc-S— is

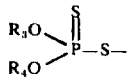

and $R_3$ and $R_4$ are lower alkyl.

18. The method of claim 17 where R is selected from the group consisting of dimethylene, phenylenedimethylene, 1-hexyl-1,2-dimethylene, 1-butyl-1,2-dimethylene and 1-phenyl-1,2-dimethylene.

19. The method of claim 18 where R is p-phenylenedimethylene.

20. The method of claim 15 where $R_1$ and $R_2$ are selected from the group consisting of methyl, ethyl, isopropyl and butyl.

21. The method of claim 20 where $R_1$ and $R_2$ are methyl.

22. The method of claim 15 where the heterocycle is selected from the group consisting of piperidino, hexahydro-1H-azepin-1-yl and 2,6-dimethylmorpholino.

23. The method of claim 15 where the heterocycle is pyrrolidinyl.

24. The method of claim 22 where the heterocycle is hexahydro-1-H-azepin-1-yl.

25. The method of claim 4 where the rubber composition also contains elemental sulfur.

26. The method of claim 4 where a combination of two cross-linking agents are incorporated into the rubber.

27. The method of claim 26 where Acc-S— in one of the cross-linking agents is

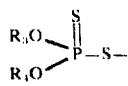

and R is selected from the group of (a) and (b).

28. The method of claim 27 where Acc-S— in the other cross-linking agent is 2-benzothiazolylthio.

29. The method of cross-linking which comprises incorporating into diene rubber a cross-linking amount of

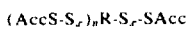

where AccS is the same or different accelerating moiety, $x$ is 1, 2, 3 or 4, $n$ is 1, 2 or 3 and R is an organic radical of 1 to 24 carbon atoms of valence $n + 1$ selected from the group consisting of a. divalent radical of the formula $(X)_{n'}$ where $n'$ is 1 to 24, each X is the same or different and is

where Z and Z' independently are hydrogen, alkyl, cycloalkyl, benzyl or phenyl, b. divalent radical of the formula

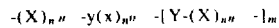

where each $n''$ independently is 1 to 23, $m$ is zero, 1 or 2, X has the same meaning as before and Y is oxygen, sulfur, $-SO_2-$, $HN<$, $C_6H_5N<$, lower alkyl-N<, $-C(O)O-$, divalent cyclic radical of group (c) below or divalent aromatic radical of group (e) below, c. divalent cyclic radical each valence of which is on a ring carbon atom of an aliphatic ring said radical being the radical derived from removal of hydrogen from carbon in monocyclic, bi(monocyclic), bicyclic or tricyclic hydrocarbon or said hydrocarbon having up to two ring carbon atoms replaced by oxygen, d. divalent acyclic olefinic unsaturated radical, e. divalent aromatic radical selected from the group consisting of anthrylene and radicals derived by removal of hydrogen from two ring carbon atoms of a compound of the formula

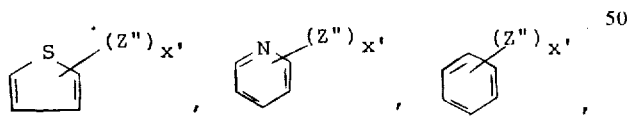

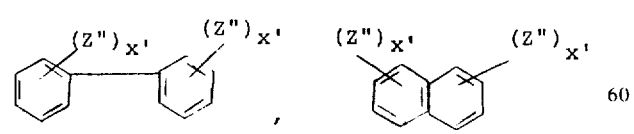

and 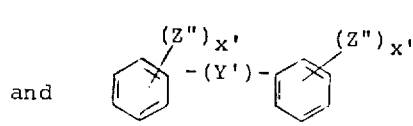

where each Z'' independently is hydrogen, lower alkyl, hydroxy, lower alkoxy, acetyl, phenyl, chloro or nitro, Y' is oxygen, sulfur, $-SO_2-$, $-CO-$, lower alkylene or lower alkylidene and $x'$ is 1 to 4, f. combination of the formula -T-T'- where one valence is linked to cyclic carbon and the other to acyclic carbon, T being selected from the group consisting of (a), (b), (c), (d) and (e) and T' being selected from a different member of the same group, g. straight and branched chain alkylene substituted by one or more radicals selected from the group consisting of oxo, hydroxy, alkoxy, hydroxysubstituted alkoxy, alkoxy-substituted alkoxy, carboxy, carboxy substituted alkoxy, carboalkoxy and acyloxy, h. trivalent radical selected from the group consisting of radical derived by removal of one hydrogen from a radical of group (a), (b), (c), (d), (e), (f) or (g), radical of the formula

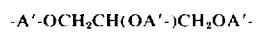

where A' is lower alkylene and radical of the formula

where A is lower alkyl and A' independently is lower alkylene, i. tetravalent radical selected from the group consisting of a radical derived by removal of two hydrogen atoms from a radical of group (a), (b), (c), (d), (e), (f) or (g), radical of the formula

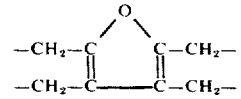

and radical of the formula

where A' is independently lower alkylene; and the accelerating moiety is

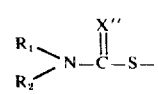

where $R_1$ and $R_2$ independently are hydrogen, alkyl, cycloalkyl, aralkyl, phenyl or substituted phenyl or $R_1$ and $R_2$ along with the nitrogen atom form a heterocycle of 4–8 carbon atoms, and X'' is O or S, and effecting cross-linking of the rubber.

30. The method of claim 29 where $x$ is 1, $n$ is 1, each Acc is the same and R is selected from the group consisting of (a) where $n'$ is 2–12, and (b) where $n''$ is 1–11, $m$ is zero and Y is selected from the group consisting of $-O-$, $-S-$ and phenylene.

31. The method of claim 30 where R is (a).

32. The method of claim 31 where Z and Z' are hydrogen.

33. The method of claim 30 where R is (b).

34. The method of claim 33 where Z and Z' are hydrogen, n" is 1 and Y is phenylene.

35. The method of claim 30 where $R_1$ and $R_2$ are lower alkyl.

36. The method of claim 30 where $R_1$ and $R_2$ together with the nitrogen form a heterocycle.

37. The method of claim 35 where $R_1$ and $R_2$ are methyl and R is dimethylene.

38. The method of claim 36 where the heterocycle is hexahydro-1H-azepin-1-yl and R is dimethylene.

39. A method of cross-linking rubber which comprises incorporating into diene rubber a cross-linking amount of a mixture of AccS-S-R-S-SAcc and $Acc_1$S-S-R-S-$SAcc_1$ where AccS- is selected from the group consisting of 1. radical of the formula

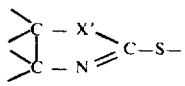

where the unsatisfied valences on the vicinal carbon atoms are satisfied independently by hydrogen, lower alkyl, benzyl, acetyl, carboalkoxy, phenyl, by one on each carbon together forming a double bond or by said carbon atoms being members of an unsubstituted aromatic or alicyclic ring, or aromatic ring substituted by a member of the group consisting of lower alkyl, halo, nitro, hydroxy, carboalkoxy, acetyl, lower alkoxy and phenyl and X' is S, O, or NH, 2. radical of the formula

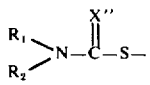

where $R_1$ and $R_2$ independently are hydrogen, alkyl, cycloalkyl, aralkyl, phenyl or substituted phenyl or $R_1$ and $R_2$ along with the nitrogen atom form a heterocycle of 4–8 carbon atoms, and X" is O, or S, and 3. radical of the formula

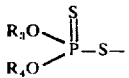

where $R_3$ and $R_4$ independently are alkyl, cycloalkyl, aralkyl, phenyl or alkyl substituted phenyl, and $Acc_1$S- is selected from a different member of the same group and R is selected from the group consisting of a. divalent radical of the formula $(X)_n$ where $n'$ is 1 to 24, each X is the same or different and is

Z-C-Z' where Z and Z' independently are hydrogen, alkyl, cycloalkyl, benzyl or phenyl, b. divalent radical of the formula

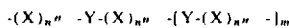

where each $n''$ independently is 1 to 23, $m$ is zero, 1 or 2, X has the same meaning as before and Y is oxygen, sulfur or phenylene; with the proviso that when the accelerating moiety is (1) R cannot be (b); and effecting cross-linking of the rubber.

40. A composition comprising diene rubber and a cross-linking amount of

where AccS is the same or different accelerating moiety, $x$ is 1, 2, 3 or 4, $n$ is 1, 2 or 3 and R is an organic radical of 1 to 24 carbon atoms of valence $n + 1$ selected from the group consisting of a. divalent radical of the formula $(X)_n$ where $n'$ is 1 to 24, each X is the same or different and is

where Z and Z' independently are hydrogen, alkyl, cycloalkyl, benzyl or phenyl, b. divalent radical of the formula

where each $n''$ independently is 1 to 23, $m$ is zero, 1 or 2, X has the same meaning as before and Y is oxygen, sulfur, $-SO_2-$, HN<, $C_6H_5N<$, lower alkyl-N<, $-C(O)O-$, divalent cyclic radical of group (c) below or divalent aromatic radical of group (e) below, c. divalent cyclic radical each valence of which is on a ring carbon atom of an aliphatic ring said radical being the radical derived from removal of hydrogen from carbon in monocyclic, bi(monocyclic), bicyclic or tricyclic hydrocarbon or said hydrocarbon having up to two ring carbon atoms replaced by oxygen, d. divalent acyclic olefinic unsaturated radical, e. divalent aromatic radical selected from the group consisting of anthrylene and radicals derived by removal of hydrogen from two ring carbon atoms of a compound of the formula

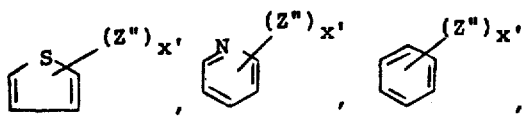

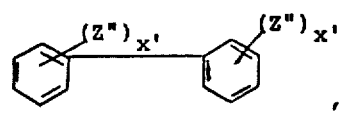

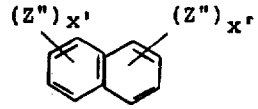

and

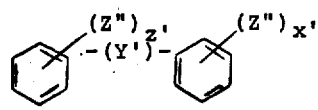

where each Z" independently is hydrogen, lower alkyl, hydroxy, lower alkoxy, acetyl, phenyl, chloro or nitro, Y' is oxygen, sulfur, $-SO_2-$, $-CO-$, lower alkylene or lower alkylidene and $x'$ is 1 to 4, f. combination of the formula -T-T'- where one valence is linked to cyclic carbon and the other to acyclic carbon, T being selected from the group consisting of (a), (b), (c), (d) and (e) and T' being selected from a different member of the same group, g. straight and branched chain alkylene substituted by one or more radicals selected from the group consisting of oxo, hydroxy, alkoxy, hydroxysubstituted alkoxy, alkoxysubstituted alkoxy, carboxy, carboxy substituted alkoxy, carboalkoxy and acyloxy, h. trivalent radical selected from the group consisting of radical derived by removal of one hydrogen from a radical of group (a), (b), (c), (d), (e), (f) or (g), radical of the formula

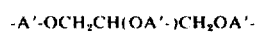

where A' is lower alkylene and radical of the formula

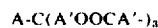

where A is lower alkyl and A' independently is lower alkylene, i. tetravalent radical selected from the group consisting of a radical derived by removal of two hydrogen atoms from a radical of group (a), (b), (c), (d), (e), (f) or (g), radical of the formula

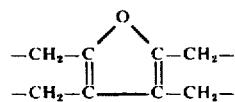

and radical of the formula

where A' is independently lower alkylene; and the accelerating moiety is selected from the group consisting of 1. radical of the formula

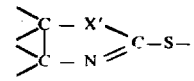

where the unsatisfied valences on the vicinal carbon atoms are satisfied independently by hydrogen, lower alkyl, benzyl, acetyl, carboalkoxy, phenyl, by one on each carbon together forming a double bond or by said carbon atoms being members of an unsubstituted aromatic or alicyclic ring, or aromatic ring substituted by a member of the group consisting of lower alkyl, halo, nitro, hydroxy, carboalkoxy, acetyl, lower alkoxy and phenyl and X' is S, O, or NH, 2. radical of the formula

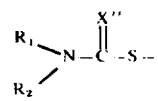

where $R_1$ and $R_2$ independently are hydrogen, alkyl, cycloalkyl, aralkyl; phenyl or substituted phenyl or $R_1$ and $R_2$ along with the nitrogen atom form a heterocycle of 4–8 carbon atoms, and X'' is O or S, 3. radical of the formula

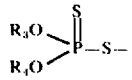

where $R_3$ and $R_4$ independently are alkyl, cycloalkyl, aralkyl, phenyl or alkyl substituted phenyl, 4. radical of the formula

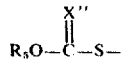

where $R_5$ is alkyl, cycloalkyl, aralkyl, phenyl and substituted phenyl and X'' is O or S, 5. radical of the formula

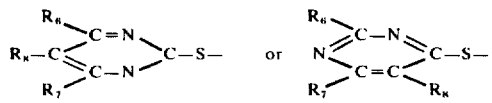

where $R_6$, $R_7$ and $R_8$ independently are hydrogen, lower alkyl, lower alkoxy, phenyl, nitro, chloro, lower alkylthio, lower alkylamino, lower dialkylamino, lower dialkenylamino, heterocyclic amino or $R_7$ and $R_8$ along with the adjacent carbon atoms to which they are attached form ortho arylene; and the corresponding dihydro and tetrahydro radicals, 6. radical of the formula

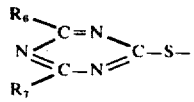

where $R_6$ and $R_7$ are independent and independently have the same meaning as before, 7. radical of the formula

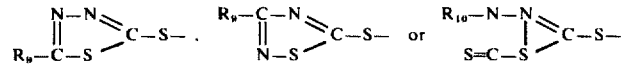

where $R_9$ is acetamido, lower alkyl, phenyl, chloro or bromo, and $R_{10}$ is lower alkyl or phenyl, 8. radical of the formula

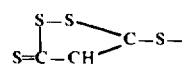

9. radical of the formula

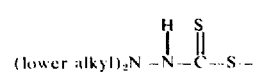

10. radical of the formula

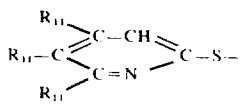

where each $R_{11}$ independently is hydrogen or lower alkyl, 11. radical of the formula

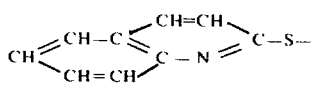

and 12. radical of the formula

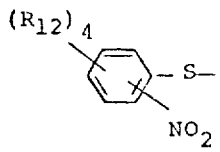

where independently each $R_{12}$ is hydrogen, alkyl, chloro, nitro, carboalkoxy, carboxy or acetyl; with the proviso that when the accelerating moiety is selected from the group consisting of (1), (5), (6), (7), (8), (10) and (11) R cannot be (b) and when the accelerating moiety is (1), (3) or (12) each Acc is different.

41. A composition comprising diene rubber and a cross-linking amount of $$(AccS-S_x-)_nR-S_x-SAcc$$

where AccS is the same or different accelerating moiety, $x$ is 1, 2, 3 or 4, $n$ is 1, 2 or 3 and R is an organic radical of 1 to 24 carbon atoms of valence $n + 1$ selected from the group consisting of a. divalent radical of the formula $(X)_{n'}$ where $n'$ is 1 to 24, each X is the same or different and is

where Z and Z' independently are hydrogen, alkyl, cycloalkyl, benzyl or phenyl, b. divalent radical of the formula

where each $n''$ independently is 1 to 23, m is zero, 1 or 2, X has the same meaning as before and Y is oxygen, sulfur, —SO$_2$—, HN<, C$_6$H$_5$N<, lower alkyl-N<, —C(O)O—, divalent cyclic radical of group (c) below or divalent aromatic radical of group (e) below, c. divalent cyclic radical each valence of which is on a ring carbon atom of an aliphatic ring said radical being the radical derived from removal of hydrogen from carbon in monocyclic, bi(monocyclic), bicyclic or tricyclic hydrocarbon or said hydrocarbon having up to two ring carbon atoms replaced by oxygen, d. divalent acyclic olefinic unsaturated radical, e. divalent aromatic radical selected from the group consisting of anthrylene and radicals derived by removal of hydrogen from two ring carbon atoms of a compound of the formula

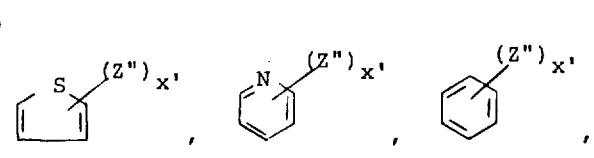

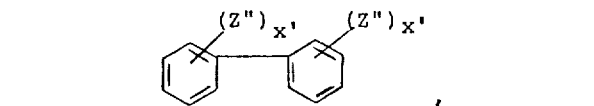

and

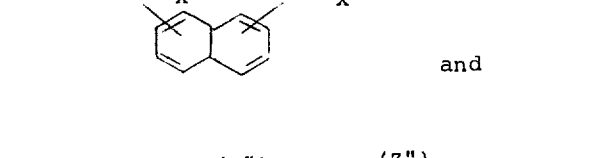

where each $Z''$ independently is hydrogen, lower alkyl, hydroxy, lower alkoxy, acetyl, phenyl, chloro or nitro, Y' is oxygen, sulfur, —SO$_2$—, —CO—, lower alkylene or lower alkylidene and $x'$ is 1 to 4, f. combination of the formula -T-T'- where one valence is linked to cyclic carbon and the other to acyclic carbon, T being selected from the group consisting of (a), (b), (c), (d) and (e) and T' being selected from a different member of the same group, g. straight and branched chain alkylene substituted by one or more radicals selected from the group consisting of oxo, hydroxy, alkoxy, hydroxysubstituted alkoxy, alkoxysubstituted alkoxy, carboxy, carboxy substituted alkoxy, carboalkoxy and acyloxy, h. trivalent radical selected from the group consisting of radical derived by removal of one hydrogen from a radical of group (a), (b), (c), (d), (e), (f), or (g), radical of the formula

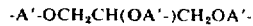

where A' is lower alkylene and radical of the formula

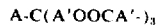

where A is lower alkyl and A' independently is lower alkylene, i. tetravalent radical selected from the group consisting of a radical derived by removal of two hydrogen atoms from a radical of group (a), (b), (c), (d), (e), (f) or (g), radical of the formula

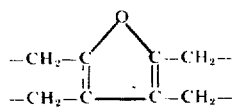

and radical of the formula

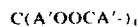

where A' is independently lower alkylene; and the accelerating moiety is

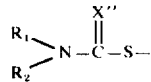

where $R_1$ and $R_2$ independently are hydrogen, alkyl, cycloalkyl, aralkyl, phenyl or substituted phenyl or $R_1$ and $R_2$ along with the nitrogen atom form a heterocycle of 4–8 carbon atoms, and $X''$ is O or S.

42. A composition comprising diene rubber and a cross-linking amount of a mixture of AccS-S-R-S-SAcc and $Acc_1$ S-S-R-S-$SAcc_1$ where AccS- is selected from the group consisting of 1. radical of the formula

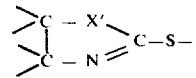

where the unsatisfied valences on the vicinal carbon atoms are satisfied independently by hydrogen, lower alkyl, benzyl, acetyl, carboalkoxy, phenyl, by one on each carbon together forming a double bond or by said carbon atoms being members of an unsubstituted aromatic or alicyclic ring, or aromatic ring substituted by a member of the group consisting of lower alkyl, halo, nitro, hydroxy, carboalkoxy, acetyl, lower alkoxy and phenyl and X' is S, O, or NH, 2. radical of the formula

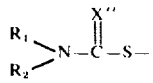

where $R_1$ and $R_2$ independently are hydrogen, alkyl, cycloalkyl, aralkyl, phenyl or substituted phenyl or $R_1$ and $R_2$ along with the nitrogen atom form a heterocycle of 4–8 carbon atoms, and $X''$ is O, or S, and 3. radical of the formula

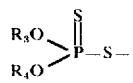

where $R_3$ and $R_4$ independently are alkyl, cycloalkyl, aralkyl, phenyl or alkyl substituted phenyl, and $Acc_1S$— is selected from a different member of the same group and R is selected from the group consisting of a. divalent radical of the formula $(X)_n$ where $n'$ is 1 to 24, each X is the same or different and is

where Z and Z' independently are hydrogen, alkyl, cycloalkyl, benzyl or phenyl, b. divalent radical of the formula

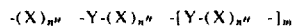

where each n' independently is 1 to 23, m is zero, 1 or 2, X has the same meaning as before and Y is oxygen, sulfur or phenylene with the proviso that when the accelerating moiety is (1), R cannot be (b).

* * * * *